US011814678B2

(12) United States Patent
Singer et al.

(10) Patent No.: US 11,814,678 B2
(45) Date of Patent: *Nov. 14, 2023

(54) UNIVERSAL SHORT ADAPTERS FOR INDEXING OF POLYNUCLEOTIDE SAMPLES

(71) Applicant: Illumina, Inc., San Diego, CA (US)

(72) Inventors: Tatjana Singer, San Diego, CA (US);
Ryan Kelley, San Diego, CA (US);
Gordon Bean, San Diego, CA (US);
Eric Vermaas, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/307,973

(22) Filed: May 4, 2021

(65) Prior Publication Data
US 2021/0262026 A1  Aug. 26, 2021

Related U.S. Application Data

(63) Continuation of application No. 15/973,210, filed on May 7, 2018, now Pat. No. 11,028,436.
(Continued)

(51) Int. Cl.
*C12Q 1/6874* (2018.01)
*G16B 25/00* (2019.01)
(Continued)

(52) U.S. Cl.
CPC ......... *C12Q 1/6874* (2013.01); *C12Q 1/6869* (2013.01); *G16B 25/00* (2019.02);
(Continued)

(58) Field of Classification Search
CPC .. C12Q 1/6874; C12Q 1/6869; C12Q 1/6806; G16B 25/00; G16B 30/00; G16B 30/10; G16B 25/20
See application file for complete search history.

(56) References Cited

U.S. PATENT DOCUMENTS 8,728,736 B2  5/2014 Leamon et al.
8,822,150 B2  9/2014 Bignell et al.
(Continued)

FOREIGN PATENT DOCUMENTS

WO  WO 1998/044151  10/1998
WO  WO 2000/018957  4/2000
(Continued)

OTHER PUBLICATIONS

US 11,629,382 B2, 04/2023, Salk et al. (withdrawn)
(Continued)

*Primary Examiner* — Kyoung Lee
(74) *Attorney, Agent, or Firm* — Weaver Austin Villeneuve & Sampson LLP

(57) ABSTRACT

The disclosed embodiments concern index oligonucleotides configured to identify sources of samples of nucleic acids and methods, apparatus, systems and computer program products for identifying and making the index oligonucleotides. In some implementations, the index oligonucleotides include a set of index sequences, a Hamming distance between any two index sequences of the set of index sequences meeting one or more criteria. System, apparatus, and computer program products are also provided for determining a sequence of interest using the index oligonucleotides.

20 Claims, 17 Drawing Sheets

Specification includes a Sequence Listing.

Related U.S. Application Data

(60) Provisional application No. 62/524,390, filed on Jun. 23, 2017, provisional application No. 62/503,272, filed on May 8, 2017.

(51) Int. Cl.
    *C12Q 1/6869*      (2018.01)
    *G16B 30/00*      (2019.01)
    *G16B 30/10*      (2019.01)
    *G16B 25/20*      (2019.01)

(52) U.S. Cl.
CPC .............. *G16B 30/00* (2019.02); *G16B 30/10* (2019.02); *G16B 25/20* (2019.02)

(56) References Cited

U.S. PATENT DOCUMENTS

| | | |
|---|---|---|
| 9,040,256 B2 | 5/2015 | Grunenwald et al. |
| 9,752,188 B2 | 9/2017 | Schmitt et al. |
| 10,287,631 B2 | 5/2019 | Salk et al. |
| 10,370,713 B2 | 8/2019 | Salk et al. |
| 10,385,393 B2 | 8/2019 | Salk et al. |
| 10,570,451 B2 | 2/2020 | Salk et al. |
| 10,604,804 B2 | 3/2020 | Salk et al. |
| 10,689,699 B2 | 6/2020 | Salk et al. |
| 10,689,700 B2 | 6/2020 | Salk et al. |
| 10,711,304 B2 | 7/2020 | Salk et al. |
| 10,752,951 B2 | 8/2020 | Salk et al. |
| 10,760,127 B2 | 9/2020 | Salk et al. |
| 11,028,435 B2 | 6/2021 | Kelley et al. |
| 11,028,436 B2 * | 6/2021 | Singer .................... G16B 25/00 |
| 11,047,006 B2 | 6/2021 | Salk et al. |
| 11,098,359 B2 | 8/2021 | Salk et al. |
| 11,118,225 B2 | 9/2021 | Salk et al. |
| 11,130,996 B2 | 9/2021 | Salk et al. |
| 11,155,869 B2 | 10/2021 | Salk et al. |
| 11,198,907 B2 | 12/2021 | Salk et al. |
| 11,242,562 B2 | 2/2022 | Salk et al. |
| 11,549,144 B2 | 1/2023 | Salk et al. |
| 11,555,220 B2 | 1/2023 | Salk et al. |
| 11,608,529 B2 | 3/2023 | Salk et al. |
| 2015/0044687 A1 | 2/2015 | Schmitt et al. |
| 2015/0087537 A1 | 3/2015 | Hubbell |
| 2018/0142293 A1 | 5/2018 | Schmitt et al. |
| 2018/0334711 A1 * | 11/2018 | Kelley ................. C12Q 1/6811 |
| 2018/0334712 A1 | 11/2018 | Singer et al. |
| 2018/0363051 A1 | 12/2018 | Schmitt et al. |
| 2018/0363052 A1 | 12/2018 | Schmitt et al. |
| 2018/0363053 A1 | 12/2018 | Schmitt et al. |
| 2019/0093160 A1 | 3/2019 | Schmitt et al. |
| 2019/0093161 A1 | 3/2019 | Schmitt et al. |
| 2019/0093162 A1 | 3/2019 | Schmitt et al. |
| 2019/0119748 A1 | 4/2019 | Schmitt et al. |
| 2019/0119749 A1 | 4/2019 | Schmitt et al. |
| 2019/0271040 A1 | 9/2019 | Salk et al. |
| 2019/0284626 A1 | 9/2019 | Salk et al. |
| 2019/0284627 A1 | 9/2019 | Salk et al. |
| 2019/0292597 A1 | 9/2019 | Salk et al. |
| 2019/0323082 A1 | 10/2019 | Salk et al. |
| 2019/0338358 A1 | 11/2019 | Salk et al. |
| 2019/0352714 A1 | 11/2019 | Salk et al. |
| 2020/0318185 A1 | 10/2020 | Salk et al. |
| 2020/0392580 A1 | 12/2020 | Salk et al. |
| 2021/0254154 A1 | 8/2021 | Kelley et al. |
| 2021/0324470 A1 | 10/2021 | Salk et al. |
| 2021/0371920 A1 | 12/2021 | Salk et al. |
| 2021/0371921 A1 | 12/2021 | Salk et al. |
| 2021/0371922 A1 | 12/2021 | Salk et al. |
| 2021/0371923 A1 | 12/2021 | Salk et al. |
| 2021/0371924 A1 | 12/2021 | Salk et al. |
| 2021/0381048 A1 | 12/2021 | Salk et al. |
| 2022/0010376 A1 | 1/2022 | Salk et al. |
| 2022/0017961 A1 | 1/2022 | Salk et al. |
| 2022/0195523 A1 | 6/2022 | Salk et al. |
| 2022/0290231 A1 | 9/2022 | Salk et al. |

FOREIGN PATENT DOCUMENTS

| | | |
|---|---|---|
| WO | WO 2005/065814 | 7/2005 |
| WO | WO 2006/064199 | 6/2006 |
| WO | WO 2007/010251 | 1/2007 |
| WO | WO 2010/117620 A2 | 10/2010 |
| WO | WO 2011/100617 A2 | 8/2011 |
| WO | WO-2013142389 A1 | 9/2013 |
| WO | WO-2013181170 A1 | 12/2013 |
| WO | WO 2014/201273 A1 | 12/2014 |
| WO | WO 2015/106941 | 7/2015 |
| WO | WO 2016/018960 A1 | 2/2016 |
| WO | WO 2016/0176091 A1 | 11/2016 |
| WO | WO-2017100441 A1 | 6/2017 |
| WO | WO-2018175997 A1 | 9/2018 |
| WO | WO-2019094651 A1 | 5/2019 |
| WO | WO-2019160998 A1 | 8/2019 |
| WO | WO-2019178577 A1 | 9/2019 |
| WO | WO-2019222560 A1 | 11/2019 |
| WO | WO-2020014693 A1 | 1/2020 |
| WO | WO-2020081743 A1 | 4/2020 |
| WO | WO-2021022237 A1 | 2/2021 |

OTHER PUBLICATIONS

US 11,634,771 B2, 04/2023, Salk et al. (withdrawn)
CA Office Action dated Nov. 22, 2021, in Application No. CA3062174.
CA Office Action dated Nov. 24, 2021, in Application No. CA3060369.
European office action dated Mar. 10, 2022, in Application No. 18726000.5.
Singapore Supplementary Examination Report dated Jul. 9, 2021 issued in Application No. 11201910070P.
Notice of Allowance dated Feb. 10, 2021 issued in U.S. Appl. No. 15/968,613.
Notice of Allowance dated Feb. 26, 2021 issued in U.S. Appl. No. 15/968,613.
Notice of Allowance dated Mar. 19, 2021 issued in U.S. Appl. No. 15/968,613.
Notice of Allowance dated Feb. 16, 2021 issued in U.S. Appl. No. 15/973,210.
Notice of Allowance dated Mar. 18, 2021 issued in U.S. Appl. No. 15/973,210.
International Search Report dated Jun. 26, 2018 issued in Application No. PCT/US2018/030539.
International Preliminary Report on Patentability dated Nov. 14, 2019 issued in Application No. PCT/US2018/030539.
Singapore Written Opinion dated Jan. 14, 2021 issued in Application No. SG 11201909697T.
International Preliminary Report on Patentability dated Mar. 27, 2019 issued in Application No. PCT/US2018/031459.
International Search Report and Written Opinion dated Sep. 11, 2018 issued in Application No. PCT/US2018/031459.
European Examination Report dated Feb. 15, 2021 issued in Application No. 18 727 517.7-1118.
Illumina, "TruSeq Library Prep Pooling Guide," Illumina Proprietary, Document #15042173 v01, Nov. 2015, 26 pages.
Nick Caruccio et al.: "Nextera(TM) Technology for NGS DNA Library Preparation: Simultaneous Fragmentation and Tagging by In Vitro Transposition" Oct. 1, 2009 (Oct. 1, 2009), vol. 16-3.
U.S. Appl. No. 17/307,959, filed May 4, 2021, Kelley et al.
Bystrykh, L.V. "Generalized DNA Barcode Design Based on Hamming Codes", PLoS ONE, May 17, 2012, vol. 7, No. 5, pp. e36852.
CA Office Action dated Dec. 5, 2022 in Application No. CA3060369.
U.S. Non-Final office Action dated Dec. 30, 2022 in U.S. Appl. No. 17/307,959.
U.S. Notice of Allowance dated Jun. 8, 2023, in U.S. Appl. No. 17/307,959.

* cited by examiner

Insert with double stranded universal Nextera adapters (A + B)

A                                                                                           B

[BLOCK]5'-TCGTCGGCAGCGTC|AGATGTGTATAAGAGACAG-3'--p--Insert-5'CTGTCTCTTATACACATCT|CCGAGCCCACGAGAC-3'[BLOCK]
[BLOCK]3'-AGCAGCCGTCGCAG|TCTACACATATTCTCTGTC-5'--Insert-p-3'GACAGAGAATATGTGTAGA|GGCTCGGGTGCTCTG-5'[BLOCK]

Nextera read1 Rev                                                                    HP11 Seq5

Figure 1G

Insert with forked universal Nextera adapters

[BLOCK]5'- TCGTCGGCAGCGTC|AGATGTGTATAAGAGACAG-3'--p--Insert-5'CTGTCTCTTATACACATCT|CCGAGCCCACGAGAC-3'[BLOCK]
[BLOCK]3'--CAGAGCACCCGAGCC|TCTACACATATTCTCTGTC-5'--Insert-p-3'GACAGAGAATATGTGTAGA|CTGCGACGGGTGCT-5'[BLOCK]

Nextera read1 Rev                                                                    HP11 Seq5
         33bp                                                                                34bp

Figure 1H

I7 Index read 1 primer
5'-CAAGCAGAAGACGGCATACGAGAT[i7]GTCTCGTGGGCTCGG-3'

I5 Index read 2 primer
5'-AATGATACGGCGACCACCGAGATCTACAC[i5]TCGTCGGCAGCGTC-3'

Dual index adapter
(Y-shaped)

Single index adapter
(Y-shaped)

Figure 4B

|   | 1 | 2 | 3 | 4 | 5 | 6 | 7 | 8 | 9 | 10 | 11 | 12 |
|---|---|---|---|---|---|---|---|---|---|----|----|----|
| A | i501 | i502 | i503 | i504 | i505 | i506 | i501 | i502 | i503 | i504 | i505 | i506 |
| B | i502 | i501 | i504 | i503 | i506 | i505 | i502 | i501 | i504 | i503 | i506 | i505 |
| C | i503 | i504 | i505 | i506 | i507 | i508 | i503 | i504 | i505 | i506 | i507 | i508 |
| D | i504 | i503 | i506 | i505 | i508 | i507 | i504 | i503 | i506 | i505 | i508 | i507 |
| E | i505 | i506 | i507 | i508 | i501 | i502 | i505 | i506 | i507 | i508 | i501 | i502 |
| F | i506 | i505 | i508 | i507 | i502 | i501 | i506 | i505 | i508 | i507 | i502 | i501 |
| G | i507 | i508 | i501 | i502 | i503 | i504 | i507 | i508 | i501 | i502 | i503 | i504 |
| H | i508 | i507 | i502 | i501 | i504 | i503 | i508 | i507 | i502 | i501 | i504 | i503 |

Figure 4C

|   | 1 | 2 | 3 | 4 | 5 | 6 | 7 | 8 | 9 | 10 | 11 | 12 |
|---|---|---|---|---|---|---|---|---|---|----|----|----|
| A | i701 | i705 | i702 | i703 | i706 | i704 | i708 | i709 | i707 | i711 | i710 | i712 |
| B | i702 | i706 | i701 | i704 | i705 | i703 | i707 | i710 | i708 | i712 | i709 | i711 |
| C | i706 | i704 | i705 | i702 | i703 | i701 | i710 | i712 | i709 | i707 | i711 | i708 |
| D | i705 | i703 | i706 | i701 | i704 | i702 | i709 | i711 | i710 | i708 | i712 | i707 |
| E | i707 | i711 | i708 | i709 | i712 | i710 | i702 | i703 | i701 | i705 | i704 | i706 |
| F | i708 | i712 | i707 | i710 | i711 | i709 | i701 | i704 | i702 | i706 | i703 | i705 |
| G | i712 | i710 | i711 | i708 | i709 | i707 | i704 | i706 | i703 | i701 | i705 | i702 |
| H | i711 | i709 | i712 | i707 | i710 | i708 | i703 | i705 | i704 | i702 | i706 | i701 |

```
                         SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: Synthesized

<400> SEQUENCE: 1
agatgtgtat aagagacag                                                 19

<210> SEQ ID NO 2
<211> LENGTH: 19
<212> TYPE: DNA
<213> ORGANISM: Artificial Sequence
<220> FEATURE:
<223> OTHER INFORMATION: Synthesized

<400> SEQUENCE: 2
ctgtctctta tacacatct                                                 19

<210> SEQ ID NO 3
<211> LENGTH: 14
<212> TYPE: DNA
<213> ORGANISM: Artificial Sequence
<220> FEATURE:
<223> OTHER INFORMATION: Synthesized

<400> SEQUENCE: 3
tcgtcggcag cgtc                                                      14

<210> SEQ ID NO 4
<211> LENGTH: 14
<212> TYPE: DNA
<213> ORGANISM: Artificial Sequence
<220> FEATURE:
<223> OTHER INFORMATION: Synthesized

<400> SEQUENCE: 4
gacgctgccg acga                                                      14

<210> SEQ ID NO 5
<211> LENGTH: 15
<212> TYPE: DNA
<213> ORGANISM: Artificial Sequence
<220> FEATURE:
<223> OTHER INFORMATION: Synthesized

<400> SEQUENCE: 5
gtctcgtggg ctcgg                                                     15

<210> SEQ ID NO 6
<211> LENGTH: 15
<212> TYPE: DNA
<213> ORGANISM: Artificial Sequence
<220> FEATURE:
<223> OTHER INFORMATION: Synthesized

<400> SEQUENCE: 6
```

```
ccgagcccac gagac                                                  15

<210> SEQ ID NO 7
<211> LENGTH: 24
<212> TYPE: DNA
<213> ORGANISM: Artificial Sequence
<220> FEATURE:
<223> OTHER INFORMATION: Synthesized

<400> SEQUENCE: 7
caagcagaag acggcatacg agat                                        24

<210> SEQ ID NO 8
<211> LENGTH: 29
<212> TYPE: DNA
<213> ORGANISM: Artificial Sequence
<220> FEATURE:
<223> OTHER INFORMATION: Synthesized

<400> SEQUENCE: 8
aatgatacgg cgaccaccga gatctacac                                   29

<210> SEQ ID NO 9
<211> LENGTH: 10260
<212> TYPE: DNA
<213> ORGANISM: Artificial Sequence
<220> FEATURE:
<223> OTHER INFORMATION: Synthesized

<400> SEQUENCE: 9
tgttcaccat cacctgttgc gtaggtggtg acgaacaaca acgccttgtt gtattccacc   60
tgtaaggtgg cacggaacaa ctcaacgctt tctggtatcc gagtcatagg agactgcgaa  120
agctggaatg gatcaaggca tcagtctcgt ctgactctac cgaagattct taggagcctc  180
cctctacatg ttctcgtgca gcgttggtat ataccaacgc aatagctgag gcgatcaga   240 caatataggt tggcgcgaac atggttgact gcaaccagtc tccattgccg cttgccatta  300
agcgaattag gataggccga gtgcagacag acatgagtga taaccgtaat cggttacggc  360
taccgcctcg cgttattcta ttcataaggt cctgcggaac aacactgtta ggtgtcaccg  420
acatatccag gtgcgcttga tggagtactt caagacgtcc attgcgcggt gccatataac  480
cagtggcact tgacaatgtc cgacctaacg tagttcggta gccgcactct attatgtctc  540
agaaccgagt gaggttagac gttaattacg accggccgta cctcgtgcgt ttctacatac  600
acttcaagcg gtcctggata aatcaccagc ggctgttgat caatcggctg tggctaatca  660
ttaagacaag ccggagtgga aacttatcct ggtccgcttc ctcgcttcgg tctatcctaa  720
gaacttcctt aggtccttcc tatggagatt cgcaagagcc accacgacat gttgtagtgc  780
tcatagattg ctgcgagcca cagcacggag tgatgtaaga ccgttcaagg ttacctggaa  840
aagcatcttg ggatgctcca aacagacggc ggtgagtaat ctagtgctct tcgacatctc  900
cgtctcatat tactctgcgc tcagaaggcg ctgaggaata gacaccatgt agtgttgcac  960
atgtaacgtt gcacggtacc tctaggcgcg ctcgaatata caagttattg tggaccgcca 1020
atcggcgaag gctaatagga aatgcgaaca ggcataggtg tggcctctgt caattctcac 1080
gattctgaat agcctcaggc atgttgttgg gcaccaccaa accaagcagg gttggatgaa 1140
tatcactctg cgctgtctca cgatgcggtt tagcataacc gtccaccgct acttgttatc 1200
gagaggttcg agagaaccta ctggcaagag tcaatggaga tccgccaatt cttattggcc 1260
```

```
actctattgt gtctcgccac atccaggtat gcttgaacgc aagttgacaa ggaccagtgg    1320
ttgtatcagg ccacgctgaa gaatacctat aggcgttcgc ctaataaccg tcggcggtta    1380
cgagaggcgt tagagaatac ccgacagact ttagtgagtc attggcttct gccaatcctc    1440
aattcttgga ggcctccaag taggctcgcg cgaatctata gttcggagtt acctaagacc    1500
gcgtgctgtg atacatcaca tgtggtccgg cacaacttaa cagcaatcgt tgatggctac    1560
catatgcgat tgcgcatagc gcgtccacct atacttgttc gctgacgttg atcagtacca    1620
ttaaccttcg ccggttccta tacgtgaagg cgtacaggaa aggtatggcg gaacgcaata    1680
tgtctggcct cactcaattc acagtaagat gtgacggagc ctgagccggt tcagattaac    1740
tgccggtcag cattaactga agtactcatg gacgtctgca ccgcgtatag ttatacgcga    1800
gtaacttggt acggtccaac cgcttagaat tatccgaggc aacgaggccg ggtagaatta    1860
cctaacacag ttcggtgtga tggtagagat caacgagagc aagcgcgctt ggatatatcc    1920
gtggtatctg acaacgctca attccataag gccttgcgga gctcttaact atctccggtc    1980
cggatgcttg taagcatcca aacggtctat ggtaactcgc gtggacaagt acaagtggac    2040
tcctggttgt cttcaaccac tcgctatgag ctatcgcaga cattagtgcg tgccgacata    2100
agtagagccg gacgagatta cgtgcttgct tacatccatc gactgagtag agtcagacga    2160
ataatccgtg gcggcttaca gagaatggtt agaggcaacc tcacaacagt ctgtggtgac    2220
gaactgagcg aggtcagata aaggccacgg ggaattgtaa cctgaccact ttcagttgtc    2280
cgcattccgt tatgccttac gtattgacgt acgccagtac aaccatagaa ggttgcgagg    2340
ttacgcacct ccgtatgttc aagatacacg ggagcgtgta attgatactg ccagcgtca    2400
caccgatgtg tgttagcaca ttggcagcgt ccaatgatac gcataagctt atgcggatcc    2460
gcttctctgg atcctctcaa cacgctagt tgtaatcgac tgattatacg cagccgcgta    2520
tataacagct cgcggtgatc catagtaagg tgcgacggaa gagcgacgat agatagtagc    2580
ttcttacttg cctccgtcca ctacacatgg tcgtgtgcaa acttacggat gtccgtaagc    2640
acagtgtatg gtgacacgca ttgctctatt ccatctcgcc ccaaggcctt ttggaattcc    2700
taatgtgtct cggcacactc actcggcaat gtctaatggc aggatgtgct gaagcacatc    2760
tatcttgtag cgctccacga ttcactcact cctgtctgtc ccatcattag ttgctgccga    2820
atgagatcat gcagagctgc tgtcgctggt cactatcaac ctctgcagcg tctcatgata    2880
aggataatgt gaagcggcac cgcacgactg tatgtagtca gttaccgtgg accgttacaa    2940
aacaagtaca ggtggacgtg aacatcgcgc ggtgctatat tcaccaactt ctgttggtcc    3000
aatggattga ggcaagccag ctccactaat tcttgtcggc ttgttgaatg ccaccaggca    3060
acacaggtgg gtgtgaacaa tccacgtgtt cttgtacacc gagcttgccg agatccatta    3120
cgccatatct tattgcgctc gtaactgaag acggtcagga aacgcacgag ggtatgtaga    3180
tgccaactgg cattggtcaa gacgtggtct agtacaactc caacgttcgg tggtacctaa    3240
gcgaactccg ataggtctta atagcggaat gcgataaggc taattagcgt cggccgatac    3300
gccacctact attgttcgtc catcgtcatt tgctactgcc cgtgtcgtgg tacactacaa    3360
accgtgtggt gttacacaac gcgtattaat atacgccggc tatcggaccg cgctaagtta    3420
ttgaatgttg ccaggcacca gaggcctatt agaattcgcc aattccatct ggccttgctc    3480
tccggactag cttaagtcga tcataccgtt ctgcgttacc aatctagaga ggctcgagag    3540
acaactactg tggtcgtca tgtgataact cacagcggtc caataggaat tggcgaaggc    3600
atggcgcctg gcaatattca ttaacggtgt ccggtaacac cctcacgagg ttctgtagaa    3660
```

```
gaattacaag aggccgtgga ctagattgcg tcgagccata aagacattag ggagtgccga   3720
atatgcatgt gcgcatgcac gacgcatcgt agtatgctac cgcagtggct tatgacaatc   3780
tcactgtccg ctgtcactta aactcgccgg ggtctattaa aacgttagtt ggtaccgacc   3840
gcgtggatgg atacaagcaa tggtgttatg caacaccgca tgtggcgcat cacaatatgc   3900
aattggcgcc ggccaatatt acgttagccg gtaccgatta cctccggttg ttcttaacca   3960
gagatccgct agagcttatc cgaggccaag tagaattgga tccgttatgt cttaccgcac   4020
accacagtcg gttgtgacta ttacagttag ccgtgaccga cgcagcaatt tatgatggcc   4080
gaagaacgct aggaggtatc ccttcgtgat ttcctacagc ttcctcggtg ccttctaaca   4140
aggcagctct gaatgatctc gatattgtgt agcgccacac agctaagcgg gatcggataa   4200
ctctgtgtat tctcacacgc gtaccttccg acgttcctta gcaatacatt atggcgtgcc   4260
tgataacgag cagcggtaga cgtgtaccag tacacgttga gtaagcaacg acggatggta   4320
tgttccggct caccttaatc ttgtctacat ccactcgtgc actagatgtt gtcgagcacc   4380
attaacaagg gccggtggaa ctatagtctt tcgcgactcc aatattgcca ggcgccattg   4440
tggccggatt caattaagcc tagaactaag cgaggtcgga agcctatgat gattcgcagc   4500
atgtgtcaat gcacactggc ataagattgg gcggagccaa tccgtatact cttacgcgtc   4560
aatccaattg ggcttggcca ttatgcgtag ccgcatacga gcgattggag atagccaaga   4620
agtatcagtt gacgctgacc ctggaactgt tcaaggtcac cttgtgtgag tccacacaga   4680
gatcgtcgcg agctactata ctacatgcct tcgtgcattc gaagtgaatt aggacaggcc   4740
aaccttatgg ggttccgcaa tcttagctat ctccgatcgc agtggttaag gacaaccgga   4800
gtgctaggtt acatcgaacc cgtcaccttg tactgttcca tgacggccgt cagtaattac   4860
ttcgccaccg cctattgtta ccagtcgacg ttgactagta aaggacgcac ggaagtatgt   4920
gccatgtgcg attgcacata cagagtccat tgagacttgc gaatatgcgg aggcgcataa   4980
cctgcaacct ttcatggttc aagttctagt ggacctcgac cgtacatacg tacgtgcgta   5040
atacagtgct gcgtgacatc agcgctgtgt gatatcacac tcgcaggaag ctatgaagga   5100
tatgccggtg cgcattaaca gtgcattctt acatgcctcc gtatggttat acgcaaccgc   5160
cacacagtat tgtgtgacgc agagatagag gagagcgaga ctcttgcacg tctccatgta   5220
accagttcag gttgacctga ccggcgatgt ttaatagcac cggtaacctg taacggttca   5280
cattcttatg tgcctccgca tctattcagt ctcgcctgac gtgcgcgact acatatagtc   5340
tactactcgt cgtcgtctac tggtagttcg caacgaccta gtaacaatct acggtggctc   5400
aagccgcaag ggattatgga gccagcagag attgatgaga ctctggcgtt tctcaatacc   5460
atcctaatct gcttcggctc ccaggcttgg ttgaatccaa cattcacgct tgcctgtatc   5520
aaggttgtga ggaaccacag cggaagaagg taaggaggaa gtcgatatcg actagcgcta   5580
accgaaccat gttaggttgc tattcaacgg cgcctggtaa cggtgagacg taacagagta   5640
gcacttgatg atgtccagca cttgattcat tccagcctgc aaggtgcggc ggaacataat   5700
agattaagtg gagccggaca acacgttcct gtgtaccttc gtccaagcgt acttggatac   5760
tatctccaat cgctcttggc gacggtaatg agtaacggca aagatctctg ggagctctca   5820
caggccagct tgaattgatc ttgcgtacgg ccatacgtaa gttctacgag acctcgtaga   5880
cgtgtgtctt tacacactcc aaccagccac ggttgattgt ttgtccgctg ccacttatca   5940
caacgcgttg tggtatacca ccgaatctgg ttaggctcaa cggcagtgtt taatgacacc   6000
```

```
attatccact gccgcttgtc aagacaagtt ggagtggacc cctgtagagt ttcacgagac    6060
tctcctggcg ctcttcaata aaccgagttc ggttagacct gccagtcggt attgactaac    6120
agaaggacgg gaggaagtaa acatcacaat gtgctgtggc cacgcgcatg tgtatatgca    6180
cggactgtcg taagtcacta tcctattacg cttcgccgta atgcatatgt gcatgcgcac    6240
atatctgctt gcgctcatcc tggaggcaat caagaatggc accgtcgcct gttactattc    6300
cgtggaagat tacaaggagc gaacggccag aggtaattga gcctaacgtg attcggtaca    6360
ctggttgtag tcaaccacga tctgagtgtg ctcagacaca tgaggagtgt cagaagacac    6420
cgcttgaggt tatccagaac atcaccttat gctgttccgc aattggtagg ggccaacgaa    6480
atgagcggcg gcagataata actctcgatt gtctctagcc agagcgctgg gagatatcaa    6540
tgccacaacg cattgtggta tcgccgtcgt ctattactac taattctgct cggcctcatc    6600
attaagccat gccggattgc cacaccgacg tgtgttagta tcggcacgat ctaatgtagc    6660
gttcaattgg acctgccaa cgacgaacag tagtaggtga agtgtaacg ggacacggta    6720 gtcggctctt actaatctcc ccgatcttat ttagctccgc cttgagagct tccagagatc    6780
gagttaactt agaccggtcc aactatgcat ggtcgcatgc gaagtcctcg aggacttcta    6840
tcttatagag ctccgcgaga gatccgtgtg agcttacaca ccaccggagt ttgttaagac    6900
tgaacacctg caggtgttca aatagaacgt ggcgaggtac ctatgttaag tcgcaccgga    6960
atcattggat gctgccaagc tgcgtcttcg catactccta aatctactcc ggctcgtctt    7020
gtgttacagt acaccgtgac tcttacgccg ctccgtatta tagtggcttg cgacaatcca    7080
taccaaggtt cgttggaacc accggaacgg gttaaggtaa ccgaagcgct ttaggatatc    7140
tgaagtgcag caggacatga caagctcaat tggatctggc ctcatcctgg tctgcttcaa    7200
cggccttgag taattccaga cctaaggatt ttcggaagcc gttgaggcgg accagaataa    7260
gagtctgttg agactcacca gttggccaat accaattggc tcaccgcgct ctgttatatc    7320
aggtgcgcag gaacatatga gccgttcttg attacctcca ccgcggttct ttataacctc    7380
cgatcgaatt tagctaggcc aatatgaagc ggcgcaggat tgacatgagg cagtgcagaa    7440
gccagaactt attgaggtcc gactccttcg agtcttccta ctacttagag tcgtccgaga    7500
ttcaagtatg cctggacgca cttacattgt tccgtgccac aatgaatacg ggcaggcgta    7560
cacctctctt tgttctctcc atgattccgg gcagccttaa gtatacagag acgcgtgaga    7620
gttctgtcat acctcactgc tgtcgagttg cactagacca agcggagact gataagagtc    7680
gtgatcgcgt acagctatac ttaccagatg ccgttgagca caggtataag tgaacgcgga    7740
gatagccttg agcgattcca ctggctcgtt tcaatctacc tacgcgatat cgtatagcgc    7800
aaccttcact ggttcctgtc gtgtaggacg acacgaagta tcggacgtat ctaagtacgc    7860
atagtgatag gcgacagcga agttaatgct gaccggcatc agcagcgtgg gatgatacaa    7920
cactctggag tgtctcaaga aagtggtgta ggacaacacg tataggtact cgcgaacgtc    7980
tcacgtaggt ctgtacgaac actgccgcag gtcattatga aggtggcctt gaacaattcc    8040
ttagtcggat ccgactaagc catggagcgg tgcaagataa ttgcaacgcg ccatggtata    8100
acctacaagt gttcgtggac tagctcacag cgatctgtga taggtatgtt cgaacgcacc    8160
gctctgacgg atctcagtaa agcacctgcg gatgttcata gagccactcg agattgtcta    8220
ctaccatcat tcgttgctgc cattgtacct tgccacgttc ttggcctagg ccaattcgaa    8280
agtcacgtgt gactgtacac gcttagtcag atccgactga acgaatagat gtaggcgagc    8340
atattaggct gcgccgaatc tcagctgcct ctgatcattc ccaagaggtg ttggagaaca    8400
```

```
aatccgcctt ggcttattcc aactacattg ggtcgtgcca gtcatgcaat actgcatggc    8460
cgtaggctgt tacgaatcac taaggtcgtt cggaactacc accttccgcg gttccttata    8520
gcagacacgg atgagtgtaa caatccttgt tggcttccac cgacaaggat tagtggaagc    8580
aatgtcggaa ggcactaagg gctagactat atcgagtcgc tgatgcactg cagcatgtca    8640
gcttcatatt atcctgcgcc actatgatcg gtcgcagcta tagagaccgg cgagagttaa    8700
agacgatgcg gagtagcata gacaattgag agtggccaga ccaagtaact ttggacggtc    8760
gccttcagtt attcctgacc agacctacat gagttcgtgc tcctcggact cttctaagtc    8820
actcaactag gtctggtcga ttagaccatg ccgagttgca tggttctcat caacctctgc    8880
agtgcgagtg gacatagaca atgtgactcg gcacagtcta cggctgcagt taatcatgac    8940
tacaagactt cgtggagtcc catatcttcg tgcgctccta acgagagaag gtagagagga    9000
ttacttctgg ccgtcctcaa gatactaccg agcgtcgtta aggtgtaggt gaacacgaac    9060
tggataggat caagcgaagc tatgaacttg cgcaggtcca aatcgcgtca ggctatactg    9120
agtccggagg gacttaagaa attctcacgt gcctctgtac tggtcatggt caactgcaac    9180
gtccgtcctg acttacttca gccgaggagt attagaagac tcgacgctag ctagtatcga    9240
ctgaattagt tcaggccgac cttggtctcg tccaactcta cggtcggcat taactaatgc    9300
atataatccg gcgcggctta ataaggcagt gcggaatgac aactgtcgtg ggtcactaca    9360
aggctgaacg gaatcaggta aaggaagagt ggaaggagac ccttgcctag ttccattcga    9420
ctcaagttct tctggaccte acagaattct gtgaggcctc gctaggaagt atcgaaggac    9480
atactctagg gcgtctcgaa gttccgaacg accttaggta aagagagtct ggagagactc    9540
ttcgaagagg cctaggagaa aaggcttcat ggaatcctgc tctacgaatg ctcgtaggca    9600
gatcagcact agctgatgtc ccgctccgtt ttatcttacc ttgtgtggtt ccacacaacc    9660
taggttacct cgaaccgttc aagcctaata ggattcggcg tgtacaatag cacgtggcga    9720
accgattatt gttagccgcc aagaggatga ggagaagcag tgttcgatgt cacctagcac    9780
cggttaatag taaccggcga tagcgttgct cgataccatc accatacctg gttgcgttca    9840
tgcaatgaat catggcaggc gcaggaccgt atgaagttac tctcgctaag ctctatcgga    9900
ttcagcattg cctgatgcca cacgtcagag tgtactgaga ctctcctcct tctcttcttc    9960
acggattcgg gtaagcctaa gcgaccgatg atagttagca gaatgtcagt aggcactgac   10020
gctcgcacat atctatgtgc cagacgtggt tgagtacaac acatctgagg gtgctcagaa   10080
attctagctg gcctcgatca aatgactggt ggcagtcaac tccttcgaag cttcctagga   10140
gactggagct agtcaagatc atgtcgtatt gcactacgcc aagattcgta ggagcctacg   10200
gatcgatcct agctagcttc agttcctcgg gaccttctaa aggagtcgag gaagactaga   10260
```

<210> SEQ ID NO 10
<211> LENGTH: 960
<212> TYPE: DNA
<213> ORGANISM: Artificial Sequence
<220> FEATURE:
<223> OTHER INFORMATION: Synthesized

<400> SEQUENCE: 10

```
ggatatatcc aagcgcgctt caacgagagc tggtagagat ttcggtgtga cctaacacag      60
ggtagaatta aacgaggccg tatccgaggc cgcttagaat acggtccaac gtaacttggt     120
ttatacgcga ccgcgtatag gacgtctgca agtactcatg cattaactga tgccggtcag     180
```

```
tcagattaac ctgagccggt gtgacggagc acagtaagat cactcaattc tgtctggcct      240
gaacgcaata aggtatggcg cgtacaggaa tacgtgaagg ccggttccta ttaaccttcg      300
atcagtacca gctgacgttg atacttgttc gcgtccacct tgcgcatagc catatgcgat      360
tgatggctac cagcaatcgt cacaacttaa tgtggtccgg atacatcaca gcgtgctgtg      420
acctaagacc gttcggagtt cgaatctata taggctcgcg ggcctccaag aattcttgga      480
gccaatcctc attggcttct ttagtgagtc ccgacagact tagagaatac cgagaggcgt      540
tcggcggtta ctaataaccg aggcgttcgc gaataccttat ccacgctgaa ttgtatcagg      600
ggaccagtgg aagttgacaa gcttgaacgc atccaggtat gtctcgccac actctattgt      660
cttattggcc tccgccaatt tcaatggaga ctggcaagag agagaaccta gagaggttcg      720
acttgttatc gtccaccgct tagcataacc cgatgcggtt cgctgtctca tatcactctg      780
gttggatgaa accaagcagg gcaccaccaa atgttgttgg agcctcaggc gattctgaat      840
caattctcac tggcctctgt ggcataggtg aatgcgaaca gctaatagga atcggcgaag      900
tggaccgcca caagttattg ctcgaatata tctaggcgcg gcacggtacc atgtaacgtt      960
```

<210> SEQ ID NO 11
<211> LENGTH: 960
<212> TYPE: DNA
<213> ORGANISM: Artificial Sequence
<220> FEATURE:
<223> OTHER INFORMATION: Synthesized

<400> SEQUENCE: 11

```
tgttcaccat cacctgttgc gtaggtggtg acgaacaaca acgccttgtt gtattccacc       60
tgtaaggtgg cacggaacaa ctcaacgctt tctggtatcc gagtcatagg agactgcgaa      120
agctggaatg gatcaaggca tcagtctcgt ctgactctac cgaagattct taggagcctc      180
cctctacatg ttctcgtgca gcgttggtat ataccaacgc aatagctgag gcgatcaga       240 caatataggt tggcgcgaac atggttgact gcaaccagtc tccattgccg cttgccatta      300
agcgaattag gataggccga gtgcagacag acatgagtga taaccgtaat cggttacggc      360
taccgcctcg cgttattcta ttcataaggt cctgcggaac aacactgtta ggtgtcaccg      420
acatatccag gtgcgcttga tggagtactt caagacgtcc attgcgcggt gccatataac      480
cagtggcact tgacaatgtc cgacctaacg tagttcggta gccgcactct attatgtctc      540
agaaccgagt gaggttagac gttaattacg accggccgta cctcgtgcgt ttctacatac      600
acttcaagcg gtcctggata aatcaccagc ggctgttgat caatcggctg tggctaatca      660
ttaagacaag ccggagtgga aacttatcct ggtccgcttc ctcgcttcgg tctatcctaa      720
gaacttcctt aggtccttcc tatggagatt cgcaagagcc accacgacat gttgtagtgc      780
tcatagattg ctgcgagcca cagcacggag tgatgtaaga ccgttcaagg ttacctggaa      840
aagcatcttg ggatgctcca aacagacggc ggtgagtaat ctagtgctct tcgacatctc      900
cgtctcatat tactctgcgc tcagaaggcg ctgaggaata gacaccatgt agtgttgcac      960
```

<210> SEQ ID NO 12
<211> LENGTH: 960
<212> TYPE: DNA
<213> ORGANISM: Artificial Sequence
<220> FEATURE:
<223> OTHER INFORMATION: Synthesized

<400> SEQUENCE: 12

```
agtgttgcac gacaccatgt ctgaggaata tcagaaggcg tactctgcgc cgtctcatat       60
```

```
tcgacatctc ctagtgctct ggtgagtaat aacagacggc ggatgctcca aagcatcttg    120
ttacctggaa ccgttcaagg tgatgtaaga cagcacggag ctgcgagcca tcatagattg    180
gttgtagtgc accacgacat cgcaagagcc tatggagatt aggtccttcc gaacttcctt    240
tctatcctaa ctcgcttcgg ggtccgcttc aacttatcct ccggagtgga ttaagacaag    300
tggctaatca caatcggctg ggctgttgat aatcaccagc gtcctggata acttcaagcg    360
ttctacatac cctcgtgcgt accggccgta gttaattacg gaggttagac agaaccgagt    420
attatgtctc gccgcactct tagttcggta cgacctaacg tgacaatgtc cagtggcact    480
gccatataac attgcgcggt caagacgtcc tggagtactt gtgcgcttga acatatccag    540
ggtgtcaccg aacactgtta cctgcggaac ttcataaggt cgttattcta taccgcctcg    600
cggttacggc taaccgtaat acatgagtga gtgcagacag gataggccga agcgaattag    660
cttgccatta tccattgccg gcaaccagtc atggttgact tggcgcgaac caatataggt    720
ggcgatcaga aatagctgag ataccaacgc gcgttggtat ttctcgtgca cctctacatg    780
taggagcctc cgaagattct ctgactctac tcagtctcgt gatcaaggca agctggaatg    840
agactgcgaa gagtcatagg tctggtatcc ctcaacgctt cacggaacaa tgtaaggtgg    900
gtattccacc acgccttgtt acgaacaaca gtaggtggtg cacctgttgc tgttcaccat    960
```

<210> SEQ ID NO 13
<211> LENGTH: 960
<212> TYPE: DNA
<213> ORGANISM: Artificial Sequence
<220> FEATURE:
<223> OTHER INFORMATION: Synthesized

<400> SEQUENCE: 13

```
atgtaacgtt gcacggtacc tctaggcgcg ctcgaatata caagttattg tggaccgcca     60
atcggcgaag gctaatagga aatgcgaaca ggcataggtg tggcctctgt caattctcac    120
gattctgaat agcctcaggc atgttgttgg gcaccaccaa accaagcagg gttggatgaa    180
tatcactctg cgctgtctca cgatgcggtt tagcataacc gtccaccgct acttgttatc    240
gagaggttcg agagaaccta ctggcaagag tcaatggaga tccgccaatt cttattggcc    300
actctattgt gtctcgccac atccaggtat gcttgaacgc aagttgacaa ggaccagtgg    360
ttgtatcagg ccacgctgaa gaataccgat aggcgttcgc ctaataaccg tcggcggtta    420
cgagaggcgt tagagaatac ccgacagact ttagtgagtc attggcttct gccaatcctc    480
aattcttgga ggcctccaag taggctcgcg cgaatctata gttcggagtt acctaagacc    540
gcgtgctgtg atacatcaca tgtggtccgg cacaacttaa cagcaatcgt tgatggctac    600
catatgcgat tgcgcatagc gcgtccacct atacttgttc gctgacgttg atcagtacca    660
ttaaccttcg ccggttccta tacgtgaagg cgtacaggaa aggtatggcg gaacgcaata    720
tgtctggcct cactcaattc acagtaagat gtgacggagc ctgagccggt tcagattaac    780
tgccggtcag cattaactga agtactcatg gacgtctgca ccgcgtatag ttatacgcga    840
gtaacttggt acggtccaac cgcttagaat tatccgaggc aacgaggccg ggtagaatta    900
cctaacacag ttcggtgtga tggtagagat caacgagagc aagcgcgctt ggatatatcc    960
```

<210> SEQ ID NO 14
<211> LENGTH: 960
<212> TYPE: DNA
<213> ORGANISM: Artificial Sequence
<220> FEATURE:

<223> OTHER INFORMATION: Synthesized

<400> SEQUENCE: 14

| | | | | | |
|---|---|---|---|---|---|
| ggtaccgacc | aacgttagtt | ggtctattaa | aactcgccgg | ctgtcactta | tcactgtccg | 60 |
| tatgacaatc | cgcagtggct | agtatgctac | gacgcatcgt | gcgcatgcac | atatgcatgt | 120 |
| ggagtgccga | aagacattag | tcgagccata | ctagattgcg | aggccgtgga | gaattacaag | 180 |
| ttctgtagaa | cctcacgagg | ccggtaacac | ttaacggtgt | gcaatattca | atggcgcctg | 240 |
| tggcgaaggc | caataggaat | cacagcggtc | tgtgataact | gtggtcgtca | acaactactg | 300 |
| ggctcgagag | aatctagaga | ctgcgttacc | tcataccgtt | cttaagtcga | tccggactag | 360 |
| ggccttgctc | aattccatct | agaattcgcc | gaggcctatt | ccaggcacca | ttgaatgttg | 420 |
| cgctaagtta | tatcggaccg | atacgccggc | gcgtattaat | gttacacaac | accgtgtggt | 480 |
| tacactacaa | cgtgtcgtgg | tgctactgcc | catcgtcatt | attgttcgtc | gccacctact | 540 |
| cggccgatac | taattagcgt | gcgataaggc | atagcggaat | ataggtctta | gcgaactccg | 600 |
| tggtacctaa | caacgttcgg | agtacaactc | gacgtggtct | cattggtcaa | tgccaactgg | 660 |
| ggtatgtaga | aacgcacgag | acggtcagga | gtaactgaag | tattgcgctc | cgccatatct | 720 |
| agatccatta | gagcttgccg | cttgtacacc | tccacgtgtt | gtgtgaacaa | acacaggtgg | 780 |
| ccaccaggca | ttgttgaatg | tcttgtcggc | ctccactaat | ggcaagccag | aatggattga | 840 |
| ctgttggtcc | tcaccaactt | ggtgctatat | aacatcgcgc | ggtggacgtg | aacaagtaca | 900 |
| accgttacaa | gttaccgtgg | tatgtagtca | cgcacgactg | gaagcggcac | aggataatgt | 960 |

<210> SEQ ID NO 15
<211> LENGTH: 960
<212> TYPE: DNA
<213> ORGANISM: Artificial Sequence
<220> FEATURE:
<223> OTHER INFORMATION: Synthesized

<400> SEQUENCE: 15

| | | | | | |
|---|---|---|---|---|---|
| gtggtatctg | acaacgctca | attccataag | gccttgcgga | gctcttaact | atctccggtc | 60 |
| cggatgcttg | taagcatcca | aacggtctat | ggtaactcgc | gtggacaagt | acaagtggac | 120 |
| tcctggttgt | cttcaaccac | tcgctatgag | ctatcgcaga | cattagtgcg | tgccgacata | 180 |
| agtagagccg | gacgagatta | cgtgcttgct | tacatccatc | gactgagtag | agtcagacga | 240 |
| ataatccgtg | gcggcttaca | gagaatggtt | agaggcaacc | tcacaacagt | ctgtggtgac | 300 |
| gaactgagcg | aggtcagata | aaggccacgg | ggaattgtaa | cctgaccact | ttcagttgtc | 360 |
| cgcattccgt | tatgccttac | gtattgacgt | acgccagtac | aaccatagaa | ggttgcgagg | 420 |
| ttacgcacct | ccgtatgttc | aagatacacg | ggagcgtgta | attgatactg | gccagcgtca | 480 |
| caccgatgtg | tgttagcaca | ttggcagcgt | ccaatgatac | gcataagctt | atgcggatcc | 540 |
| gcttctctgg | atcctctcaa | cacggctagt | tgtaatcgac | tgattatacg | cagccgcgta | 600 |
| tataacagct | cgcggtgatc | catagtaagg | tgcgacggaa | gagcgacgat | agatagtagc | 660 |
| ttccttacttg | cctccgtcca | ctacacatgg | tcgtgtgcaa | acttacggat | gtccgtaagc | 720 |
| acagtgtatg | gtgacacgca | ttgctctatt | ccatctcgcc | ccaaggcctt | ttggaattcc | 780 |
| taatgtgtct | cggcacactc | actcggcaat | gtctaatggc | aggatgtgct | gaagcacatc | 840 |
| tatcttgtag | cgctccacga | ttcactcact | cctgtctgtc | ccatcattag | ttgctgccga | 900 |
| atgagatcat | gcagagctgc | tgtcgctggt | cactatcaac | ctctgcagcg | tctcatgata | 960 |

<210> SEQ ID NO 16
<211> LENGTH: 960
<212> TYPE: DNA
<213> ORGANISM: Artificial Sequence
<220> FEATURE:
<223> OTHER INFORMATION: Synthesized

<400> SEQUENCE: 16

```
tctcatgata ctctgcagcg cactatcaac tgtcgctggt gcagagctgc atgagatcat      60
ttgctgccga ccatcattag cctgtctgtc ttcactcact cgctccacga tatcttgtag     120
gaagcacatc aggatgtgct gtctaatggc actcggcaat cggcacactc taatgtgtct     180
ttggaattcc ccaaggcctt ccatctcgcc ttgctctatt gtgacacgca acagtgtatg     240
gtccgtaagc acttacggat tcgtgtgcaa ctacacatgg cctccgtcca ttcttacttg     300
agatagtagc gagcgacgat tgcgacggaa catagtaagg cgcggtgatc tataacagct     360
cagccgcgta tgattatacg tgtaatcgac cacggctagt atcctctcaa gcttctctgg     420
atgcggatcc gcataagctt ccaatgatac ttggcagcgt tgttagcaca caccgatgtg     480
gccagcgtca attgatactg ggagcgtgta agatacacg ccgtatgttc ttacgcacct     540
ggttgcgagg aaccatagaa acgccagtac gtattgacgt tatgccttac cgcattccgt     600
ttcagttgtc cctgaccact ggaattgtaa aaggccacgg aggtcagata gaactgagcg     660
ctgtggtgac tcacaacagt agaggcaacc gagaatggtt gcggcttaca ataatccgtg     720
agtcagacga gactgagtag tacatccatc cgtgcttgct gacgagatta agtagagccg     780
tgccgacata cattagtgcg ctatcgcaga tcgctatgag cttcaaccac tcctggttgt     840
acaagtggac gtggacaagt ggtaactcgc aacggtctat taagcatcca cggatgcttg     900
atctccggtc gctcttaact gccttgcgga attccataag caacgctca gtggtatctg     960
```

<210> SEQ ID NO 17
<211> LENGTH: 960
<212> TYPE: DNA
<213> ORGANISM: Artificial Sequence
<220> FEATURE:
<223> OTHER INFORMATION: Synthesized

<400> SEQUENCE: 17

```
aggataatgt gaagcggcac cgcacgactg tatgtagtca gttaccgtgg accgttacaa      60
aacaagtaca ggtggacgtg aacatcgcgc ggtgctatat tcaccaactt ctgttggtcc     120
aatggattga ggcaagccag ctccactaat tcttgtcggc ttgttgaatg ccaccaggca     180
acacaggtgg gtgtgaacaa tccacgtgtt cttgtacacc gagcttgccg agatccatta     240
cgccatatct tattgcgctc gtaactgaag acggtcagga aacgcacgag ggtatgtaga     300
tgccaactgg cattggtcaa gacgtggtct agtacaactc caacgttcgg tggtacctaa     360
gcgaactccg ataggtctta atagcggaat gcgataaggc taattagcgt cggccgatac     420
gccacctact attgttcgtc catcgtcatt tgctactgcc cgtgtcgtgg tacactacaa     480
accgtgtggt gttacacaac gcgtattaat atacgccggc tatcggaccg cgctaagtta     540
ttgaatgttg ccaggcacca gaggcctatt agaattcgcc aattccatct ggccttgctc     600
tccggactag cttaagtcga tcataccgtt ctgcgttacc aatctagaga ggctcgagag     660
acaactactg gtggtcgtca tgtgataact cacagcggtc caataggaat ggcgaaggc     720
atggcgcctg gcaatattca ttaacggtgt ccggtaacac cctcacgagg ttctgtagaa     780
gaattacaag aggccgtgga ctagattgcg tcgagccata aagacattag ggagtgccga     840
```

```
atatgcatgt gcgcatgcac gacgcatcgt agtatgctac cgcagtggct tatgacaatc    900
tcactgtccg ctgtcactta aactcgccgg ggtctattaa aacgttagtt ggtaccgacc    960
```

<210> SEQ ID NO 18
<211> LENGTH: 1160
<212> TYPE: DNA
<213> ORGANISM: Artificial Sequence
<220> FEATURE:
<223> OTHER INFORMATION: Synthesized

<400> SEQUENCE: 18

```
aggaggtatc gtaccgatta tcgcgactcc cagcggtaga attgcacata accacagtcg     60
acatcgaacc ataagattgg ggaagtatgt gcgattggag cgaggtcgga ttcgccaccg    120
ccactcgtgc cttgtgtgag tcaaggtcac aggcagctct ccttcgtgat aaccttatgg    180
agctactata tggtgttatg tctcacacgc ccgtgaccga acggatggta cctgcaacct    240
gtaccttccg ttatgcgtag caccttaatc caattaagcc aattggcgcc gaatatgcgg    300
attaacaagg cagagtccat atgtgtcaat cacaatatgc aatccaattg cgaggccaag    360
agcctatgat ttcttaacca gcaatacatt agtggttaag gagatccgct ttgactagta    420
atacaagcaa aggacaggcc ctacatgcct cagtaattac actagatgtt ctccgatcgc    480
cttaccgcac cttacgcgtc ccttctaaca ggcgccattg cgcagcaatt gacgctgacc    540
gatcggataa cgtcaccttg cgtgtaccag agcgccacac ggttccgcaa ttcctacagc    600
caacaccgca gatcgtcgcg ttacagttag ctctgtgtat cctattgtta tccacacaga    660
ctggaactgt gaatgatctc ttgtctacat ccgcatacga tgttccggct ggccaatatt    720
tggccggatt acgttcctta gtaagcaacg ttcatggttc acgttagccg gccatgtgcg    780
ctatagtctt tgataacgag gaagaacgct gcggagccaa aaggacgcac atagccaaga    840
tagaactaag gttgtgacta gtgctaggtt ccgtatact tccgttatgt gtcgagcacc    900
tgacggccgt tcttagctat agctaagcgg gatattgtgt tacacgttga tactgttcca    960
aatattgcca ttcctcggtg agtatcagtt tatgatggcc tagaattgga tgtggcgcat   1020
ggcttggcca gccggtggaa aggcgcataa tgagacttgc gcacactggc gacaaccgga   1080
atggcgtgcc gcgtggatgg gaagtgaatt tcgtgcattc agagcttatc ccagtcgacg   1140
cctccggttg gattcgcagc                                               1160
```

<210> SEQ ID NO 19
<211> LENGTH: 1160
<212> TYPE: DNA
<213> ORGANISM: Artificial Sequence
<220> FEATURE:
<223> OTHER INFORMATION: Synthesized

<400> SEQUENCE: 19

```
aaccttatgg aaggacgcac aatattgcca aatccaattg aattggcgcc acatcgaacc     60
accacagtcg acgtatggta acgttagccg acgttcctta actagatgtt agagcttatc    120
agcctatgat agcgccacac agctaagcgg agctactata aggacaggcc aggaggtatc    180
aggcagctct aggcgcataa agtatcagtt agtggttaag ataagattgg atacaagcaa    240
atagccaaga atggcgtgcc atgtgtcaat attaacaagg attgcacata caacaccgca    300
caattaagcc cacatatgc caccttaatc cagagtccat cagcggtaga cagtaattac    360
ccactcgtgc ccagtcgacg ccgcatacga ccgtgaccga cctattgtta cctccggttg    420
cctgcaacct ccttcgtgat cctctaaca cgaggccaag cgaggtcgga cgcagcaatt    480
```

```
cgtcaccttg cgtgtaccag ctacatgcct ctatagtctt ctccgatcgc ctctgtgtat     540
ctggaactgt cttaccgcac cttacgcgtc cttgtgtgag gaagaacgct gaagtgaatt     600
gaatatgcgg gaatgatctc gacaaccgga gacgctgacc gagatccgct gatattgtgt     660
gatcggataa gatcgtcgcg gattcgcagc gcaatacatt gcacactggc gccatgtgcg     720
gccggtggaa gcgattggag gcggagccaa gcgtggatgg ggaagtatgt ggccaatatt     780
ggcgccattg ggcttggcca ggttccgcaa gtaagcaacg gtaccgatta gtaccttccg     840
gtcgagcacc gtgctaggtt gttgtgacta tacacgttga tactgttcca tagaactaag     900
tagaattgga tatgatggcc tcaaggtcac tccacacaga tccgtatact tccgttatgt     960
tcgcgactcc tcgtgcattc tctcacacgc tcttagctat tgacggccgt tgagacttgc    1020
tgataacgag tggccggatt tggtgttatg tgtggcgcat tgttccggct ttacagttag    1080
ttatgcgtag ttcatggttc ttcctacagc ttcctcggtg ttcgccaccg ttcttaacca    1140
ttgactagta ttgtctacat                                                1160
```

UNIVERSAL SHORT ADAPTERS FOR INDEXING OF POLYNUCLEOTIDE SAMPLES

CROSS REFERENCE TO RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

INCORPORATION BY REFERENCE OF THE SEQUENCE LISTING

This application includes a sequence listing which has been submitted electronically in ASCII format and is hereby incorporated by reference in its entirety. This ASCII copy, created on May 4, 2018, is named ILMNP023_ST25.txt and is 29,375 bytes in size.

BACKGROUND

The present disclosure relates to, among other things, sequencing of polynucleotides from multiple libraries; and more particularly to increasing the likelihood that sequencing properly identifies the library from which the polynucleotides originated.

Improvements in next-generation sequencing (NGS) technology have greatly increased sequencing speed and data output, resulting in the massive sample throughput of current sequencing platforms. Approximately 10 years ago, the Illumina Genome Analyzer was capable of generating up to 1 gigabyte of sequence data per run. Today, the Illumina NovaSeq™ Series of Systems are capable of generating up to 2 terabytes of data in two days, which represents a greater than 2000× increase in capacity.

One aspect of realizing this increased capacity is multiplexing, which adds unique sequences, called indexes, to each DNA fragment during library preparation. This allows large numbers of libraries to be pooled and sequenced simultaneously during a single sequencing run. Gains in throughput from multiplexing come with an added layer of complexity, as sequencing reads from pooled libraries need to be identified and sorted computationally in a process called demultiplexing before final data analysis. Index misassignment between multiplexed libraries is a known issue that has impacted NGS technologies from the time sample multiplexing was developed (Kircher et al., 2012, Nucleic Acids Res., Vol. 40, No. 1).

SUMMARY

The disclosed implementations concern index oligonucleotides configured to identify sources of samples in massively parallel multiplex sequencing. Also provided are methods, apparatus, systems, and computer program products for making and using the index oligonucleotides.

One aspect of the disclosure provides method for sequencing target nucleic acids derived from a plurality of samples. The method includes: (a) contacting a plurality of index polynucleotides with target nucleic acids derived from the plurality of samples to generate a plurality of index-target polynucleotides, wherein index polynucleotides contacted with target nucleic acids derived from each sample comprise an index sequence or a combination of index sequences that is uniquely associated with that sample, the index sequence or the combination of index sequences is selected from a set of index sequences, and a Hamming distance between any two index sequences of the set of index sequences is not less than a first criterion value, wherein the first criterion value is at least 2; (b) pooling the plurality of index-target polynucleotides; (c) sequencing the pooled index-target polynucleotides to obtain a plurality of index reads of index sequences and a plurality of target reads of target sequences, each target read being associated with at least one index read; and (d) using the index reads to determine the target reads' sources of samples.

In some implementations, the set of index sequences comprises a plurality of pairs of color-balanced index sequences, wherein any two bases at corresponding sequence positions of each pair of color-balanced index sequences include both (i) an adenine (A) base or a cytosine (C) base, and (ii) a guanine (G) base, a thymine (T) base, or a uracil (U) base.

In some implementations, the combination of index sequences is an ordered combination of index sequences.

In some implementations, using the index reads to determine the target reads' sources of samples includes: obtaining, for each index read, alignment scores with respect to the set of index sequences, each alignment score indicating similarity between a sequence of the index read and an index sequence of the set of index sequences; determining that a particular index read is aligned to a particular index sequence based on the alignment scores; and determining that a target read associated with the particular index read is derived from a sample uniquely associated with the particular index sequence.

In some implementations, the plurality of index polynucleotides includes a plurality of index primers including index sequences of the set of index sequences. In some implementations, each index primer further includes a flow cell amplification primer binding sequence. In some implementations, the flow cell amplification primer binding sequence includes a P5 or a P7' sequence.

In some implementations, the target nucleic acids derived from the plurality of samples include nucleic acids with universal adapters covalently attached to one or both ends. In some implementations, the contacting the plurality of index polynucleotides with the target nucleic acids derived from the plurality of samples includes: hybridizing the plurality of index primers to the universal adapters covalently attached to one or both ends of the nucleic acids; and extending the plurality of index primers to obtain a plurality of index-adapter-target polynucleotides. In some implementations, the universal adapters and the target nucleic acids are double stranded, and hybridizing the plurality of index primers to the universal adapters includes hybridizing the plurality of index primers to only one strand of the universal adapters.

In some implementations, the universal adapters include double-stranded adapters. In some implementations, the universal adapters include Y-shaped adapters. In some implementations, the universal adapters include single-stranded adapters. In some implementations, the universal adapters include hairpin adapters. In some implementations, each of the universal adapters includes, before being attached to a nucleic acid, an overhang at one end to be attached to the nucleic acid. In some implementations, each of the universal adapters includes, before being attached to a nucleic acid, a blunt end to be attached to the nucleic acid.

In some implementations, the universal adapters and the target nucleic acids are double stranded, and hybridizing the plurality of index primers to the universal adapters includes hybridizing the plurality of index primers to both strands of the universal adapters. In some implementations, a first index primer hybridized to a first strand of a particular universal adapter includes a first index sequence selected from a first subset of the set of index sequences, and a second index primer hybridized to a second strand of the particular universal adapter include a second index sequence selected from a second subset of the set of index sequences.

In some implementations, the first and the second index sequences respectively are: the nth 10-mer in SEQ ID NO: 10 and nth 10-mer in SEQ ID NO: 11 or a reverse complement of SEQ ID NO: 11; the nth 10-mer in SEQ ID NO: 12 and nth 10-mer in SEQ ID NO: 13 or a reverse complement of SEQ ID NO: 13; the nth 10-mer in SEQ ID NO: 14 and nth 10-mer in SEQ ID NO: 15 or a reverse complement of SEQ ID NO: 15; the nth 10-mer in SEQ ID NO: 16 and nth 10-mer in SEQ ID NO: 17 or a reverse complement of SEQ ID NO: 17; or the nth 10-mer in SEQ ID NO: 18 and nth 10-mer in SEQ ID NO: 19 or a reverse complement of SEQ ID NO: 19.

In some implementations, the first subset includes index sequences listed in Table 1 and the second subset includes index sequences listed in Table 2.

In some implementations, the index primers hybridized to both strands of the universal adapters include index sequences selected from the same subset of the set of index sequences. In some implementations, the subset of index sequences is selected from one of the subsets of index sequences in Table 3.

In some implementations, the method further includes, before step (a), attaching the universal adapters to one or both ends of the nucleic acids. In some implementations, the attaching includes attaching the universal adapters by transposome mediated fragmentation. In some implementations, the transposome mediated fragmentation includes: providing nucleic acid molecules obtained from the plurality of samples and a plurality of transposome complexes, wherein each transposome complex includes a transposase and two transposon end compositions including sequences of the universal adapters; and obtaining the target nucleic acids, wherein the target nucleic acids include, at one or both ends, the sequences of the universal adapters transposed from the transposon end compositions.

In some implementations, the attaching includes ligating the universal adapters to the one or both ends of the nucleic acids. In some implementations, the ligating includes enzymatic ligation or chemical ligation. In some implementations, the chemical ligation includes click-chemistry ligation.

In some implementations, the attaching is by amplification with target-specific primers including a sequence of a universal adapter.

In some implementations, the plurality of index polynucleotides includes sample-specific adapters including index sequences of the set of index sequences. In some implementations, the sample-specific adapters include adapters having two strands. In some implementations, only one strand of the sample-specific adapters includes an index sequence. In some implementations, each strand of the sample-specific adapters includes an index sequence. In some implementations, a first strand of each sample-specific adapter includes a first index sequence selected from a first subset of the set of index sequences, and a second strand of the sample-specific adapter includes a second index sequence selected from a second subset of the set of index sequences.

In some implementations, the first and the second index sequences respectively are: the nth 10-mer in SEQ ID NO: 10 and nth 10-mer in SEQ ID NO: 11 or a reverse complement of SEQ ID NO: 11; the nth 10-mer in SEQ ID NO: 12 and nth 10-mer in SEQ ID NO: 13 or a reverse complement of SEQ ID NO: 13; the nth 10-mer in SEQ ID NO: 14 and nth 10-mer in SEQ ID NO: 15 or a reverse complement of SEQ ID NO: 15; the nth 10-mer in SEQ ID NO: 16 and nth 10-mer in SEQ ID NO: 17 or a reverse complement of SEQ ID NO: 17; or the nth 10-mer in SEQ ID NO: 18 and nth 10-mer in SEQ ID NO: 19 or a reverse complement of SEQ ID NO: 19.

In some implementations, the first subset includes index sequences listed in Table 1 and the second subset includes index sequences listed in Table 2.

In some implementations, the first and second subsets are the same. In some implementations, the subset of index sequences is selected from one of the subsets of index sequences in Table 3.

In some implementations, each sample-specific adapter includes a flow cell amplification primer binding sequence. In some implementations, the flow cell amplification primer binding sequence includes a P5 sequence, a P5' sequence, a P7 sequence, or a P7' sequence.

In some implementations, the contacting the plurality of index polynucleotides with the target nucleic acids includes attaching the sample-specific adapters to the target nucleic acids by transposome mediated fragmentation. In some implementations, the transposome mediated fragmentation includes: providing nucleic acid molecules obtained from the plurality of samples; providing a plurality of transposome complexes, wherein each transposome complex includes a transposase and two transposon end compositions including sequences of the sample-specific adapters; and obtaining the target nucleic acids, wherein the target nucleic acids include, at one or both ends, the sequences of the sample-specific adapters transposed from the transposon end compositions.

In some implementations, the contacting the plurality of index polynucleotides with the target nucleic acids includes ligating the sample-specific adapters to the target nucleic acids. In some implementations, the ligating includes enzymatic ligation or chemical ligation. In some implementations the chemical ligation includes click-chemistry ligation.

In some implementations, the sample-specific adapters include Y-shaped adapters having a complementary double-stranded region and a mismatched single-stranded region. In some implementations, each strand of the sample-specific adapters includes an index sequence at the mismatched single-stranded region. In some implementations, only one strand of the sample-specific adapters includes an index sequence at the mismatched single-stranded region.

In some implementations, the sample-specific adapters include single-stranded adapters.

In some implementations, the sample-specific adapters include hairpin adapters.

In some implementations, the contacting the plurality of index polynucleotides with the target nucleic acids includes attaching the plurality of index polynucleotides to both ends of the target nucleic acids.

In some implementations, the contacting the plurality of index polynucleotides with the target nucleic acids includes attaching the plurality of index polynucleotides to only one end of the target nucleic acids.

In some implementations, the method further includes amplifying the pooled index-target polynucleotides before sequencing the pooled index-target polynucleotides.

In some implementations, the method further includes, before step (a), fragmenting nucleic acid molecules obtained from the plurality of samples to obtain the target nucleic acids. In some implementations, the fragmenting includes transposome mediated fragmentation. In some implementations, the transposome mediated fragmentation includes: providing the nucleic acid molecules and a plurality of transposome complexes, wherein each transposome complex includes a transposase and two transposon end compositions; and obtaining the target nucleic acids including, at one or both ends, sequences transposed from the transposon end compositions.

In some implementations, the fragmenting includes contacting a plurality of PCR primers targeting a sequence of interest to obtain the target nucleic acids including the sequence of interest.

In some implementations, the set of index sequences includes a plurality of non-overlapping subsets of index sequences, a Hamming distance between any two index sequences in any subset being not less than a second criterion value. In some implementations, the second criterion value is larger than the first criterion value. In some implementations, the first criterion value is 4, and the second criterion value is 5. In some implementations, the first criterion value is 3. In some implementations, the first criterion value is 4.

In some implementations, an edit distance between any two index sequences of the set of index sequences is not less than a third criterion value. In some implementations, the edit distance is a modified Levenshtein distance where end gaps are assigned no penalty. In some implementations, the third criterion value is 3. In some implementations, each index sequence of the set of index sequences has 10 bases; the first criterion value is 4; and the third criterion is 3.

In some implementations, the set of index sequences includes 10-mers in SEQ ID NO: 9.

In some implementations, each index sequence has 32 or fewer bases. In some implementations, each index sequence has 10 or fewer bases. In some implementations, each index sequence has 6 to 8 bases.

In some implementations, the set of index sequences excludes index sequences that were empirically determined to have poor performance of indexing sources of nucleic acid samples in multiplex massively parallel sequencing. In some implementations, the excluded index sequences include sequences in Table 4.

In some implementations, the set of index sequences excludes any subsequence of sequences of adapters or primers in a sequencing platform, or a reverse complement of the subsequence. In some implementations, the sequences of adapters or primers in the sequencing platform include SEQ ID NO: 1 (AGATGTGTATAAGAGACAG), SEQ ID NO: 3 (TCGTCGGCAGCGTC), SEQ ID NO: 5 (CCGAGCCCACGAGAC), SEQ ID NO: 7 (CAAGCAGAAGACGGCATACGAGAT), and SEQ ID NO: 8 (AATGATACGGCGACCACCGAGATCTACAC).

In some implementations, each index sequence of the set of index sequences has a guanine/cytosine (GC) content between 25% and 75%.

In some implementations, the set of index sequences includes at least 12 different index sequences. In some implementations, the set of index sequences includes at least 20 different index sequences. In some implementations, the set of index sequences includes at least 24, 28, 48, 80, 96, 112, or 384 different index sequences.

In some implementations, the set of index sequences excludes any homopolymers having four or more consecutive identical bases.

In some implementations, the set of index sequences excludes index sequences matching or reverse complementing one or more sequencing primer sequences. In some implementations, the sequencing primer sequences are included in the sequences of the plurality of index polynucleotides.

In some implementations, the set of index sequences excludes index sequences matching or reverse complementing one or more flow cell amplification primer sequences. In some implementations, the flow cell amplification primer sequences are included in the sequences of plurality of index polynucleotides.

In some implementations, the set of index sequences includes index sequences having an identical number of bases.

In some implementations, each index sequence of the set of index sequences has a combined number of guanine and cytosine bases not smaller than 2 and not larger than 6.

In some implementations, the plurality of index polynucleotides includes DNA or RNA.

Another aspect of the disclosure relates to a method for sequencing target nucleic acids derived from a plurality of samples. The method includes: (a) providing a plurality of double-stranded nucleic acid molecules derived from the plurality of samples; (b) providing a plurality of transposome complexes, wherein each transposome complex includes a transposase and two transposon end compositions; (c) incubating the double-stranded nucleic acid molecules with the transposome complexes to obtain double-stranded nucleic acid fragments, wherein the double-stranded nucleic acid fragments include, at one or both ends, sequences transposed from the transposon end compositions; (d) contacting a plurality of index primers with the double-stranded nucleic acid fragments to generate a plurality of index-fragment polynucleotides, wherein index primers contacted with double-stranded nucleic acid fragments derived from each sample include an index sequence or a combination of index sequences that is uniquely associated with that sample, and the index sequence or the combination of index sequences is selected from a set of index sequences; (e) pooling the plurality of index-fragment polynucleotides; (f) sequencing the pooled index-fragment polynucleotides, thereby obtaining index reads of index sequences and a plurality of target reads of target sequences, each target read being associated with at least one index read; and (g) using the index reads to determine the target reads' sources of samples.

In some implementations, a Hamming distance between any two index sequences of the set of index sequences is not less than a first criterion value, wherein the first criterion value is at least 2. In some implementations, the set of index sequences includes a plurality of pairs of color-balanced index sequences, wherein any two bases at corresponding sequence positions of each pair of color-balanced index sequences include both (i) an adenine base or a cytosine base, and (ii) a guanine base, a thymine base, or a uracil base.

In some implementations, the contacting the plurality of index primers with the double-stranded nucleic acid fragments includes: hybridizing the plurality of index primers to the sequences transposed from the transposon end compositions at one or both ends of the double-stranded nucleic acid fragments; and extending the plurality of index primers to obtain the index-fragment polynucleotides. In some implementations, the hybridizing includes hybridizing the plurality of index primers to only one strand of the double-stranded nucleic acid fragments. In some implementations, the hybridizing includes hybridizing the plurality of index primers to both strands of the double-stranded nucleic acid fragments.

In some implementations, a first index primer hybridized to a first strand of a particular double-stranded nucleic acid fragment includes a first index sequence selected from a first subset of the set of index sequences, and a second index primer hybridized to a second strand of the particular double-stranded nucleic acid fragment includes a second index sequence selected from a second subset of the set of index sequences. In some implementations, the first and the second index sequences respectively are: the nth 10-mer in SEQ ID NO: 10 and nth 10-mer in SEQ ID NO: 11 or a reverse complement of SEQ ID NO: 11; the nth 10-mer in SEQ ID NO: 12 and nth 10-mer in SEQ ID NO: 13 or a reverse complement of SEQ ID NO: 13; the nth 10-mer in SEQ ID NO: 14 and nth 10-mer in SEQ ID NO: 15 or a reverse complement of SEQ ID NO: 15; the nth 10-mer in SEQ ID NO: 16 and nth 10-mer in SEQ ID NO: 17 or a reverse complement of SEQ ID NO: 17; or the nth 10-mer in SEQ ID NO: 18 and nth 10-mer in SEQ ID NO: 19 or a reverse complement of SEQ ID NO: 19. In some implementations, the first subset includes index sequences listed in Table 1 and the second subset includes index sequences listed in Table 2.

In some implementations, the first and second subsets are the same. In some implementations, the first or second subset of index sequences is selected from one of the subsets of index sequences in Table 3.

In some implementations, the set of index sequences includes at least 6 different index sequences.

In some implementations, each index primer includes an amplification primer binding sequence.

In some implementations, the flow cell amplification primer binding sequence includes a P5 or a P7' sequence.

In some implementations, at least one of the transposome complexes includes a Tn5 transposase and a Tn5 transposon end composition.

In some implementations, at least one of the transposome complexes includes a Mu transposase and a Mu transposon end composition.

System, apparatus, and computer program products are also provided for identifying and making index oligonucleotides and determining DNA fragment sequences using the index sequences disclosed.

An additional aspect of the disclosure relates to a computer program product including a non-transitory machine readable medium storing program code that, when executed by one or more processors of a computer system, causes the computer system to implement a method for sequencing target nucleic acids derived from a plurality of samples. Said program code includes: (a) code for receiving a plurality of index reads and a plurality of target reads of target sequences obtained from target nucleic acids derived from the plurality of samples. Each target read includes a target sequence obtained from a target nucleic acid derived from a sample of the plurality of samples. Each index read includes an index sequence obtained from a target nucleic acid derived from a sample of the plurality of samples, the index sequence being selected from a set of index sequences. Each target read is associated with at least one index read. Each sample of the plurality of samples is uniquely associated with one or more index sequences of the set of index sequences. A Hamming distance between any two index sequences of the set of index sequences is not less than a first criterion value, wherein the first criterion value is at least 2. The program code also includes: (b) code for identifying, among the plurality of target reads, a subset of target reads associated with index reads aligned to at least one index sequence uniquely associated with a particular sample of the plurality of samples; and (c) code for determining a target sequence for the particular sample based on the identified subset of target reads.

In some implementations, the set of index sequences includes a plurality of pairs of color-balanced index sequences, wherein any two bases at corresponding sequence positions of each pair of color-balanced index sequences include both (i) an adenine base or a cytosine base, and (ii) a guanine base, a thymine base, or a uracil base.

In some implementations, the computer program product includes a non-transitory machine readable medium storing program code that, when executed by one or more processors of a computer system, causes the computer system to implement one or more methods above.

A further aspect of the disclosure relates to a computer system, including: one or more processors; system memory; and one or more computer-readable storage media having stored thereon computer-executable instructions that causes the computer system to implement a method for sequencing nucleic acids in a plurality of samples. The instructions includes: (a) receiving a plurality of index reads and a plurality of target reads of target sequences obtained from target nucleic acids derived from the plurality of samples. Each target read includes a target sequence obtained from a target nucleic acid derived from a sample of the plurality of samples. Each index read includes an index sequence obtained from a target nucleic acid derived from a sample of the plurality of samples, the index sequence being selected from a set of index sequences. Each target read is associated with at least one index read. Each sample of the plurality of samples is uniquely associated with one or more index sequences of the set of index sequences. Hamming distance between any two index sequences of the set of index sequences is not less than a first criterion value, wherein the first criterion value is at least 2. The instructions also includes: (b) identifying, among the plurality of target reads, a subset of target reads associated with index reads aligned to at least one index sequence uniquely associated with a particular sample of the plurality of samples; and (c) determining a target sequence for the particular sample based on the identified subset of target reads. In some implementations, the set of index sequences includes a plurality of pairs of color-balanced index sequences, wherein any two bases at corresponding sequence positions of each pair of color-balanced index sequences include both (i) an adenine base or a cytosine base, and (ii) a guanine base, a thymine base, or a uracil base.

In some implementations, the one or more computer-readable storage media has stored thereon computer-executable instructions that causes the computer system to implement one or more methods above.

Although the examples herein concern humans and the language is primarily directed to human concerns, the concepts described herein are applicable to nucleic acids from any virus, plant, animal, or other organism, and to populations of the same (metagenomes, viral populations, etc.) These and other features of the present disclosure will become more fully apparent from the following description, with reference to the figures, and the appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIG. 1G shows sequences of a target nucleic acid having double-stranded short universal adapters attached to both ends according to some implementations.

FIG. 1H shows sequences of a target nucleic acid having Y-shaped short universal adapters attached to both ends according to some implementations.

FIG. 1I shows sequences in an i7 index primer according to some implementations.

FIG. 1J shows sequences in an i5 index primer according to some implementations.

FIGS. 4A-4C schematically illustrate the multi-well plate in which index oligonucleotides can be provided and exemplary layouts of the index oligonucleotides.

DETAILED DESCRIPTION

Figure 1A:
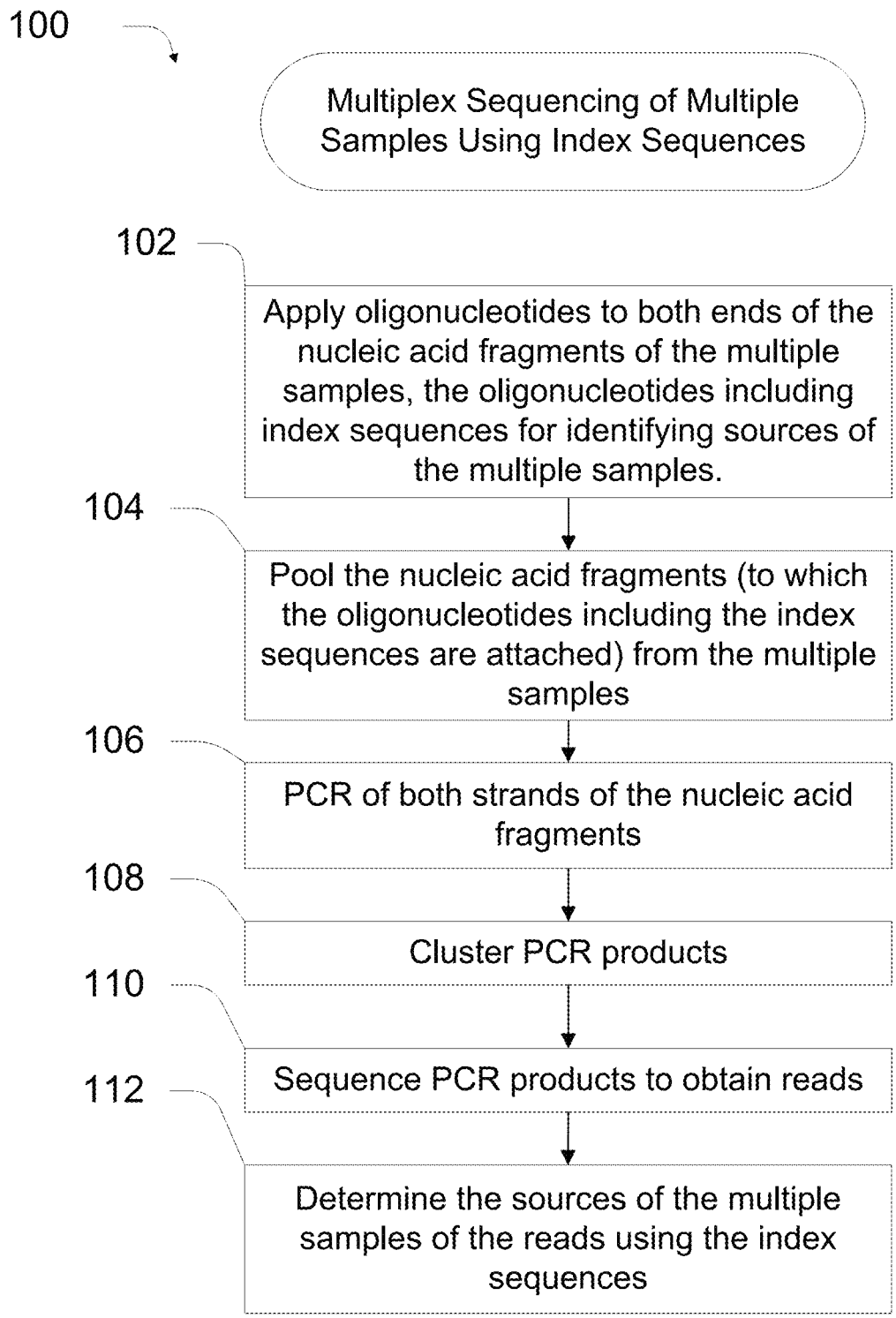
FIGS. 1A-1C illustrate example workflows using index oligonucleotides to sequence nucleic acid fragments.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

As used herein where appropriate in the context and unless otherwise specified, the word "include" encompasses the meanings of "comprise," "consist of," or "consist essentially of."

Unless otherwise indicated, nucleic acids are written left to right in 5' to 3' orientation and amino acid sequences are written left to right in amino to carboxy orientation, respectively.

Edit distance is a metric quantifying how dissimilar two strings (e.g., words) are to one another by counting the minimum number of operations required to transform one string into the other. In bioinformatics, it can be used to quantify the similarity of DNA sequences, which can be viewed as strings of the letters A, C, G and T.

Different forms of edit distance use different sets of string operations. The Levenshtein distance is a common type of edit distance. The string operations of Levenshtein distance account for numbers of deletions, insertions, and substitutions of characters in the string. In some implementations, other variants of edit distances may be used. For instance, other variants of edit distance can be obtained by restricting the set of operations. Longest common subsequence (LCS) distance is edit distance with insertion and deletion as the only two edit operations, both at unit cost. Jaro-Winkler distance can be obtained from an edit distance where only transpositions are allowed. Similarly, by only allowing substitutions, Hamming distance is obtained, which is restricted to equal-length strings. Hamming distance between two strings of equal length is the number of positions at which the corresponding symbols are different. In other words, it measures the minimum number of substitutions required to change one string into the other, or the minimum number of errors that could have transformed one string into the other.

In some implementations, different string operations can be weighted differently for an edit distance. For instance, a substitution operation may be weighted by a value of 3, while an indel may be weighted by a value of 2. In some implementations, matches of different kinds may be weighted differently. For example an A-A match might be weighted twice as much as a G-G match.

As used herein, the term "universal sequence" refers to a region of sequence that is common to two or more nucleic acid molecules, e.g., adapter-target-adapter molecules, where the molecules also have regions of sequence that differ from each other. A universal sequence that is present in different members of a collection of molecules can allow capture of multiple different nucleic acids using a population of universal capture nucleic acids that are complementary to a portion of the universal sequence, e.g., a universal extension primer binding site. Non-limiting examples of universal extension primer binding sites include sequences that are identical to or complementary to P5 and P7 primers. Similarly, a universal sequence present in different members of a collection of molecules can allow the replication or amplification of multiple different nucleic acids using a population of universal primers that are complementary to a portion of the universal sequence, e.g., a universal primer binding site. Thus a universal capture nucleic acid or a universal primer includes a sequence that can hybridize specifically to a universal sequence. Target nucleic acid molecules may be modified to attach adapters, for example, at one or both ends of the different target sequences, as described herein.

The terms "P5" and "P7" may be used when referring to amplification primers, e.g., universal primer extension primers. The terms "P5'" (P5 prime) and "P7'" (P7 prime) refer to the complement of P5 and P7, respectively. It will be understood that any suitable amplification primers can be used in the methods presented herein, and that the use of P5 and P7 are exemplary embodiments only. Uses of amplification primers such as P5 and P7 on flow cells is known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

The terms "upstream" and "5'-of" with reference to positions in a nucleic acid sequence are used interchangeably to refer to a relative position in the nucleic acid sequence that is further towards the 5' end of the sequence.

The terms "downstream" and "3'-of" with reference to positions in a nucleic acid sequence are used interchangeably to refer to a relative position in the nucleic acid sequence that is further towards the 3' end of the sequence.

One step in some implementations of the method of the present disclosure is the use of an in vitro transposition reaction to fragment and tag the target DNA to generate tagged DNA fragments. The in vitro transposition reaction requires a transposase, a transposon end composition, and suitable reaction conditions.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated in an in vitro transposition reaction. A transposase also includes integrases from retrotransposons and retroviruses.

A "transposition reaction" is a reaction wherein one or more transposon ends are inserted into a target DNA at random sites or almost random sites. In some implementations, transposition reactions cause target DNA or RNA to be fragmented at random locations. Important components in a transposition reaction are a transposase and DNA oligonucleotides that exhibit the nucleotide sequences of the transposon end, including the transferred transposon end sequence and its complement, the non-transferred transposon end sequence, as well as other components needed to form a functional transposition complex. The method of this invention is exemplified by employing a transposition complex formed by a hyperactive Tn5 transposase and a Tn5-type transposon end (Goryshin, I. and Reznikoff, W. S., *J. Biol. Chem.*, 273: 7367, 1998) or by a MuA transposase and a Mu transposon end comprising R1 and R2 end sequences (Mizuuchi, K., Cell, 35: 785, 1983; Savilahti, H, et al., *EMBO J.*, 14: 4893, 1995). However, any transposition system that is capable of inserting a transposon end in a random or in an almost random manner with sufficient efficiency to 5'-tag and fragment a target DNA for its intended purpose can be used in the present invention. Examples of transposition systems known in the art which could be applied include but are not limited to *Staphylococcus aureus* Tn552 (Colegio O R et al., *J Bacteriol.*, 183: 2384-8, 2001; Kirby C et al., *Mol Microbiol.*, 43: 173-86, 2002), Ty1 (Devine S E, and Boeke J D., *Nucleic Acids Res.*, 22: 3765-72, 1994 and International Patent Application No. WO 95/23875), Transposon Tn7 (Craig, N L, *Science*, 271: 1512, 1996; Craig, N L, Review in: *Curr Top Microbiol Immunol.*, 204: 27-48, 1996), Tn10 and IS10 (Kleckner N, et al., *Curr Top Microbiol Immunol.*, 204: 49-82, 1996), Mariner transposase (Lampe D J, et al., *EMBO J.*, 15: 5470-9, 1996), Tc1 (Plasterk R H, *Curr Top Microbiol Immunol*, 204: 125-43, 1996), P Element (Gloor, G B, *Methods Mol Biol.*, 260: 97-114, 2004), Tn3 (Ichikawa H, and Ohtsubo E., *J Biol Chem.* 265: 18829-32, 1990), bacterial insertion sequences (Ohtsubo, F and Sekine, Y, *Curr. Top. Microbiol. Immunol.* 204: 1-26, 1996), retroviruses (Brown P O, et al., *Proc Natl Acad Sci USA*, 86: 2525-9, 1989), and retrotransposon of yeast (Boeke J D and Corces V G, *Annual Rev Microbiol.* 43: 403-34, 1989).

The method for inserting a transposon end into a target sequence can be carried out in vitro using any suitable transposon system for which a suitable in vitro transposition system is available or that can be developed based on knowledge in the art. In general, a suitable in vitro transposition system for use in the methods of the present invention requires a transposase enzyme of sufficient purity, sufficient concentration, and sufficient in vitro transposition activity and a transposon end with which the transposase forms a functional complex with the respective transposase that is capable of catalyzing the transposition reaction. Suitable transposon end sequences that can be used in the invention include but are not limited to wild-type, derivative or mutant transposon end sequences that form a complex with a transposase chosen from among a wild-type, derivative or mutant form of the transposase. Exemplary transposases include wild-type or mutant forms of Tn5 transposase and MuA transposase (although EZ-Tn5 transposase was significantly more efficient than an equivalent protein amount of MuA transposase in generating 5'-tagged DNA fragments in the methods of the present invention), but any other transposase for which compositions and conditions for efficient in vitro transposition of defined transposon ends are known or subsequently developed can be used in the present methods. Transposon end sequences recognized by wild-type or mutant forms of Tn5 transposase or MuA transposase are suitable in some implementation, and those transposon end sequences that result in the highest transposition efficiencies when complexed with the transposase, together with the corresponding optimally active transposase enzymes that complex with them, are advantageous for some embodiments. In some implementation, a transposon is chosen wherein the transposase end sequence required by the transposase for transposition is not too large and the transposon end sequences are of the minimal size possible that function well for the intended purpose and that are of sufficient size so that the same sequence is present only rarely or is not present at all, in the target DNA or sample DNA. By way of example, the transposon end sequences of the Tn5-derived EZ-Tn5™ transposon end sequences comprise only 19 nucleotides, whereas some other transposases require much larger end sequences for transposition (e.g., MuA transposase required transposon end sequences of approximately 51 nucleotides).

Suitable in vitro transposition systems that can be used to insert a transposon end into a target nucleic acid include, but are not limited to, those that use the EZ-Tn5™ hyperactive Tn5 Transposase available from EPICENTRE Technologies, Madison, Wis., or the HyperMu™ Hyperactive MuA Transposase from EPICENTRE or another MuA Transposase, such as that available from Finnzymes Oy, Espoo, Finland.

In some embodiments, the insertion of a transposon end into target DNA according to the present invention can also be carried out in vivo. If transposition is carried out in vivo, transposition into the target DNA is preferably achieved by electroporating a synaptic complex of a transposase and a suitable transposon end composition into the host cell as described in U.S. Pat. No. 6,159,736 (herein incorporated by reference). This transposition method is exemplified by employing a transposition complex formed by a hyperactive Tn5 transposase and a suitable Tn5-type transposon end composition using methods similar to those described by (Goryshin, I. and Reznikoff, W. S. (J. Biol. Chem., 273: 7367, 1998) or a transposition complex formed by HyperMu™ Hyperactive MuA Transposase (EPICENTRE, Madison, Wis.) and a suitable MuA transposon end composition that exhibits the R1 and R2 end sequences recognized by the transposase. Suitable synaptic complexes or "Transposome™ complexes (EPICENTRE) between a transposon end composition and a transposase can be made as described in U.S. Pat. No. 6,159,736 and related patents of Goryshin and Reznikoff, or as described in product literature for Tn5-type EZ-Tn5™ Transposome™ complexes or for HyperMu™ MuA Transposome™ complexes from EPICENTRE Technologies, Madison, Wis.

The term "transposon end" means a double-stranded DNA that exhibits only the nucleotide sequences (the "transposon end sequences") that are necessary to form the complex with the transposase or integrase enzyme that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred transposon end sequence" or "transferred strand" and a "non-transferred transposon end sequence," or "non transferred strand" For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows:

5' AGATGTGTATAAGAGACAG 3' (SEQ ID NO: 1)

and a non-transferred strand that exhibits a "non-transferred transposon end sequence" as follows:

5' CTGTCTCTTATACACATCT 3' (SEQ ID NO: 2)

The nomenclature "pMETS" refers to the 19-base 5'-phosphate-containing single-stranded transposon end oligonucleotide that exhibits the EZ-Tn5Tm transposon end sequence:

5' pAGATGTGTATAAGAGACAG 3' (SEQ ID NO: 1)

The nomenclature "METS" refers to the 19-base single-stranded transposon end oligonucleotide that exhibits the EZ-Tn5Tm transposon end sequence:

5' AGATGTGTATAAGAGACAG 3' (SEQ ID NO: 1)

The nomenclature "pMENTS" refers to the 19-base 5'-phosphate-containing single-stranded transposon end oligonucleotide that exhibits the EZ-Tn5Tm transposon end sequence:

5' pCTGTCTCTTATACACATCT 3' (SEQ ID NO: 2)

The nomenclature "pMEDS" refers to the 19-basepair double-stranded EZ-Tn5™ transposon end wherein both 5'-ends contain phosphates:

5' pAGATGTGTATAAGAGACAG 3' (SEQ ID NO: 1)
3' TCTACACATATTCTCTGTCp 5' (SEQ ID NO: 2)

The pMEDS EZ-Tn5TM transposon end is made by annealing the pMETS transposon end oligonucleotide to the pMENTS transposon end oligonucleotide.

The nomenclature "MEDS" refers to the 19-basepair double-stranded EZ-Tn5Tm transposon end wherein only the non-transferred strand (pMENTS) contains a 5'-phosphate:

5' AGATGTGTATAAGAGACAG 3' (SEQ ID NO: 1)
3' TCTACACATATTCTCTGTCp 5' (SEQ ID NO: 2)

The MEDS EZ-Tn5™ transposon end is made by annealing the METS transposon end oligonucleotide to the pMENTS transposon end oligonucleotide.

The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some implementations, the transferred strand and non-transferred strand are covalently joined. For example, in some implementations, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure.

A "transposon end composition" means a composition comprising a transposon end (i.e., the minimum double-stranded DNA segment that is capable of acting with a transposase to undergo a transposition reaction), optionally plus additional sequence or sequences, 5'-of the transferred transposon end sequence and/or 3'-of the non-transferred transposon end sequence. For example, a transposon end attached to a tag is a "transposon end composition." In some implementations, the transposon end composition comprises or consists of two transposon end oligonucleotides consisting of the "transferred transposon end oligonucleotide" or "transferred strand" and the "non-transferred strand end oligonucleotide," or "non-transferred strand" which, in combination, exhibit the sequences of the transposon end, and in which one or both strand comprise additional sequence."

The terms "transferred transposon end oligonucleotide" and "transferred strand" are used interchangeably and refer to the transferred portion of both "transposon ends" and "transposon end compositions," i.e., regardless of whether the transposon end is attached to a tag or other moiety. Similarly, the terms "non-transferred transposon end oligonucleotide" and "non-transferred strand" are used interchangeably and refer to the non-transferred portion of both "transposon ends" and "transposon end compositions." In some implementations, a transposon end composition is a "hairpin transposon end composition."

As used herein, a "hairpin transposon end composition." means a transposon end composition consisting of a single oligodeoxyribonucleotide that exhibits a non-transferred transposon end sequence at its 5'-end, a transferred transposon end sequence at its 3'-end, and an intervening arbitrary sequence between the non-transferred transposon end sequence and the transferred transposon end sequence that is sufficiently long to allow intramolecular stem-loop formation, such that the transposon end portion can function in a transposition reaction. In some implementations, the 5'-end of the hairpin transposon end composition has a phosphate group in the 5'-position of the 5'-nucleotide. In some implementations, the intervening arbitrary sequence between the non-transferred transposon end sequence and the transferred transposon end sequence of a hairpin transposon end composition provides a tag (e.g., including one or more tag domains) for a particular use or application.

In some implementations, the methods of the present disclosure produce tagged circular ssDNA fragments. In some implementations, tagged circular ssDNA fragments exhibit only the sequence of the transferred strand of the transposon end composition, and the tagged circular ssDNA fragments do not exhibit the sequence of the non-transferred strand of the transposon end composition.

In some embodiments, the transposon end oligonucleotides used in the method of the present invention exhibit only the transposon end sequences needed in a transposition reaction. However, in some embodiments, at least one of the transposon end oligonucleotides additionally exhibits one or more other nucleotide sequences 5'-of the transposon end sequence. Thus, in some embodiments, the method uses a transferred strand that has a 3' portion and a 5' portion, wherein the 3' portion exhibits the transferred transposon end sequence and the 5' portion exhibits one or more additional sequences that do not participate in forming a functional complex with the transposase. There is no limit to which additional sequences are used for the one or more additional sequences in the 5'-portion of the transferred strand, which sequences can be used to accomplish any desired purpose. For example, in some embodiments, the 5' portion of the transferred strand exhibits one or more additional tag sequences. In some implementations, the tag sequence can be an index sequence associated with a specific sample. In some implementations, the tag sequence permits capture by annealing to a specific sequence on a surface. In some implementations, the tag sequence allows a 5' tagged target fragment to be captured on a flow cell substrate for next-generation sequencing; e.g., a P5 or a P7' tag for capture on a flow cell of an Illumina sequencing platform, or a 454A or 454B tag sequence for capture on the bead for sequencing using a Roche 454 Next-Gen sequencer.

In some implementations, the tag sequence can be one or more sequences for identification, detection (e.g., fluorescent detection), or sorting of the products of the method. In some other embodiments, the 5' portion of the transferred strand exhibits one or more additional nucleotides or sequences or a chemical group or moiety that comprises or consists of an affinity-binding that (e.g., a tag sequence that permits capture by annealing to a specific sequence on a surface, such as a bead or a probe on a microchip or array. In some preferred embodiments, the size of the one or more additional sequences in the 5'-portion of the transferred strand are minimized in order to minimize the probability or frequency of insertion of the transferred strand into itself during the in vitro transposase reaction. For example, in some embodiments, the size of the 5'-portion of the transferred strand is less than about 150 nucleotides, less than about 100 nucleotides, less than about 75 nucleotides, less than about 50 nucleotides, less than about 25 nucleotides, or less than about 15 nucleotides.

In some embodiments, the 5'-end of the transferred strand has a 5'-monophosphate group. In some embodiments, both, the transferred strand and the non-transferred strand have a 5'-monophosphate group. In some preferred embodiments, only the 5'-end of the non-transferred strand has a 5'-monophosphate group. In some other embodiments, there is no 5'-monophosphate group on the 5'-end of the transferred strand.

In some implementations, the transposon end composition used in the method of the present disclosure comprises transposon end oligonucleotides that exhibit only the transposon end sequences that form a complex with the transposase or integrase and that are needed for the transposition reaction; in these implementations, the tag in the tagged circular ssDNA fragments generated using the method exhibits only the transferred transposon end sequence. However, in some implementations, the transposon end composition comprises or consists of at least one transposon end oligonucleotide that exhibits one or more other nucleotide sequences in addition to the transposon end sequences. Thus, in some implementations, the transposon end composition comprises a transferred strand that exhibits one or more other nucleotide sequences 5'-of the transferred transposon end sequence, which one or more other nucleotide sequences are also exhibited by the tag. Thus, in addition to the transferred transposon end sequence, the tag can have one or more other tag portions or tag domains.

As used herein, a "tag" is nucleic acid sequence that is or can be associated with one or more nucleic acid molecules.

As used herein, a "tag portion" or a "tag domain" means a portion or domain of a tag that exhibits a sequence for a desired intended purpose or application. One tag portion or tag domain is the "transposon end domain," which tag portion or tag domain exhibits the transferred transposon end sequence. In some implementations wherein the transferred strand also exhibits one or more other nucleotide sequences 5'-of the transferred transposon end sequence, the tag also has one or more other "tag domains" in said 5'-portion, each of which tag domains is provided for any desired purpose. For example, some implementations of the disclosure comprise or consist of a transposon end composition that comprises or consists of: (i) a transferred strand that exhibits one or more sequences 5'-of the transferred transposon end sequence that comprises or consists of a tag domain selected from among one or more of a sample-specific index sequence, a primer binding sequence, a restriction site tag domain, a capture tag domain, a sequencing tag domain, an amplification tag domain, a detection tag domain, and a transcription promoter domain; and (ii) a non-transferred strand that exhibits the non-transferred transposon end sequence. The disclosure comprises implementations of the method that use any one or more of said transposon end compositions.

In some implementations, the transposon end composition includes a transferred strand comprising a primer binding sequence that is reverse complementary to a sequence in a PCR primer. In some implementations, the PCR primer is an index primer that includes a sample-specific index sequence. In some implementations, after the transferred strand is transposed and attached to a target polynucleotide, the sample-specific index primer is hybridized to the primer binding sequence in the transfer strand attached to the target polynucleotide.

As used herein, a "restriction site tag domain" or "restriction site domain" means a tag domain that exhibits a sequence for the purpose of facilitating cleavage using a restriction endonuclease. For example, in some implementations, the restriction site domain is used to generate di-tagged linear ssDNA fragments. In some implementations, the restriction site domain is used to generate a compatible double-stranded 5'-end in the tag domain so that this end can be ligated to another DNA molecule using a template-dependent DNA ligase. In some preferred implementations, the restriction site domain in the tag exhibits the sequence of a restriction site that is present only rarely, if at all, in the target DNA (e.g., a restriction site for a rare-cutting restriction endonuclease such as NotI or AscI). In some preferred implementations, the restriction site in the restriction site domain is for a type II restriction endonuclease, such as FokI restriction endonuclease.

In some implementations wherein the transferred strand of the transposon end composition comprises one or more restriction site domains 5'-of the transferred transposon end sequence, the method further comprises: annealing an oligodeoxyribonucleotide that is complementary to the single-stranded restriction site of the tagged circular ssDNA fragments and then cleaving the tagged circular ssDNA fragments at the restriction site using the restriction endonuclease that recognizes the restriction site. Thus, in some implementations, the method comprises linearizing the tagged circular ssDNA fragments to generate di-tagged linear ssDNA fragments.

In some other implementations wherein the transferred strand of the transposon end composition comprises one or more restriction site domains 5'-of the transferred transposon end sequence, the transferred strand of the transposon end composition comprises a double-stranded hairpin comprising the restriction site, and the method further comprises the steps of cleaving the tagged linear ssDNA fragments at the restriction site using the restriction endonuclease that recognizes the restriction site; however, in some implementations, this method is not preferred because the double-stranded hairpin provides a site of dsDNA into which the transposon end composition can be transposed by the transposase or integrase.

In some preferred implementations comprising (i) generating a double-stranded restriction site, either by annealing of an oligodeoxyribonucleotide that is complementary to the single-stranded restriction site, or by using a transferred strand that comprises a double-stranded hairpin, and (ii) then cleaving the restriction site using the restriction endonuclease that recognizes the double-stranded restriction site, the method further comprises the step of ligating the restriction endonuclease-cleaved tagged linear ssDNA fragments to another DNA molecule that has a compatible 3'-end.

As used herein, a "capture tag domain" or a "capture tag" means a tag domain that exhibits a sequence for the purpose of facilitating capture of the ssDNA fragment to which the tag domain is joined (e.g., to provide an annealing site or an affinity tag for a capture of the tagged circular ssDNA fragments or the di-tagged linear ssDNA fragments on a bead or other surface, e.g., wherein the annealing site of the tag domain sequence permits capture by annealing to a specific sequence which is on a surface, such as a probe on a bead or on a microchip or microarray or on a sequencing bead). In some implementations, a "capture tag" comprises a flow cell amplification primer binding sequence. In some implementations, the flow cell amplification primer binding sequence comprises a P5 or a P7' sequence. In some implementations of the method, after the tagged circular ssDNA fragments or the di-tagged linear ssDNA fragments are captured by annealing to a complementary probe on a surface, the capture tag domain provides a site for priming DNA synthesis using said tagged circular ssDNA fragments or said di-tagged linear ssDNA fragments (or the complements of said tagged circular ssDNA fragments or di-tagged linear ssDNA fragments) as templates. In some other implementations, the capture tag domain comprises a 5'-portion of the transferred strand that is joined to a chemical group or moiety that comprises or consists of an affinity binding molecule (e.g., wherein the 5'-portion of the transferred strand is joined to a first affinity binding molecule, such as biotin, streptavidin, an antigen, or an antibody that binds the antigen, that permits capture of the circular tagged ssDNA fragments or the di-tagged linear ssDNA fragments on a surface to which a second affinity binding molecule is attached that forms a specific binding pair with the first affinity binding molecule).

As used herein, a "sequencing tag domain", a "sequencing tag", or a "sequencing primer binding sequence" means a sequence for facilitating sequencing of the ssDNA fragment to which the tag is joined (e.g., to provide a priming site for sequencing by synthesis, or to provide annealing sites for sequencing by ligation, or to provide annealing sites for sequencing by hybridization). For example, in some implementations, the sequencing tag domain or sequencing primer binding sequence provides a site for priming DNA synthesis of said ssDNA fragment or the complement of said ssDNA fragment. In some implementations, the sequencing tag domain or sequencing primer binding sequence comprises an SBS3, SBS8', SBS12', or SBS491' sequence.

As used herein, an "amplification tag domain" means a tag domain that exhibits a sequence for the purpose of facilitating amplification of a nucleic acid to which said tag is appended. For example, in some implementations, the amplification tag domain provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction).

As used herein, a "detection tag domain" or a "detection tag" means a tag domain that exhibits a sequence or a detectable chemical or biochemical moiety for the purpose of facilitating detection of the tagged circular ssDNA fragments or the di-tagged linear ssDNA fragments (e.g., wherein the sequence or chemical moiety comprises or is joined to a detectable molecule; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate); a detectable protein, e.g., a green fluorescent protein; and an affinity-binding molecule that is bound to a detectable moiety or that can form an affinity binding pair or a specific binding pair with another detectable affinity-binding molecule; or any of the many other detectable molecules or systems known in the art).

As used herein, a "transcription promoter domain" or a "promoter domain" means a tag domain that exhibits a sequence for a sense promoter sequence or for an anti-sense promoter sequence of an RNA polymerase promoter.

As used herein, a "DNA fragment" means a portion or piece or segment of a target DNA that is cleaved from or released or broken from a longer DNA molecule such that it is no longer attached to the parent molecule. A DNA fragment can be double-stranded (a "dsDNA fragment") or single-stranded (a "ssDNA fragment"), and the process of generating DNA fragments from the target DNA is referred to as "fragmenting" the target DNA. In some preferred embodiments, the method is used to generate a "DNA fragment library" comprising a collection or population of tagged DNA fragments.

As used herein, "target DNA" refers to any DNA of interest that is subjected to processing, e.g., for generating a library of tagged DNA fragments (e.g., 5'- and 3'-tagged or di-tagged linear ssDNA or dsDNA fragments or tagged circular ssDNA fragments).

"Target DNA" can be derived from any in vivo or in vitro source, including from one or multiple cells, tissues, organs, or organisms, whether living or dead, or from any biological or environmental source (e.g., water, air, soil). For example, in some embodiments, the target DNA comprises or consists of eukaryotic and/or prokaryotic dsDNA that originates or that is derived from humans, animals, plants, fungi, (e.g., molds or yeasts), bacteria, viruses, viroids, *mycoplasma*, or other microorganisms. In some embodiments, the target DNA comprises or consists of genomic DNA, subgenomic DNA, chromosomal DNA (e.g., from an isolated chromosome or a portion of a chromosome, e.g., from one or more genes or loci from a chromosome), mitochondrial DNA, chloroplast DNA, plasmid or other episomal-derived DNA (or recombinant DNA contained therein), or double-stranded cDNA made by reverse transcription of RNA using an RNA-dependent DNA polymerase or reverse transcriptase to generate first-strand cDNA and then extending a primer annealed to the first-strand cDNA to generate dsDNA. In some embodiments, the target DNA comprises multiple dsDNA molecules in or prepared from nucleic acid molecules (e.g., multiple dsDNA molecules in or prepared from genomic DNA or cDNA prepared from RNA in or from a biological (e.g., cell, tissue, organ, organism) or environmental (e.g., water, air, soil, saliva, sputum, urine, feces) source. In some embodiments, the target DNA is from an in vitro source. For example, in some embodiments, the target DNA comprises or consists of dsDNA that is prepared in vitro from single-stranded DNA (ssDNA) or from single-stranded or double-stranded RNA (e.g., using methods that are well-known in the art, such as primer extension using a suitable DNA-dependent and/or RNA-dependent DNA polymerase (reverse transcriptase). In some embodiments, the target DNA comprises or consists of dsDNA that is prepared from all or a portion of one or more double-stranded or single-stranded DNA or RNA molecules using any methods known in the art, including methods for: DNA or RNA amplification (e.g., PCR or reverse-transcriptase-PCR (RT-PCR), transcription-mediated amplification methods, with amplification of all or a portion of one or more nucleic acid molecules); molecular cloning of all or a portion of one or more nucleic acid molecules in a plasmid, fosmid, BAC or other vector that subsequently is replicated in a suitable host cell; or capture of one or more nucleic acid molecules by hybridization, such as by hybridization to DNA probes on an array or microarray (e.g., by "sequence capture"; e.g., using kits and/or arrays from ROCHE NIMBLEGEN, AGILENT, or FEBIT).

In some embodiments, "target DNA" means dsDNA or ssDNA that is prepared or modified (e.g., using various biochemical or molecular biological techniques) prior to being used for generating a library of tagged DNA fragments (e.g., 5'- and 3'-tagged or di-tagged linear ssDNA or dsDNA fragments or tagged circular ssDNA fragments).

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, the term "polymerase chain reaction" ("PCR") refers to the method of Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of 32P-labeled deoxynucleotide triphosphates into the amplified target sequence).

As used herein, the term "primer" and its derivatives refer generally to any polynucleotide that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide.

In various implementations, a primer has a free 3'-OH group that can be extended by a nucleic acid polymerase. For a template-dependent polymerase, generally at least the 3'-portion of the primer oligo is complementary to a portion of a template nucleic acid, to which the oligo "binds" (or "complexes," "anneals," or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Template-dependent DNA polymerases (including reverse transcriptases) generally require complexing of an oligonucleotide primer to a single-stranded template to initiate DNA synthesis ("priming"), but RNA polymerases generally do not require a primer for synthesis of RNA that is complementary to a DNA template (transcription).

A "template" is a nucleic acid molecule that is being copied by a nucleic acid polymerase, such as a DNA polymerase. Whether the nucleic acid molecule comprises two strands (i.e., is "double-stranded") or only one strand (i.e., is "single-stranded"), the strand of said nucleic acid molecule that serves to specify the sequence of nucleotides exhibited by a nucleic acid that is synthesized is the "template" or "the template strand." The nucleic acid synthesized by the nucleic acid polymerase is complementary to the template. Both RNA and DNA are always synthesized in the 5'-to-3' direction, beginning at the 3'-end of the template strand, and the two strands of a nucleic acid duplex always are aligned so that the 5' ends of the two strands are at opposite ends of the duplex (and, by necessity, so then are the 3' ends). A primer is required for both RNA and DNA templates to initiate synthesis by a DNA polymerase, but a primer is not required to initiate synthesis by a DNA-dependent RNA polymerase, which is usually called simply an "RNA polymerase."

The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. In some context, the term "polynucleotide" may refer to nucleotide polymers having a relatively large number of nucleotide monomers, while the term "oligonucleotide" may refer to nucleotide polymers having a relative small number of nucleotide monomers. However, that distinction does not apply herein unless specified. Instead, the terms "polynucleotide" and "oligonucleotide" should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

In addition, the terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules. The term "polynucleotide" includes, without limitation, single- and double-stranded polynucleotides.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and E. coli DNA ligase.

As used herein, the term "adapter" refers generally to any linear oligonucleotide that can be ligated to a nucleic acid molecule, thereby generating nucleic acid products that can be sequenced on a sequencing platform such as various Illumina sequencing platforms. In some embodiments, adapters include two reverse complementary oligonucleotides forming a double-stranded structure. In some embodiments, an adapter includes two oligonucleotides that are complementary at one portion and mismatched at another portion, forming a Y-shaped or fork-shaped adapter that is double stranded at the complementary portion and has two floppy overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" is used to refer to an adapter having two strands that are fully complementary, substantially (e.g., more than 90% or 95%) complementary, or partly complementary.

In some implementations, adapters include sequences that bind to sequencing primers (e.g., SEQ ID NO: 3 and SEQ ID NO: 5). In some implementations, adapters include sequences that bind to flow cell oligos, such as SEQ ID NO: 7 and SEQ ID NO: 8 (P7 and P5 sequences) or reverse complements thereof.

In some embodiments, the adapter is substantially non-complementary to the 3' end or the 5' end of any target sequence present in the sample. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include an index sequence (also referred to as barcode or tag) to assist with downstream error correction, identification or sequencing.

The term "universal adapter" is used to refer to an adapter of a plurality of sequencing adapters having one or more universal sequences. The plurality of sequencing adapters is configured to be attached to (e.g., by ligation, hybridization, or transposition) target nucleic acids to provide adapter-target polynucleotides in a sequencing process for determining sequences of the target nucleic acids. In some implementations, all universal adapters in a sequencing process are identical, and can be attached to target nucleic acids having different characteristics, such as different sample sources, different organisms, different cell types, etc. In a sequencing process, oligos or polynucleotides (e.g., primers) having different index sequences are attached to universal adapters before, during, or after the universal adapters are attached to target nucleic acids. In some implementations, a unique index sequence or a unique combination of index sequences is applied to and associated with nucleotides having a same characteristic (e.g., a same source, a same organism, or a same cell type). When target nucleic acids having different characteristics are combined/pooled in a sequence reaction in the sequencing process, the index sequences provide a mechanism to ascertain or index the characteristics of the target nucleic acids.

Index sequences that are used to index sample sources are sample-specific sequences. Adapters including sample-specific index sequences are sample-specific adapters, as opposed to universal adapters. In the literature, some researchers use universal adapter in cases where the adapter is applied to more than one type of prepared library, and the "universal" adapter still has a sample-specific index. Unless so specified, that definition of "universal adapter" is not applicable herein.

The term "flowcell" or "flow cell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

The term "paired end reads" refers to reads obtained from paired end sequencing that obtains one read from each end of a nucleic fragment. Paired end sequencing involves fragmenting DNA into sequences called inserts. In some protocols such as some used by Illumina, the reads from shorter inserts (e.g., on the order of tens to hundreds of bp) are referred to as short-insert paired end reads or simply paired end reads. In contrast, the reads from longer inserts (e.g., on the order of several thousands of bp) are referred to as mate pair reads. In this disclosure, short-insert paired end reads and long-insert mate pair reads may both be used and are not differentiated with regard to the process for determining sequences of DNA fragments. Therefore, the term "paired end reads" may refer to both short-insert paired end reads and long-insert mate pair reads, which are further described herein after. In some embodiments, paired end reads include reads of about 20 bp to 1000 bp. In some embodiments, paired end reads include reads of about 50 bp to 500 bp, about 80 bp to 150 bp, or about 100 bp.

As used herein, the terms "alignment" and "aligning" refer to the process of comparing a read to a reference sequence and thereby determining whether the reference sequence contains the read sequence. An alignment process, as used herein, attempts to determine if a read can be mapped to a reference sequence, but does not always result in a read aligned to the reference sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13.

Of course, alignment tools have many additional aspects and many other applications in bioinformatics that are not described in this application. For instance, alignments can also be used to determine how similar two DNA sequences from two different species are, thus providing a measure of how closely related they are on an evolutionary tree.

In some cases, an alignment additionally indicates a location in the reference sequence where the read maps to. For example, if the reference sequence is the whole human genome sequence, an alignment may indicate that a read is present on chromosome 13, and may further indicate that the read is on a particular strand and/or site of chromosome 13. In some scenarios, alignment tools are imperfect, in that a) not all valid alignments are found, and b) some obtained alignments are invalid. This happens due to various reasons, e.g., reads may contain errors, and sequenced reads may be different from the reference genome due to haplotype differences. In some applications, the alignment tools include built-in mismatch tolerance, which tolerates certain degrees of mismatch of base pairs and still allow alignment of reads to a reference sequence. This can help to identify valid alignment of reads that would otherwise be missed.

The term "mapping" used herein refers to assigning a read sequence to a larger sequence, e.g., a reference genome, by alignment.

The term "test sample" herein refers to a sample, typically derived from a biological fluid, cell, tissue, organ, or organism, that includes a nucleic acid or a mixture of nucleic acids having at least one nucleic acid sequence that is to be analyzed. Such samples include, but are not limited to sputum/oral fluid, amniotic fluid, blood, a blood fraction, or fine needle biopsy samples, urine, peritoneal fluid, pleural fluid, and the like. Although the sample is often taken from a human subject (e.g., a patient), the assays can be used for samples from any mammal, including, but not limited to dogs, cats, horses, goats, sheep, cattle, pigs, etc., as well as mixed populations, as microbial populations from the wild, or viral populations from patients. The sample may be used directly as obtained from the biological source or following a pretreatment to modify the character of the sample. For example, such pretreatment may include preparing plasma from blood, diluting viscous fluids, and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "read" refers to a sequence read from a portion of a nucleic acid sample. Typically, though not necessarily, a read represents a short sequence of contiguous base pairs in the sample. The read may be represented symbolically by the base pair sequence in A, T, C, and G of the sample portion, together with a probabilistic estimate of the correctness of the base (quality score). It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 20 bp) that can be used to identify a larger sequence or region, e.g., that can be aligned and mapped to a chromosome or genomic region or gene.

The terms "site" and "alignment location" are used interchangeably to refer to a unique position (i.e. chromosome ID, chromosome position and orientation) on a reference genome. In some embodiments, a site may be a residue's, a sequence tag's, or a segment's position on a reference sequence.

As used herein, the term "reference genome" or "reference sequence" refers to any particular known genetic sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. However, it is understood that "complete" is a relative concept, because even the gold-standard reference genome is expected to include gaps and errors.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

Introduction and Context

Next generation sequencing (NGS) technology has developed rapidly, providing new tools to advance research and science, as well as healthcare and services relying on genetic and related biological information. NGS methods are performed in a massively parallel fashion, affording increasingly high speed for determining biomolecules sequence information. Index sequences have been used in the art to tag or identify sources of samples for multiplex NGS sequencing. However, many of the NGS methods and associated sample manipulation techniques introduce errors such that the resulting sequences have relatively high error rate, ranging from one error in a few hundred base pairs to one error in a few thousand base pairs. When such errors occur in the reads of sample index sequences, the reads cannot be correctly associated with the source of the sample and may cause erroneous association between reads and sources of samples.

One source of sequencing error relates to index hopping. Index hopping or jumping is observed when sequenced DNA library molecules contain a different index sequence than was present in the library adapter during library preparation. Index hopping can occur during sample preparation or during cluster amplification of pooled multiplexed libraries. One mechanism that causes index hopping involves the presence of free unligated adapter molecules present after library preparation.

Without intending to be limited by theory, the problem of index jumping has multiple modes, some of which involve the presence of residual unligated adapter molecules left over from library preparation. One class of index jumping can be caused by free unligated adapter molecules having a specific universal primer extension sequence, e.g., P7', present in the library pool, that can contribute to the formation of libraries with swapped indices. This problem can be prevented by use of a 5' exonuclease that specifically targets the P7' adapter strand for degradation. Such measures address index hopping using a biochemical approach. Some implementations correct for index hopping using bioinformatics approaches as further described hereinafter.

Some sequencing platforms use one color (e.g., a green laser) to sequence two base types (e.g., G/T) and another color (e.g., red laser) to sequence two other base types (e.g., A/C). On some of these platforms, at each cycle, at least 1 of 2 nucleotides for each color channel need to be read to ensure proper image registration. It is important to maintain color balance for each base of the index read being sequenced; otherwise index read sequencing could fail due to registration failure. This is especially likely a problem during low plexy sequencing where the relative small number of index sequences makes it more likely that all nucleotides in a read cycle activate one color.

In various applications, it is desirable to layout the index plate such that user may select groups of 3 across rows (i.e., quarter rows) or groups of 4 down columns (i.e., half columns), or other plexy arrangements such as 6-plex, 8-plex, and 9-plex, without sacrificing color balance of the oligos in the flow cells.

Various implementations provide at least some of the following advantages.

Some implementations using short universal adapters and index primers can easily scale to high sample numbers without the need of new adapter design. Only need new index primers with new index sequences.

Some implementations using short universal adapters and index primers are cost effective, involving 1 complex part instead of 40 complex parts for 384 samples in a 16×24 multi-well plate with combinatorial index pairs.

Because oligonucleotide purification is expensive, shorter length (e.g., 33 bp vs. 70 bp) adapters are cheaper to process and provide higher yield. Further, high-performance liquid chromatography (HPLC) purification columns for different oligonucleotides can be shared across projects Universal adapters in some implementations can be made with simpler manufacturing processes. In implementations involving Y-shaped and blunt adapters, 2 oligos need to be annealed to make one universal adapter. In implementations involving dual strand, blunt, A&B version adapters, 4 oligos need to be annealed to make two universal adapters.

Some implementations provide a simpler quality control (QC) process. Various existing processes and tools are fully functional for adapters, including gravimetric process (weighing of oligos), OD, mass spectrometry, and purity assay for index primers.

Assay performance may be improved due to smaller adapter size, leading to increased ligation efficiency and more efficient clean up to remove dimers (e.g., using SPRI beads).

Workflow for Sequencing Nucleic Acid Fragments Using Index Sequences

Figure 1B:
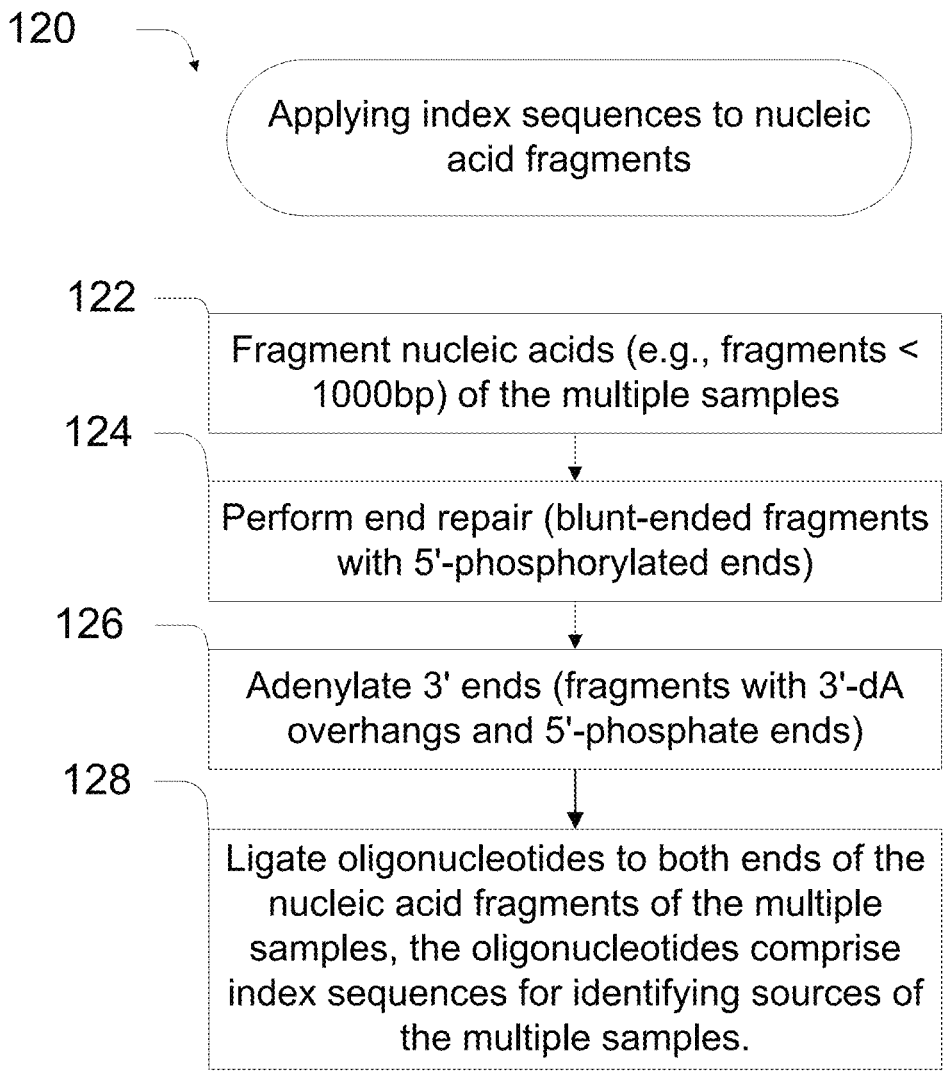
Figure 1C:
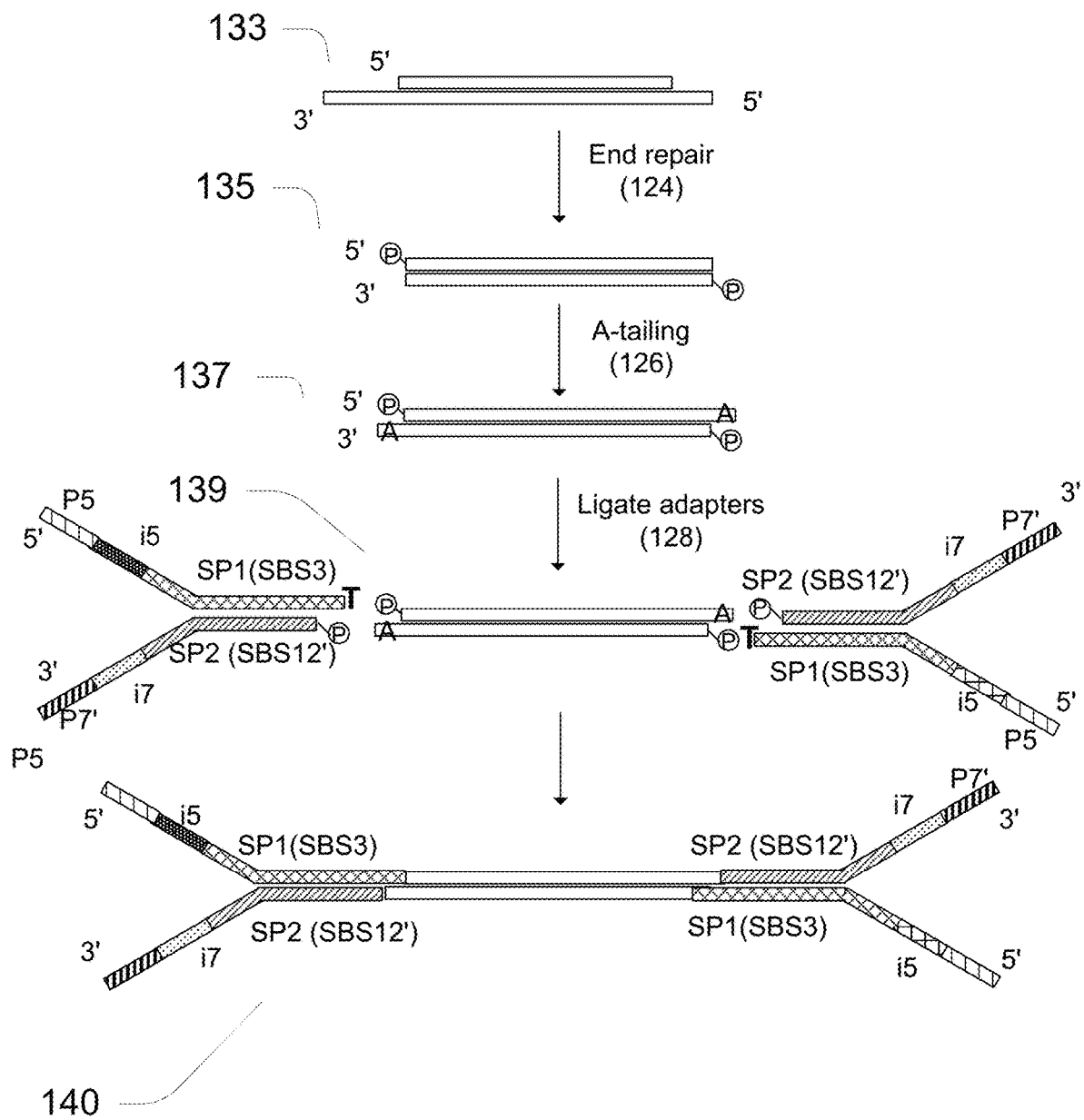

FIGS. 1A-1C illustrate example workflows 100 and 120 for using index sequences to sequence nucleic acid fragments. Workflows 100 and 120 are illustrative of only some implementations. It is understood that some implementations employ workflows with additional operations not illustrated here, while other implementations may skip some of the operations illustrated here. For instance, workflow 120 is employed for whole genome sequencing. In some implementations involving targeted sequencing, operational steps to hybridize and enrich certain regions may be applied between operation 122 and 128. Also, the workflows shows applying index sequences by ligation of sample specific indexed adapters. Transposome mediated adapter may be applied. Also, universal adapter without sample specific sequences may be applied in instead or in addition.

Operation 102 applies oligonucleotides to both ends of the nucleic acid fragments (or target fragments) of the multiple samples, the oligonucleotides including index sequences for identifying sources of the multiple samples. In some implementations, the index sequences are selected form a set of index sequences including at least 6 different index sequences, each subset of the plurality of subsets of oligonucleotides including a plurality of index sequences of the set of index sequences. In some implementations, a Hamming distance between any two index sequences of the set of index sequences is not less than a first criterion value, wherein the first criterion value is at least 2. The set of index sequences comprises a plurality of pairs of color-balanced index sequences, wherein any two bases at corresponding sequence positions of each pair of color-balanced index sequences include both (i) an adenine (A) base or a cytosine (C) base, and (ii) a guanine (G) base, a thymine (T) base, or a uracil (U) base.

In some implementations, operation 102 attaches to each end of double-stranded target fragments isolated from a source to result in adapter-target-adapter molecules. The attachment can be through standard library preparation techniques using ligation, or through tagmentation using transposase complexes (Gunderson et al., WO 2016/130704). In some implementations, the attachment can be performed by a ligation process 120 shown in FIG. 1B.

Process 120 involves fragmenting nucleic acid of multiple samples. In some implementations, the fragments are double-stranded DNA of size, e.g., smaller than 1000 bp. The DNA fragments may be obtained by fragmenting genomic DNA, collecting naturally fragmented DNA (e.g., cfDNA or ctDNA), or synthesizing DNA fragments from RNA, for example. In some implementations, to synthesize DNA fragments from RNA, messenger RNA or noncoding RNA is first purified using polyA selection or depletion of ribosomal RNA, then the selected mRNA is chemically fragmented and converted into single-stranded cDNA using random hexamer priming. A complementary strand of the cDNA is generated to create a double-stranded cDNA that is ready for library construction. To obtain double stranded DNA fragments from genomic DNA (gDNA), input gDNA is fragmented, e.g., by hydrodynamic shearing, nebulization, enzymatic fragmentation, etc., to generate fragments of appropriate lengths, e.g., about 1000 bp, 800 bp, 500, or 200 bp. For instance, nebulization can break up DNA into pieces less than 800 bp in short periods of time. This process generates double-stranded DNA fragments.

In some implementations, fragmented or damaged DNA may be processed without requiring additional fragmentation. For instance, formalin-fixed, paraffin embedded (FFPE) DNA or certain cfDNA are sometimes fragmented enough that no additional fragmentation step is required.

FIG. 1C shows a DNA fragment/molecule and the adapters employed in initial steps of workflow 120 in FIG. 1B. Although only one double-stranded fragment is illustrated in FIG. 1C, thousands to millions of fragments of a sample can be prepared simultaneously in the workflow. DNA fragmentation by physical methods produces heterogeneous ends, comprising a mixture of 3' overhangs, 5' overhangs, and blunt ends. The overhangs will be of varying lengths and ends may or may not be phosphorylated. An example of the double-stranded DNA fragments obtained from fragmenting genomic DNA of operation 122 is shown as fragment 133 in FIG. 1C.

Fragment 133 has both a 3' overhang on the left end and a 5' overhang shown on the right end. If DNA fragments are produced by physical methods, workflow 120 proceeds to perform end repair operation 124, which produces blunt-end fragments having 5'-phosphorylated ends. In some implementations, this step converts the overhangs resulting from fragmentation into blunt ends using T4 DNA polymerase and Klenow enzyme. The 3' to 5' exonuclease activity of these enzymes removes 3' overhangs and the 5' to 3' polymerase activity fills in the 5' overhangs. In addition, T4 polynucleotide kinase in this reaction phosphorylates the 5' ends of the DNA fragments. The fragment 135 in FIG. 1C is an example of an end-repaired, blunt-end product.

After end repairing, workflow 120 proceeds to operation 126 to adenylate 3' ends of the fragments, which is also referred to as A-tailing or dA-tailing, because a single dATP is added to the 3' ends of the blunt fragments to prevent them from ligating to one another during the adapter ligation reaction. Double stranded molecule 137 of FIG. 1C shows an A-tailed fragment having blunt ends with 3'-dA overhangs and 5'-phosphate ends. A single 'T' nucleotide on the 3' end of each of the two sequencing adapters as seen in item 139 of FIG. 1C provides an overhang complementary to the 3'-dA overhang on each end of the insert for ligating the two adapters to the insert.

After adenylating 3' ends, workflow 120 proceeds to operation 128 to ligate oligonucleotides, e.g., adapters, to both ends of the fragments of the multiple samples. The oligonucleotides include index sequences for identifying sources of the multiple samples.

Item 139 of FIG. 1C illustrates two adapters to be ligated to the double-stranded fragment that includes two index sequences i5 and i7. The index sequences provide a means to identify the sources of the plurality of samples, thereby allowing multiplexing of multiple samples on the sequencing platform. Other index sequences may be applied. The P5 and P7' oligonucleotides are complementary to the amplification primers bound to the surface of flow cells of Illumina sequencing platform, and are also referred to as amplification primer binding site. They allow the adapter-target-adapter library to undergo bridge amplification. Other designs of adapters and sequencing platforms may be used in various implementations. Adapters and sequencing technology are further described in sections that follow. The adapters also include two sequence primer binding sequences SP1 (e.g., Illumina's SBS3 primer for reading the i5 index sequence) and SP2 (e.g., SBS12'). Other sequencing primer binding sequence may be included in the adapters for different reactions and platforms.

Returning to FIG. 1A, process 100 proceeds to pool the nucleic acid fragments from the multiple samples for sequencing reactions. See block 104. Index oligonucleotides including the index sequences are attached to the fragments, which index sequences are applied in manners that are specific to the sources as samples. Various techniques for pooling the samples are further described hereinafter.

In some implementations, the products of this ligation reaction are purified and/or size-selected by agarose gel electrophoresis or magnetic beads. Size-selected DNA is then PCR amplified to enrich for fragments that have adapters on both ends. See block 106. As mentioned above, in some implementations, operations to hybridize and enrich certain regions of the DNA fragments may be applied to target the regions for sequencing.

Workflow 100 then proceeds to cluster amplify PCR products, e.g., on an Illumina platform. See operation 108. By clustering of the PCR products, libraries can be pooled for multiplexing, e.g., with 96 samples or more per lane, using different index sequences on the adapters to keep track of different samples. 1536 multiplex technologies are contemplated.

After cluster amplification, sequencing reads can be obtained through sequencing by synthesis on the Illumina platform. See operation 110. The obtained reads include reads for the target sequences and index sequences. Although the adapters and the sequencing process described here are based on the Illumina platform, others sequencing technologies, especially NGS methods may be used instead of or in addition to the Illumina platform. Finally, workflow 100 the sources of the samples of the target sequences based on the index sequences associated with the samples. See operation 112.

Figure 1D:
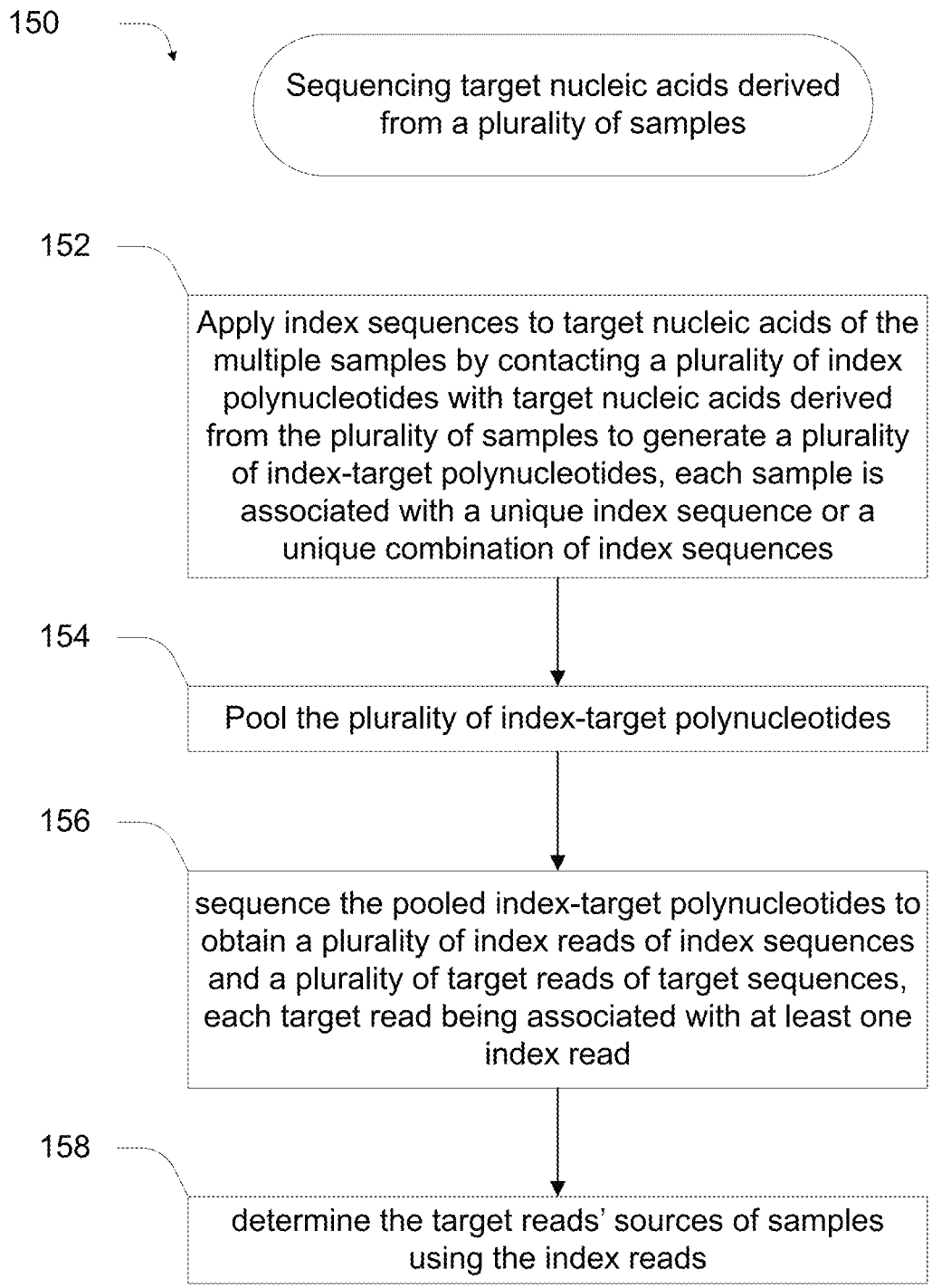
FIG. 1D illustrates a process for sequencing target nucleic acids derived from a plurality of samples according to some implementations.

FIG. 1D illustrates process 150 for sequencing target nucleic acids derived from a plurality of samples. Process 150 involves applying index sequences to target nucleic acid of the multiple samples by contacting a plurality of index polynucleotides with target nucleic acid derived from the samples to generate a plurality of index-target polynucleotides. In some implementations, the plurality of index polynucleotides includes DNA or RNA. Each sample is associated with a unique index sequence or a unique combination of index sequences. See block 152. In some implementations, the plurality of index polynucleotides includes sample-specific adapters including index sequences that are uniquely associated with each sample. FIGS. 1C, 2A, and 2B illustrate implementations using sample-specific adapters. In other implementations, the plurality of index polynucleotides includes index primers that can be hybridized to universal adapters attached to the target nucleic acids. FIGS. 1C, 1K, 2C, and 2D illustrate some implementations using index primers and universal adapters.

Figure 1E:
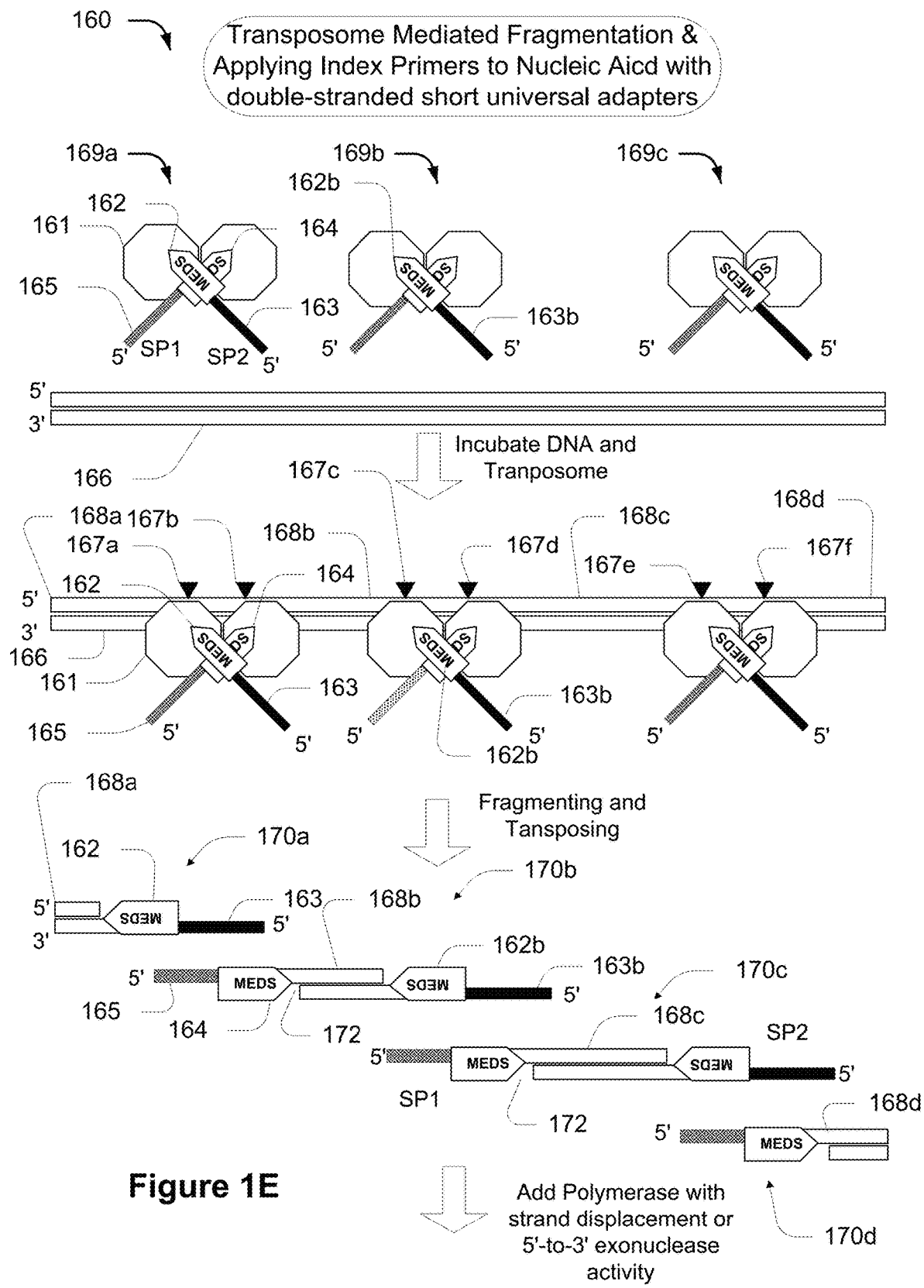
FIGS. 1E and 1F show a process of performing transposome mediated fragmentation and applying index primers to nucleic acid with double-stranded short universal adapters attached to both ends.
Figure 1F:
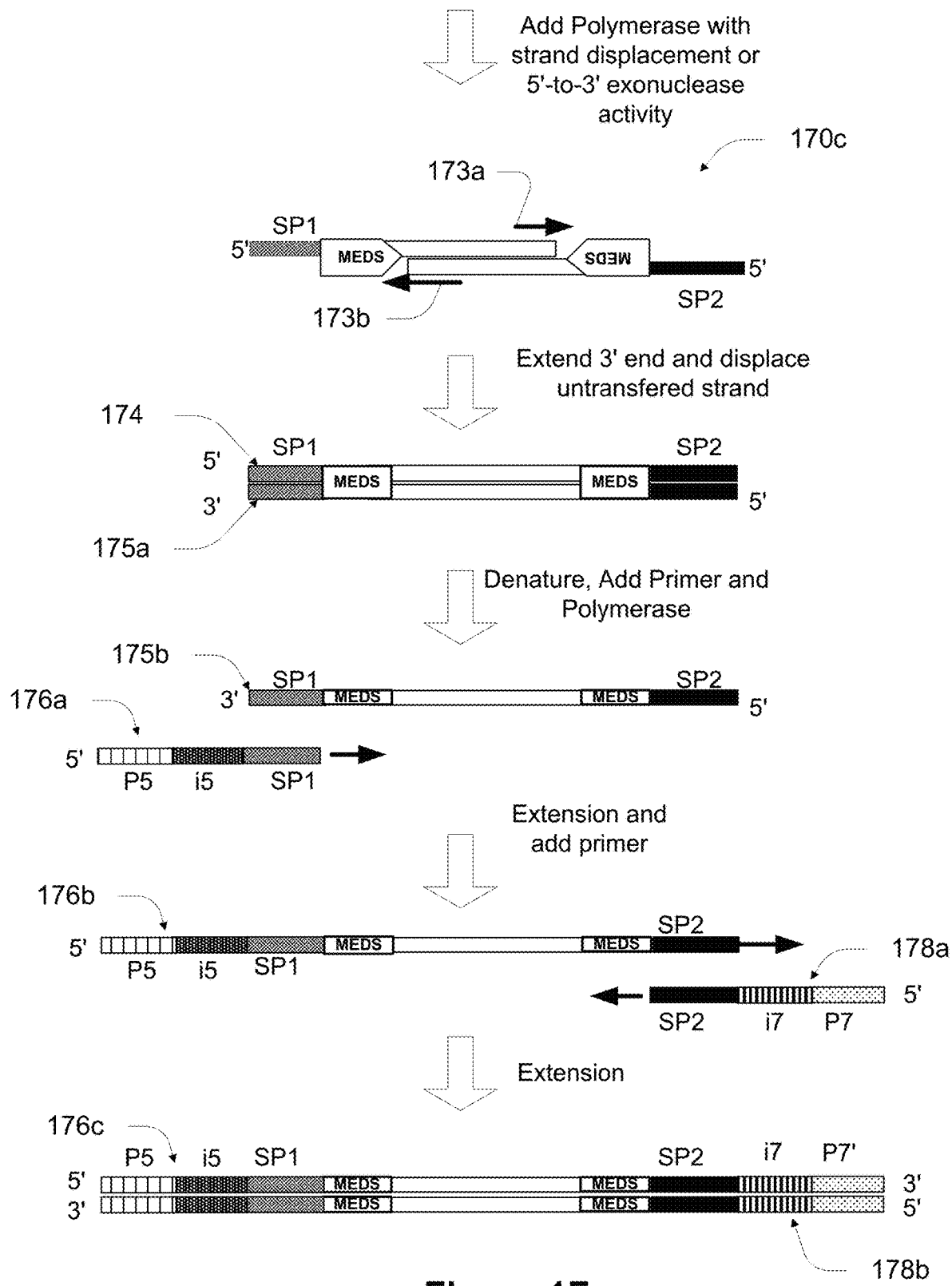
Figure 1K:
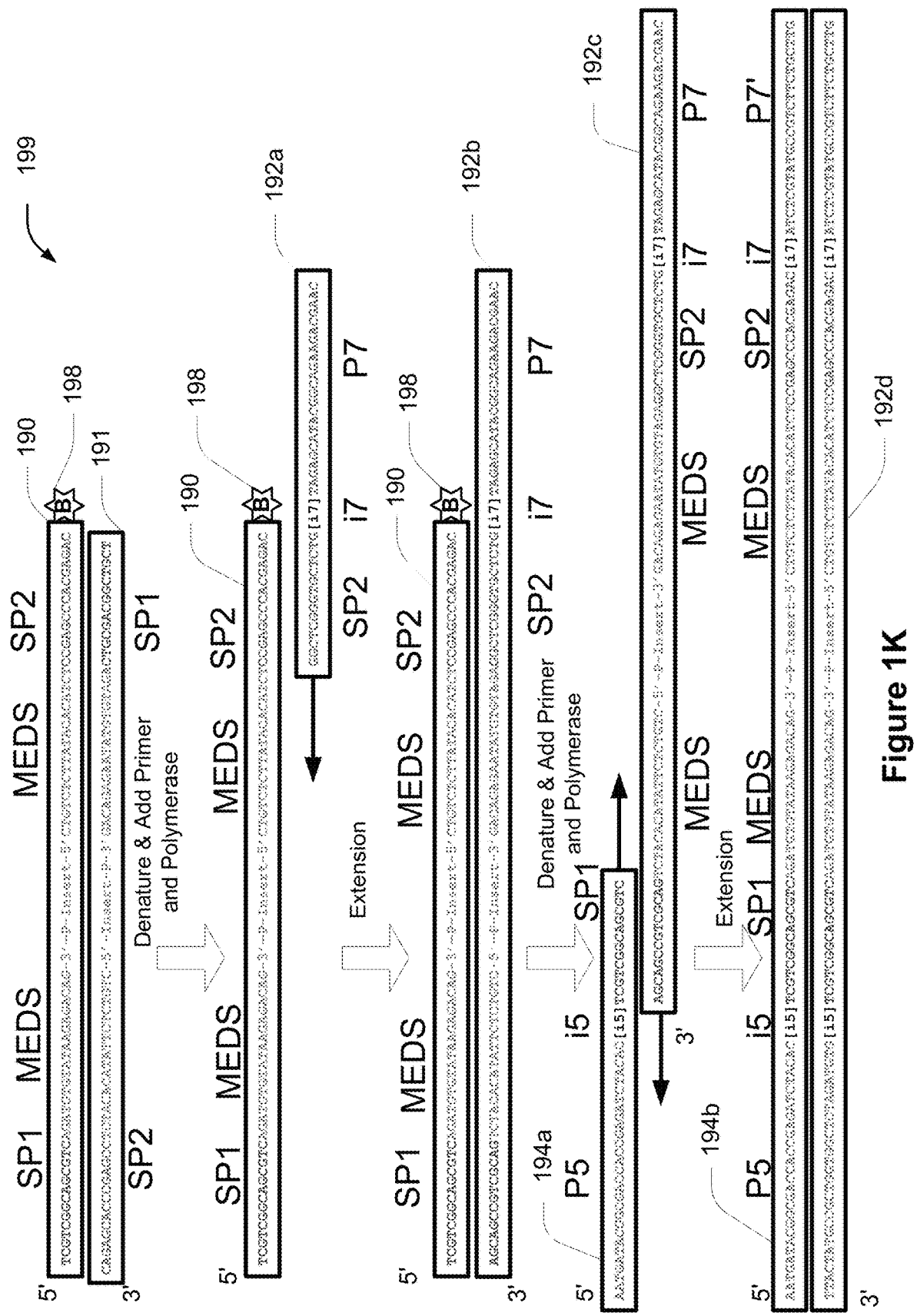
FIG. 1K shows a process of adding index sequences to a nucleic acid having Y-shaped short universal adapters on both ends according to some implementations.
Figure 2A:
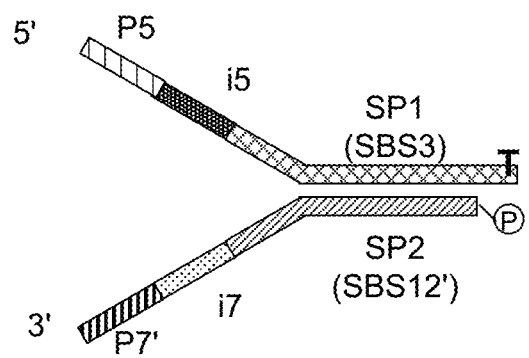
FIGS. 2A-2D show various implementations of index oligonucleotides.
Figure 2B:
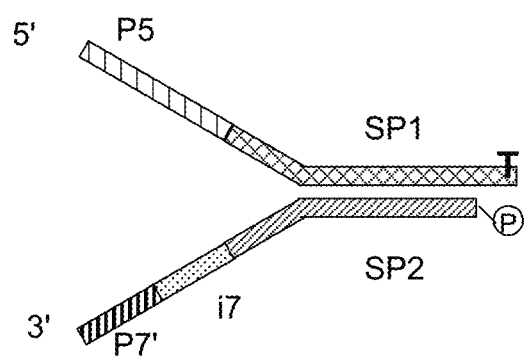

In some implementations, applying index primers to target nucleic acids of the multiple samples may be accomplished by the second half of process 160 illustrated in FIG. 1F or process 199 illustrated in FIG. 1K. FIGS. 1E and 1F show a process of performing transposome mediated fragmentation and applying index primers to nucleic acid with double-stranded short universal adapters attached to both ends.

Process 160 involves providing a plurality of double-stranded nucleic acid molecules derived from a plurality of samples. Double-stranded nucleic acid 166 (e.g., DNA) is a schematic illustration of one of the double-stranded nucleic acid molecule. Process 160 also involves providing a plurality of transposome complexes. Each transposome complex includes a transposase and two transposon end compositions. Elements 161-165 form a transposome complex. Three transposome complexes 169a-c are illustrated here. Transposome complex 169a includes a transposase 161 and two transposon end compositions. Transposon end sequence duplex 162 and the 5' tag 163 form one transposon end composition. Transposon end sequence duplex 164 and 5' tag 165 form another transposon end composition. The transposon end sequence duplexes 162 and 164 include two strands of sequences collectively referred to as MEDS. One strand of the MEDS duplex includes the sequence of SEQ ID NO: 1, which is to be transferred from the transposon complex to the target DNA and is referred to as the transferred strand. Another strand of the MEDS includes the transposon end sequence of SEQ ID NO: 2, which is not transferred to the target nucleic acid and is referred to as the untransferred strand. At the 5' end of the transferred strand, the transposon end composition includes a 5' tag 165. In some implementations, this 5' tag is a sequence primer binding sequence SP1, which provides a sequence binding site on the target nucleic acid after being transposed to the target nucleic acid. Transposon end duplex MEDS 162 and 5' tag 163 form another transposon end composition. In the 5' end of the transferred strand of the transposon end composition is a 5' tag sequence 163, which provides the sequence primer binding sequence SP2.

Similarly, transposome complexes 169b and 196c include the same components of transposome complex 169a. For instance, transposome complex 169b includes two transposon end compositions, one of which includes transposon end duplex 162b and a 5' tag 163b (SP2).

Process 160 involves incubating the DNA fragments and transposome complexes under conditions that allow transposition reactions with the suitable concentrations of transposon complexes and DNA molecules. The transposases in the transposon complexes digest double-stranded nucleic acid 166 at random sites indicated by black triangles 167a-f. The digestion divides the double-stranded nucleic acid molecule 166 into multiple fragments including fragments 168a-d.

The transposases also transpose the transferred strand of the MEDS duplex to the 5' ends of the nucleic acid fragments in the digestion sites (167a-f). After the fragmenting and transposing, the 5' end of the top strand of fragment 168b has a transferred strand of a MED duplex (164) transposed and attached to the 5' end. At the 5' end of the transferred strand there is a 5' tag (165) that corresponds to sequencing primer binding sequence SP1. At each 3' end of the double-stranded target fragment 168b there is a gap between the untransferred strand of the MEDS transposon end sequence and the target fragment. After the fragmenting and transposition, four fragments are formed (170a-d). Two of the four fragments, 170b and 170c, have MEDS duplexes on both ends, which MEDS duplexes have 5' tags. Two of the fragments (170a and 170d) have transposon end composition on only one end, which are not processed in downstream sequencing reactions. In some implementations, after the target DNA fragments are formed and tagged, DNA polymerases with strand displacement or 5'-to-3' exonuclease activity are added to extend the 3' end of the target nucleic acids.

FIG. 1F shows further downstream processes of DNA fragments resulted from transposome mediated fragmentation to obtain target nucleic acid fragments having double-stranded universal adapters on both ends. The figure also shows the addition of index sequences (i5 and i7 index sequences) and flow cell amplification primer binding sequences (P5 and P7 sequences). After polymerases with strand displacement or 5'-to-3' exonuclease activity are added, the 3' ends of the target nucleic acids are extended, and the untransferred strand of the MEDS duplex is removed (see arrows 173a and 173b indicating the extension of the 3' end of the target nucleic acid fragments). The extension fills in the gap between the 3' end of the target nucleic acid and the untransferred strand of the MEDS duplex. The extension also generates nucleotides complementary to the 5' tags. As a result, double-stranded target nucleic fragments flanked by MEDS sequences and sequencing primer binding sequences are formed with two complementary strands 174 and 175a. The double-stranded nucleic acid includes two double-stranded short universal adapters, each adapter includes a sequencing primer sequence and an MEDS sequence. In some implementations, the double-stranded nucleic acid has the nucleotides shown in FIG. 1G.

FIG. 1G shows the sequences of a target nucleic acid having double-stranded short universal adapters attached to both ends. The sequencing primer binding sequence SP1 has the sequence TCGTCGGCAGCGTC (SEQ ID NO: 3) at the top strand and the reverse complement at the bottom strand GACGCTGCCGACGA (SEQ ID NO: 4). The MEDS duplex has the sequences of SEQ ID NO: 1 and SEQ ID NO: 2. The sequencing primer binding sequence (SP2) has the sequence CCGAGCCCACGAGAC (SEQ ID NO: 5) at the top strand and the reverse complement GTCTCGTGGGCTCGG (SEQ ID NO: 6) at the bottom strand.

FIG. 1I shows sequences in an i7 index primer. In some implementations, the i7 index primer (e.g., 178a) has, from 5' to 3', a P7 flow cell amplification primer binding sequence CAAGCAGAAGACGGCATACGAGAT (SEQ ID NO: 7), an i7 index sequence, and the SP2 sequencing primer binding sequence GTCTCGTGGGCTCGG (SEQ ID NO: 6).

FIG. 1J shows sequences in an i5 index primer. In some implementations, the i5 index primer (e.g., 176a) has, from 5' to 3', a P5 flow cell amplification primer binding sequence AATGATACGGCGACCACCGAGATCTACAC (SEQ ID NO: 8), an i5 index sequence, and an SP1 sequencing primer binding sequence TCGTCGGCAGCGTC (SEQ ID NO: 3).

In other implementations, target insert with Y-shaped universal adapters may be used in a process such as the one shown in FIG. 1K. FIG. 1H shows sequences of a target nucleic acid having Y-shaped short universal adapters attached to both ends according to some implementations. The Y-shaped universal adapter has the sequence TCGTCGGCAGCGTC (SEQ ID NO: 3) at the 5' arm and the sequence CCGAGCCCACGAGAC (SEQ ID NO: 5) at the 3' arm.

Process 160 further involves denaturing the double-stranded nucleic acid fragments with double-stranded short universal adapters on both ends. It also involves adding primers (176*a*) and nucleases that hybridize to the denatured nucleic acid fragments. As shown in the figure, the bottom strand 175*a* is further processed. The primer (176*a*) includes a P5 flow cell amplification primer binding side at the 5' end, an i5 index sequence downstream of the P5 sequence, and an SP1. This polynucleotide is also referred to as an index primer. The index primer hybridizes to the single-stranded nucleic acid 175*b* at the SP1 primer binding site. A polymerase extends the 3' end of the index primer 176*a* to form an extended single stranded nucleic acid fragments using the fragment 175*b* as a template. The resulting nucleic acid fragment is shown as 176*b*. The process then further adds primers and polymerases to further extend fragment 176*b*. The primer added in this reaction includes a P5 flow cell amplification primer binding site at the 5' and, an i7 index sequence 3' of the P7 sequence, and an SP2 sequencing primer binding sequence. Then the 3' end of the index primer sequence 178 is extended using the single-stranded nucleic acid 176*b* is a template. Moreover, the 3' end of nucleic acid 176*b* is also extended using the index primer 178*a* as a template. A result, a double-stranded nucleic acid fragments is formed, with one strand 176*c* extended from fragment 176*b*, and another strand 178*b* extended from index primer 178*a*. The final double-stranded nucleic acid fragments includes in the top strand (176*c*), from the 5' to the 3' direction, a P5 flow cell amplification primer binding site, an i5 sequence, an SP1 sequencing primer binding sequence, an MEDS sequence, a target sequence, an MEDS sequence, an SP2 sequence, an i7 sequence, and a P7' sequence. This final double-stranded nucleic acid fragment forms a library fragments for a sequencing platform such as Illumina's SBS platforms.

In accordance with process 160, some implementations provide a method for sequencing target nucleic acids derived from a plurality of samples. The method includes: (a) providing a plurality of double-stranded nucleic acid molecules derived from the plurality of samples; (b) providing a plurality of transposome complexes, wherein each transposome complex comprises a transposase and two transposon end compositions; (c) incubating the double-stranded nucleic acid molecules with the transposome complexes to obtain double-stranded nucleic acid fragments, wherein the double-stranded nucleic acid fragments comprise, at one or both ends, sequences transposed from the transposon end compositions; (d) contacting a plurality of index primers with the double-stranded nucleic acid fragments to generate a plurality of index-fragment polynucleotides, where index primers contacted with double-stranded nucleic acid fragments derived from each sample comprise an index sequence or a combination of index sequences that is uniquely associated with that sample, and the index sequence or the combination of index sequences is selected from a set of index sequences; (e) pooling the plurality of index-fragment polynucleotides; (f) sequencing the pooled index-fragment polynucleotides, thereby obtaining index reads of index sequences and a plurality of target reads of target sequences, each target read being associated with at least one index read; and (g) using the index reads to determine the target reads' sources of samples.

In some implementations, at least one of the transposome complexes comprises a Tn5 transposase and a Tn5 transposon end composition. In some implementations, at least one of the transposome complexes comprises a Mu transposase and a Mu transposon end composition. Some implementations include both Tn5 and Mu transposases and transposon end compositions.

FIG. 1K shows a process 199 of adding index sequences to a target nucleic acid having Y-shaped short universal adapters on both ends. The process 199 is similar to process 160 of FIG. 1E that uses target nucleic acid fragments with double-stranded short universal adapters attached to both ends. In process 199, target nucleic acids with Y-shaped short adapters attached to both ends are used. Because the two strands of a Y-shaped adapter have two different sequencing primer binding sequences, both strands of the nucleic acid can be used to generate downstream fragments that can be sequenced on a sequencing platform. In contrast, in implementations using double-stranded adapters, only one strand of the product of the double-stranded nucleic acid can be used for sequencing.

The Y-shaped adapters and index primers are shown with the nucleic acid sequences according to the implementations illustrated in FIGS. 1H-1J. A double-stranded nucleic acid with two Y-shaped short universal adapters attached to both ends is shown at the beginning of this process. The double-stranded nucleic acid includes a top strand 190 and a bottom strand 191. At the 3' end of the top strand 190 is shown a blocking moiety 198, which blocks the nucleic acid from extending when polymerases are added. Although only one blocking group is shown in the figure, in some implementations, additional blocking groups can be applied to other ends of the double-stranded nucleic acid.

Various blockers may be implemented. One form of possible blockers includes phosphorothioate (PS) bonds. The phosphorothioate (PS) bond substitutes a sulfur atom for a non-bridging oxygen in the phosphate backbone of an oligonucleotide. Approximately 50% of the time (due to the 2 resulting stereoisomers that can form), PS modification renders the internucleotide linkage more resistant to nuclease degradation. Therefore, including at least 3 PS bonds at the 5 and 3 oligonucleotide ends is recommended to inhibit exonuclease degradation. Including PS bonds throughout the entire oligonucleotide will help reduce attack by endonucleases as well, but may also increase toxicity.

Another form of possible blockers includes inverted dT and ddT. Inverted dT can be incorporated at the 3' end of an oligonucleotide, leading to a 3 '-3' linkage that will inhibit degradation by 3' exonucleases and extension by DNA polymerases. In addition, placing an inverted, 2',3' dideoxy-dT base (5' inverted ddT) at the 5' end of an oligonucleotide prevents spurious ligations and may protect against some forms of enzymatic degradation.

Another form of possible blockers includes phosphorylation. Phosphorylation of the 3' end of oligonucleotides will inhibit degradation by some 3'-exonucleases.

Another form of possible blockers includes LNA, where xGen locked nucleic acid modification prevents endo and exonuclease digest.

The top strand 190 includes, from 5' to 3', an SP1 sequence, an MEDS sequence, a target insert, an MEDS sequence, and an SP2 sequence. The bottom strand 191 includes, from 3' to 5', an SP2 sequence, an MEDS sequence, a target insert, an MEDS sequence, and an SP1 sequence. Process 199 denatures the double-stranded nucleic acid, and adds primers and polymerases to the nucleic acids. Index primer 192a hybridizes to the SP2 primer binding sequence and extends using the single-stranded fragment 190 as a template. The 3' end of the single-stranded nucleic acid 190 does not extend because it is blocked by blocking group 198. After extension, the double-stranded structure including a top strand 190 and a bottom strand 192b is obtained. Then the double-stranded nucleic acid is denatured again. Process 199 adds primers and polymerases to the reaction mixture. The i5 index primer 194a is added, which hybridizes to the SP1. The i5 index primer 194a includes, from 5' to 3', a P5 sequence, an i5 index sequence, and an SP1 primer binding sequence. The i5 index primer hybridizes to the SP1 sequence of the single-stranded nucleic acid 192C. Then PCR reaction extends the 3' end of the i5 index primer 194 a, as well as the 3' end of the single-stranded fragment 192c. After polymerase extension, a double-stranded nucleic acid is obtained, including a top strand 194b, and a bottom strand 192d. Top strand 194b includes, from 5' to 3', a P5 flow cell amplification primer binding sequence, an i5 index sequence, an SP1 sequencing primer binding sequence, an MEDS sequence, the target sequence, an MEDS sequence, an SP2 sequencing primer binding sequence, an i7 index sequence, and a P7' flow cell amplification primer binding sequence. This double-stranded nucleic acid includes the sequences needed for amplification and the sequencing reactions on an Illumina sequencing platform.

Returning to FIG. 1D, process 150 involves applying index sequences to target nucleic acids of the multiple samples. In some implementations, this is achieved by contacting the plurality of index polynucleotides with target nucleic acids derived from the plurality of samples to generate a plurality of index-target polynucleotides. In some implementations, index polynucleotides contacted with target nucleic acids derived from each sample includes an index sequence or a combination of index sequences that is uniquely associated with that sample. The index sequence or the combination of index sequences is selected from a set of index sequences. Hamming distance between any two index sequences of the set of index sequences is not less than a first criterion value, where the first criterion value is at least two.

In some implementations, the set of index sequences includes a plurality of pairs of color-balanced index sequences, where any two bases at corresponding sequence positions of each pair of color-balanced index sequences include both (i) an A base or a C base, and (ii) a G base, T base, or a U base. In some implementations, the set of index sequences includes at least six different index sequences.

In some implementations, the plurality of index polynucleotides includes index primers that can be hybridized to universal adapters. In some implementations, the plurality of index primers includes index sequences of the set of index sequences. In some implementations, each index primer further includes a flow cell amplification primer binding sequence. In some implementations, the flow cell application primer binding sequence includes a P5 or a P7' sequence. See FIGS. 2C and 2D. In some implementations, the target nucleic acids derived from the plurality of samples include nucleic acids with universal adapters covalently attached to one or both ends. See nucleic acid having a top strand 174 and a bottom strand 175a in FIG. 1F and nucleic acid having a top strand 190 and a bottom strand 191 in FIG. 1K.

In some implementations, the contacting the plurality of index polynucleotides with the target nucleic acids derived from the plurality of samples includes: hybridizing the plurality of index primers to the universal adapters covalently attached to one or both ends of the nucleic acids; and extending the plurality of index crime index primers to obtain a plurality of index-adapter-target polynucleotides. In some implementations, the universal adapters and the target nucleic acids are double-stranded, and hybridizing the plurality of index primers to the universal adapters includes hybridizing the plurality of index primers to only one strand of the universal adapters.

In some implementations, the universal adapters and the target nucleic acids are double-stranded, and the hybridizing the plurality of index primers to the universal adapters includes hybridizing the plurality of index primers to both strands of the universal adapters. See FIGS. 1F and 1K.

In some implementations, index primers hybridized to a first strand of the universal adapters include index sequences selected from the first subset of the set of index sequences and index primers hybridized to a second strand of the universal adapters include sequences selected from a second subset of the set of index sequences, the first subset not overlapping the second subset. In some implementations, the first subset includes index sequences listed in Table 1 and a second subset includes index sequences listed in Table 2. In some implementations, the index primers hybridized to both strands of the universal adapters include index sequences selected from the same subset of the set of index sequences. In some implementations, the subset of index sequences is selected from one of the subsets of index sequences in Table 3.

In some implementations, the universal adapters include double-stranded adapters. See, e.g., FIG. 2D. In some implementations, the universal adapters include Y-shaped adapters. See, e.g., FIG. 2C. In some implementations, the universal adapters include single stranded adapters. In some implementations, the universal adapters include hairpin adapters. In some implementations, each of the universal adapters includes, before being attached to a nucleic acid, an overhang at one end to be attached to the nucleic acid. In some implementations, the overhang is a T overhang. See FIGS. 1C, and 2A-2C. In some implementations, each of the universal adapters includes, before being attached to a nucleic acid, a blunt end to be attached to the nucleic acid. See FIG. 2D.

In some implementations, the methods includes, before applying index sequences to target nucleic acids, attaching the universal adapters to one or both ends of the nucleic acids. In some implementations, the attaching includes attaching the universal adapters by transposome mediated fragmentation.

In some implementations, the attaching includes ligating the universal adapters to the one or both ends of the nucleic acids. In some implementations, the ligating includes enzymatic ligation or chemical ligation.

In some implementations, the attaching is by amplification with target-specific primers including a universal adapter sequence. In some implementations, the universal adapter sequence is at the terminal of the primer.

Some implementations apply a plurality of index polynucleotides including sample-specific adapters. The adapters include index sequences of the set of index sequences. See FIGS. 1C and 2A-2C. In some implementations, the sample-specific adapters include two strands. In some implementations, only one strand includes an index sequence. In some implementation, each strand of the sample-specific adapters includes an index sequence. In some implementations, a first strand of the sample-specific adapters includes index sequences selected from a first subset of the set of index sequences, and a second strand of the sample-specific adapters includes index sequences selected from a second subset of the set of index sequences, the first subset not overlapping the second subset. In some implementations, the first subset of index sequences includes index sequences listed in Table 1, and the second subset includes index sequences listed in Table 2. In some implementations, the first and second strands of the sample-specific universal adapters include index sequences selected from the same subset of the set of index sequences. In some implementations, the subset of index sequences is selected from one of the subsets of index sequences in Table 3.

In some implementations, each sample-specific adapter includes a flow cell application primer binding sequence. See FIGS. 1C, 2A, and 2B. In some implementations, the flow cell amplification primer binding sequence includes a P5 or a P7' sequence.

In some implementations, contacting the plurality of index polynucleotides with the target nucleic acids includes attaching the sample-specific adapters to the target nucleic acids by transposome mediated fragmentation. In some implementations, the contacting the plurality of index polynucleotides with the target nucleic acids includes ligating the sample-specific adapters to the target nucleic acids. In some implementations, the ligating includes enzymatic ligation or chemical ligation. In some implementations, the chemical ligation includes chemistry ligation.

In some implementations, the sample-specific adapters include Y-shaped adapters having a complementary double-stranded region and a mismatched single-stranded region. In some implementations, each strand of the sample-specific adapters includes an index sequences at the mismatched single-stranded region. In some implementations, only one strand of the sample-specific adapters includes an index sequence at the mismatched single-stranded region. In some implementations, the sample-specific adapters include single-stranded adapters. In some implementations, the sample-specific adapters include hairpin adapters. In some implementations, the contacting the plurality of index polynucleotides with target nucleic acids involves attaching the plurality of index polynucleotides to both ends of the target nucleotides.

In some implementations, the contacting the plurality of index polynucleotides with target nucleic acids includes attaching the plurality of index polynucleotides to both ends of the target nucleic acids. In some implementations, the contacting the plurality of index polynucleotides with target nucleic acids includes attaching the plurality of index polynucleotides to only one end of the target nucleic acids.

In some implementations, the combination of index sequences uniquely associated with sample is an ordered combination of index sequences.

In some implementations, the set of index sequences includes a plurality of non-overlapping subsets of index sequences, Hamming distance between any two index sequences in any subset being not less than a second criterion value, where the second criterion value is larger than the first criterion value. In some implementations, the first criterion value is 4, and the second criterion value is 5. In some imitations, the first criterion value is 3. In some implementations, the first criterion value is 4. Various other designs of sets of index sequences can be applied as further described herein after.

In some implementations, process 150 includes, before applying index sequences to target nucleic acids of the multiple samples, fragmenting nucleic acid molecules obtained from the plurality of samples to obtain the target nucleic acids. In some implementations, the fragmenting includes transposome mediated fragmentation such as the process shown in FIG. 1E.

In some implementations, the fragmenting is contacting the plurality of PCR primers targeting a sequence of interest to obtain the target nucleic acids including the sequence of interest.

Process 150 involves, after obtaining the plurality of index-target polynucleotides, pooling the plurality of index-target polynucleotides. See block 154. In some implementations, process 150 further includes amplifying the pool index-target polynucleotides before sequencing the polynucleotides.

In some implementations, process 150 further involves sequencing the pulled index-target polynucleotides to obtain a plurality of index reads of index sequences and the plurality of targets reads of target sequences, each target read being associated with at least one index read. See block 156.

Process 150 further involves determining the target reads' sources of samples using the index reads. In some implementations this is achieved by a process including: obtaining, for each index reads, alignment scores with respect to the set of index sequences, each alignment score indicating similarity between the sequence of the index read and an index sequence of the set of index sequences; determining that the index read is aligned to the particular index sequence based on the alignment scores; and determining that the target read associated with the particular index read is derived from the sample uniquely associated with the particular index sequence.

Index Sequence Design

In various implementations, index sequences or oligonucleotides are identified, taking into consideration various factors, including but not limited to, means for detecting errors within the index sequences, conversion efficiency, assay compatibility, GC content, homopolymers, and manufacturing considerations.

Figure 3:
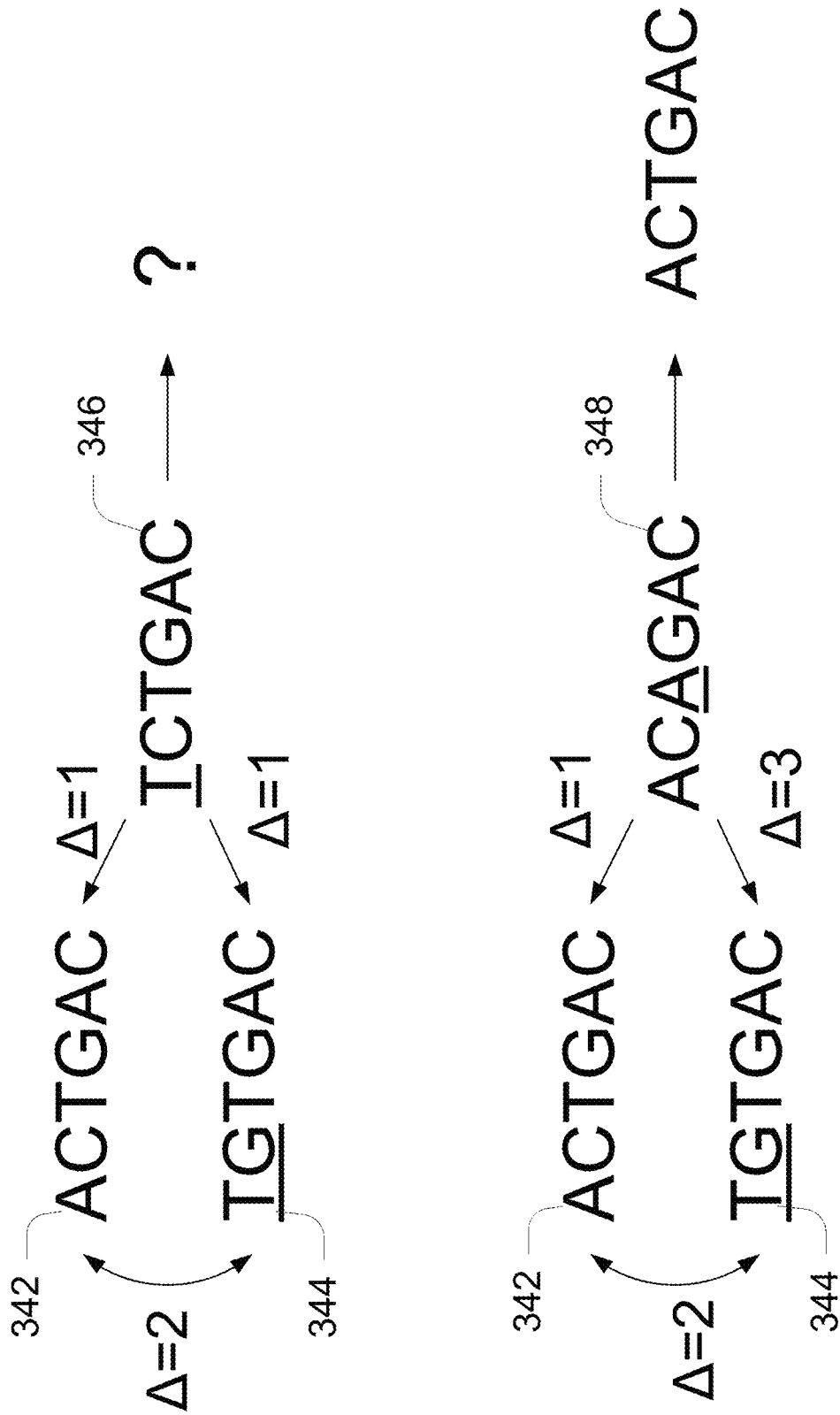
FIG. 3 schematically illustrates an index sequence design that provides a mechanism for detecting errors that occur in the index sequence during a sequencing process.

For instance, index sequences may be designed to provide a mechanism for facilitating error detection. FIG. 3 schematically illustrates an index oligonucleotide design that provides a mechanism for detecting errors that occur in the index sequence during a sequencing process. According to this design, each of the index sequence has six nucleotides and differs from every other index sequence by at least two nucleotides. As illustrated in FIG. 3, the index sequence 344 differs from the index sequence 342 in the first two nucleotides from the left, as shown by the underlined nucleotides T and G in index sequence 344 and nucleotides A and C in index sequence 342. Index sequence 346 is a sequence identified as part of a read, and it is different from all other index sequences of adapters provided in the process. Since the index sequence in a read is supposedly derived from an index sequence in an adapter, an error likely has occurred during the sequencing process, such as during amplification or sequencing. Index sequence 342 and index sequence 344 are illustrated as the two index sequences most similar to the index sequence 346 in the read. It can be seen that index sequence 346 differs from index sequence 342 by one nucleotide in the first nucleotide from the left, which is T instead of A. Moreover, index sequence 346 also differs from index sequence 344 by one nucleotide, albeit in the second nucleotide from the left, which is C instead of G. Because index sequence 346 in the read differs from both index sequence 342 and index sequence 344 by one nucleotide, from the information illustrated, it cannot be determined whether index sequence 346 is derived from index sequence 342 or index sequence 344. However, in many other scenarios, the index sequence errors in the reads are not equally different from the two most similar index sequences. As shown in the example for index sequence 348, index sequence 342 and index sequence 344 are also the two index sequences most similar to the index sequence 348. It can be seen that index sequence 348 differs from index sequence 342 by one nucleotide in the third nucleotide from the left, which is A instead of T. In contrast, index sequence 348 differs from index sequence 344 by three nucleotides. Therefore, it can be determined index sequence 348 is derived from index sequence 342 instead of index sequence 344, and an error likely occurred in the third nucleotide from the left. By controlling the level of difference (e.g., as measured by Hamming distance or edit distances) between index sequences, some implementations provide index oligonucleotides for identifying sources of multiple samples, wherein sequencing errors, sample processing errors, and other errors can be corrected by assigning an index sequence read to a closely matched index sequence and a sample associated with the closely matched index sequence.

Some implementations apply an i5-i7 index pair to multiple samples, where each ordered pair of index is unique. The Hamming distance between any two index sequences in a complete set of index sequences are controlled to be above a threshold value. In some implementations, the Hamming distance between an ordered pair of indexes is also controlled to be above a threshold value. Moreover, in some implementation, the edit distance between index sequences is also controlled. These and other elements of index oligonucleotides allow detection and correction of index hopping by identifying errors that would otherwise be ambiguous and not correctable.

One typical calculation of edit distance is the Levenshtein distance, wherein each insertion, deletion, or substitution will be counted as a single edit operation and scored equivalently. Consider the case of "ACTGACTA" and "ACTACTAA". The Levenshtein edit distance in this case will be 2, as shown in the alignment below

ACTGACTA-
ACT-ACTAA

However, in the case of index sequences, this may be an underestimate of the true distance between these two sequences. In reality, the index sequence will be extended with a base from the surrounding adapter. If the base from the surrounding adapter happens to match another index sequence, it will actually only take a single deletion event to transform one index sequence into the other. In addition, the index may be read in the reverse direction, in which case the additional adapter sequence may come at the 5' end of the index. While it is possible to look at the expected adapter sequence to understand the likelihood of this occurrence, this would make the index sequences only valid in the context of a specific adapter. Rather, a custom edit distance is generated that always assumes the neighboring adapter sequence will match the adapter. In this custom edit distance, only a single insertion/deletion event is allowed. An edit distance threshold of 3 means that no index pair is allowed where a single deletion+substitution can transform one index sequence into the other.

In some implementations, the edit distance is a modified Levenshtein distance where end gaps are assigned no penalty. U.S. Provisional Patent Application No. 62/447,851, which is incorporated herein by reference in its entirety, describes various methods of determining modified Levenshtein distance for nucleic acid sequences.

Index Oligonucleotides, Adapters, and Primers

In addition to the adapter design described in the example workflow 100 with reference to FIGS. 1A-1C above, other designs of index oligonucleotides may be used in various implementations of the methods and systems disclosed herein.

FIGS. 2A-2D show various implementations of index oligonucleotides. Although the adapters are labeled with various components, they can include additional components not labeled, such as additional primer binding sites or cleaving or digestion sites. FIG. 2A shows a standard Illumina TruSeq® dual index adapter. The adapter is partially double-stranded and is formed by annealing two oligonucleotides corresponding to the two strands. The two strands have a number of complementary base pairs (e.g., 12-17 or 6-34 bp) that allow the two oligonucleotides to anneal at the end to be ligated with a dsDNA fragment. A dsDNA fragment to be ligated on both ends for pair-end reads is also referred to as an insert. Other base pairs are unmatched (not complementary) on the two strands, resulting in a fork shaped or Y-shaped adapter having two floppy overhangs.

On the strand having the 5' floppy overhang (the top strand), from 5' to 3' direction, the adapter has a P5 sequence, i5 index sequence, and the sequencing primer binding sequence SP1 (e.g., SBS3). On the strand having the 3' floppy overhang, from 3' to 5' direction, the adapter has a P7' sequence, an i7 index sequence, and the SP2 sequencing primer binding sequence (e.g., SBS12'). The P5 and P7' oligonucleotides are complementary to the amplification primers bound to the solid phase of flow cells of a sequencing platform. They are also referred to as amplification primer binding sites, regions, or sequences. In some implementations, the index sequences provide means to keep track of the source of a sample, thereby allowing multiplexing of multiple samples on the sequencing platform.

The complementary base pairs are part of sequencing primer binding sequences SP1 and SP2. Downstream to the SP1 primer sequence (e.g., SBS3) is a single nucleotide 3'-T overhang, which provides an overhang complementary to the single nucleotide 3'-A overhang of a dsDNA fragment to be sequenced, which can facilitate hybridization of the two overhangs. The sequencing primer binding sequence SP2 (e.g., SBS12') is at the complementary strand, to which a phosphate group is attached upstream. The phosphate group facilitates ligating the 5' end of the SP2 sequence to the 3'-A overhang of the DNA fragment.

As in some implementation in which the index sequences are selected from a set of index sequences, each strand of the adapter includes an index sequence selected from the set of index sequences such as the set shown in Tables 1-3 and described elsewhere herein. In some implementations, each double-stranded sequencing adapter in the set of oligonucleotides includes a first strand including an index sequence selected from the first subset of the set of index sequences and a second strand including an index sequence selected from the second subset of the set of index sequences. The first subset does not overlap with the second subset. In some implementations, the first subset of index sequences comprises index sequences listed in Table 1, and the second subset of index sequences comprises index sequences listed in Table 2.

TABLE 1

17 Index Set Including Subsets (Index Groups 0-3)

| Index Label | Index Sequence |
| --- | --- |
| Index Group #0 | |
| Cipher7-001 | GTTACACC |
| Cipher7-002 | ACCGTGTT |
| Cipher7-003 | TCTCATAA |
| Cipher7-004 | CTCTGCGG |
| Cipher7-005 | TAGATTGC |
| Cipher7-006 | CGAGCCAT |
| Cipher7-007 | ATGGACCA |
| Cipher7-008 | GCAAGTTG |
| Cipher7-009 | GATCGATA |
| Cipher7-010 | AGCTAGCG |
| Cipher7-011 | TTAGTATC |
| Cipher7-012 | CCGACGCT |
| Cipher7-013 | TTCAAGGA |
| Cipher7-014 | CCTGGAAG |
| Cipher7-015 | CAATCTTA |
| Cipher7-016 | TGGCTCCG |
| Index Group #1 | |
| Cipher7-017 | TGATGTGG |
| Cipher7-018 | CAGCACAA |
| Cipher7-019 | ATTGCTAC |
| Cipher7-020 | GCCATCGT |
| Cipher7-021 | AACAGTTA |
| Cipher7-022 | GGTGACCG |
| Cipher7-023 | TTCCTGCC |
| Cipher7-024 | CCTTCATT |
| Cipher7-025 | TGGCAAGC |
| Cipher7-026 | CAATGGAT |
| Cipher7-027 | GTAACCAA |
| Cipher7-028 | ACGGTTGG |
| Cipher7-029 | ACATAGTA |
| Cipher7-030 | GTGCGACG |
| Cipher7-031 | AAGTGCGC |
| Cipher7-032 | GGACATAT |
| Index Group #2 | |
| Cipher7-033 | ACTTCCGA |
| Cipher7-034 | GTCCTTAG |
| Cipher7-035 | CGAGAGCC |
| Cipher7-036 | TAGAGATT |
| Cipher7-037 | TCCGCAAC |
| Cipher7-038 | CTTATGGT |
| Cipher7-039 | ATGCCGTC |
| Cipher7-040 | GCATTACT |
| Cipher7-041 | AGGATTCA |
| Cipher7-042 | GAAGCCTG |
| Cipher7-043 | GATTATCA |
| Cipher7-044 | AGCCGCTG |
| Cipher7-045 | CTACGTGC |
| Cipher7-046 | TCGTACAT |
| Cipher7-047 | TGTGAATA |
| Cipher7-048 | CACAGGCG |
| Index Group #3 | |
| Cipher7-049 | GCTCACGC |
| Cipher7-050 | ATCTGTAT |
| Cipher7-051 | CGTTCGCA |
| Cipher7-052 | TACCTATG |
| Cipher7-053 | TGAGTTAA |
| Cipher7-054 | CAGACCGG |
| Cipher7-055 | GCCGGACA |
| Cipher7-056 | ATTAAGTG |
| Cipher7-057 | CCGCTTCC |
| Cipher7-058 | TTATCCTT |
| Cipher7-059 | AACGAGAA |
| Cipher7-060 | GGTAGAGG |
| Cipher7-061 | TCGTCGGC |
| Cipher7-062 | CTACTAAT |
| Cipher7-063 | GGCACCTC |
| Cipher7-064 | AATGTTCT |

TABLE 2

15 Index Set Including Subsets (Index Groups 0-3)

| Index Label | Index Sequence |
| --- | --- |
| Index Group #0 | |
| Cipher5-001 | TCACCGAC |
| Cipher5-002 | CTGTTAGT |
| Cipher5-003 | AGCAATTA |
| Cipher5-004 | GATGGCCG |
| Cipher5-005 | CGTGCGGA |
| Cipher5-006 | TACATAAG |
| Cipher5-007 | TGCTGTGC |
| Cipher5-008 | CATCACAT |
| Cipher5-009 | AGAACACC |
| Cipher5-010 | GAGGTGTT |
| Cipher5-011 | AGGTTCAA |
| Cipher5-012 | GAACCTGG |
| Index Group #1 | |
| Cipher5-013 | TCGTTCTT |
| Cipher5-014 | CTACCTCC |
| Cipher5-015 | GATGAGAA |
| Cipher5-016 | AGCAGAGG |
| Cipher5-017 | GCTCGATC |
| Cipher5-018 | ATCTAGCT |
| Cipher5-019 | TTAATGGA |
| Cipher5-020 | CCGGCAAG |
| Cipher5-021 | CACTGTTA |
| Cipher5-022 | TGTCACCG |
| Cipher5-023 | AATTCCGA |
| Cipher5-024 | GGCCTTAG |
| Index Group #2 | |
| Cipher5-025 | GAGACAGA |
| Cipher5-026 | AGAGTGAG |
| Cipher5-027 | CCGTGGTC |
| Cipher5-028 | TTACAACT |
| Cipher5-029 | GTATCCAC |
| Cipher5-030 | ACGCTTGT |
| Cipher5-031 | TGTAAGGC |
| Cipher5-032 | CACGGAAT |
| Cipher5-033 | TCCGTTAA |
| Cipher5-034 | CTTACCGG |
| Cipher5-035 | CCTTCTCA |
| Cipher5-036 | TTCCTCTG |
| Index Group #3 | |
| Cipher5-037 | CGACGAGC |
| Cipher5-038 | TAGTAGAT |
| Cipher5-039 | ATCGTCCA |
| Cipher5-040 | GCTACTTG |
| Cipher5-041 | GAGCTTCC |
| Cipher5-042 | AGATCCTT |
| Cipher5-043 | TTCAGGTC |
| Cipher5-044 | CCTGAACT |
| Cipher5-045 | CGGATTGA |
| Cipher5-046 | TAAGCCAG |
| Cipher5-047 | TGAGATCA |
| Cipher5-048 | CAGAGCTG |

In some implementations, the index sequence on a first strand of the adapter and the index sequence on a second strand of the adapter are both selected from a same subset among multiple subsets of the set of index sequences. In some implementations, the subset of index sequences is one of the subsets (labeled by plate numbers) of the index sequences in Table 3.

TABLE 3

15 and 17 Index Set Including Subsets (Plates 1-4)

| Index Label | Index Sequence | Index Subtype |
|---|---|---|
| Plate 1 | | |
| Wheatstone7-001 | GAACCGCG | I7 |
| Wheatstone7-002 | AGGTTATA | I7 |
| Wheatstone7-003 | TCATCCTT | I7 |
| Wheatstone7-004 | CTGCTTCC | I7 |
| Wheatstone7-005 | GGTCACGA | I7 |
| Wheatstone7-006 | AACTGTAG | I7 |
| Wheatstone7-007 | GTGAATAT | I7 |
| Wheatstone7-008 | ACAGGCGC | I7 |
| Wheatstone7-009 | CATAGAGT | I7 |
| Wheatstone7-010 | TGCGAGAC | I7 |
| Wheatstone7-011 | GACGTCTT | I7 |
| Wheatstone7-012 | AGTACTCC | I7 |
| Wheatstone7-013 | TGGCCGGT | I7 |
| Wheatstone7-014 | CAATTAAC | I7 |
| Wheatstone7-015 | ATAATGTG | I7 |
| Wheatstone7-016 | GCGGCACA | I7 |
| Wheatstone5-001 | CTAGCGCT | I5 |
| Wheatstone5-002 | TCGATATC | I5 |
| Wheatstone5-003 | CGTCTGCG | I5 |
| Wheatstone5-004 | TACTCATA | I5 |
| Wheatstone5-005 | ACGCACCT | I5 |
| Wheatstone5-006 | GTATGTTC | I5 |
| Wheatstone5-007 | CGCTATGT | I5 |
| Wheatstone5-008 | TATCGCAC | I5 |
| Wheatstone5-009 | TCTGTTGG | I5 |
| Wheatstone5-010 | CTCACCAA | I5 |
| Wheatstone5-011 | TATTAGCT | I5 |
| Wheatstone5-012 | CGCCGATC | I5 |
| Wheatstone7-017 | TCTCTACT | I7 |
| Wheatstone7-018 | CTCTCGTC | I7 |
| Wheatstone7-019 | CCAAGTCT | I7 |
| Wheatstone7-020 | TTGGACTC | I7 |
| Wheatstone7-021 | GGCTTAAG | I7 |
| Wheatstone7-022 | AATCCGGA | I7 |
| Plate 2 | | |
| Wheatstone7-023 | TAATACAG | I7 |
| Wheatstone7-024 | CGGCGTGA | I7 |
| Wheatstone7-025 | ATGTAAGT | I7 |
| Wheatstone7-026 | GCACGGAC | I7 |
| Wheatstone7-027 | GGTACCTT | I7 |
| Wheatstone7-028 | AACGTTCC | I7 |
| Wheatstone7-029 | GCAGAATT | I7 |
| Wheatstone7-030 | ATGAGGCC | I7 |
| Wheatstone7-031 | ACTAAGAT | I7 |
| Wheatstone7-032 | GTCGGAGC | I7 |
| Wheatstone5-013 | CCGCGGTT | I5 |
| Wheatstone5-014 | TTATAACC | I5 |
| Wheatstone5-015 | GGACTTGG | I5 |
| Wheatstone5-016 | AAGTCCAA | I5 |
| Wheatstone5-017 | ATCCACTG | I5 |
| Wheatstone5-018 | GCTTGTCA | I5 |
| Wheatstone5-019 | CAAGCTAG | I5 |
| Wheatstone5-020 | TGGATCGA | I5 |
| Wheatstone5-021 | AGTTCAGG | I5 |
| Wheatstone5-022 | GACCTGAA | I5 |
| Wheatstone5-023 | TGACGAAT | I5 |
| Wheatstone5-024 | CAGTAGGC | I5 |
| Wheatstone7-033 | AGCCTCAT | I7 |
| Plate 3 | | |
| Wheatstone7-034 | GATTCTGC | I7 |
| Wheatstone7-035 | TCGTAGTG | I7 |
| Wheatstone7-036 | CTACGACA | I7 |
| Wheatstone7-037 | TAAGTGGT | I7 |
| Wheatstone7-038 | CGGACAAC | I7 |
| Wheatstone7-039 | ATATGGAT | |
| Wheatstone7-040 | GCGCAAGC | I7 |
| Wheatstone7-041 | AAGATACT | I7 |
| Wheatstone7-042 | GGAGCGTC | I7 |
| Wheatstone7-043 | ATGGCATG | I7 |
| Wheatstone7-044 | GCAATGCA | I7 |
| Wheatstone7-045 | GTTCCAAT | I7 |
| Wheatstone7-046 | ACCTTGGC | I7 |
| Wheatstone7-047 | CTTATCGG | I7 |
| Wheatstone7-048 | TCCGCTAA | I7 |
| Wheatstone5-025 | GCTCATTG | I5 |
| Wheatstone5-026 | ATCTGCCA | I5 |
| Wheatstone5-027 | CTTGGTAT | I5 |
| Wheatstone5-028 | TCCAACGC | I5 |
| Wheatstone5-029 | CCGTGAAG | I5 |
| Wheatstone5-030 | TTACAGGA | I5 |
| Wheatstone5-031 | GGCATTCT | I5 |
| Wheatstone5-032 | AATGCCTC | I5 |
| Wheatstone5-033 | TACCGAGG | I5 |
| Wheatstone5-034 | CGTTAGAA | I5 |
| Wheatstone5-035 | CACGAGCG | I5 |
| Wheatstone5-036 | TGTAGATA | I5 |
| Plate 4 | | |
| Wheatstone7-049 | GATCTATC | I7 |
| Wheatstone7-050 | AGCTCGCT | I7 |
| Wheatstone7-051 | CGGAACTG | I7 |
| Wheatstone7-052 | TAAGGTCA | I7 |
| Wheatstone7-053 | TTGCCTAG | I7 |
| Wheatstone7-054 | CCATTCGA | I7 |
| Wheatstone7-055 | ACACTAAG | I7 |
| Wheatstone7-056 | GTGTCGGA | I7 |
| Wheatstone7-057 | TTCCTGTT | I7 |
| Wheatstone7-058 | CCTTCACC | I7 |
| Wheatstone7-059 | GCCACAGG | I7 |
| Wheatstone7-060 | ATTGTGAA | I7 |
| Wheatstone7-061 | ACTCGTGT | I7 |
| Wheatstone7-062 | GTCTACAC | I7 |
| Wheatstone7-063 | GTTCGCCG | I7 |
| Wheatstone7-064 | ACCTATTA | I7 |
| Wheatstone5-037 | ATATCTCG | I5 |
| Wheatstone5-038 | GCGCTCTA | I5 |
| Wheatstone5-039 | AACAGGTT | I5 |
| Wheatstone5-040 | GGTGAACC | I5 |
| Wheatstone5-041 | CAACAATG | I5 |
| Wheatstone5-042 | TGGTGGCA | I5 |
| Wheatstone5-043 | AGGCAGAG | I5 |
| Wheatstone5-044 | GAATGAGA | I5 |
| Wheatstone5-045 | TGCGGCGT | I5 |
| Wheatstone5-046 | CATAATAC | I5 |
| Wheatstone5-047 | GAGGATGG | I5 |
| Wheatstone5-048 | AGAAGCAA | I5 |

The set of index sequences comprised in the set of oligonucleotides includes multiple unique index sequences. In some implementations, the Hamming distance between any two index sequences of the set of index sequences is not less than the first criterion value, wherein the first criterion value is 2 or larger. The set of index sequences includes a plurality of pairs of color-balanced index sequences. Any two bases at corresponding sequence positions of each pair of color-balanced index sequences include both (i) an A base or a C base, and (i) a G base, a T base, or a U base. In some implementations, the first criterion value is 3. In some implementations, the first criterion value is 4.

In some implementations, the set of index sequences includes a plurality of non-overlapping subsets of index sequences, such as the subset shown in Tables 1-3. In these subsets, the Hamming distance between any two index sequences is not less than a second criterion value. In some implementations, the second criterion value is larger than the first criterion value. In some implementations, the first criterion value is 4 and the second criterion value is 5.

In some implementations, an oligonucleotide includes an index sequence on its 3' end and an index sequence on its 5' end. In such an implementation, the oligonucleotide may be a single stranded nucleic acid fragment with adapters attached to both ends. It may be, e.g., a denature fragment obtained from the adapter-target-adapter construct 140 shown in FIG. 1C.

In some implementations, an edit distance between any two index sequences of the set of index sequences is not less than a third criterion value. In some implementations, the third criterion value is 3. In some implementations, the edit distance is a modified Levenshtein distance where end gaps are assigned no penalty. U.S. patent application Ser. No. 15/863,737, which is incorporated herein by reference in its entirety, describes various methods of determining modified Levenshtein distance for nucleic acid sequences.

In some implementations, each index sequence of the set of index sequences has 8 bases; the first criterion value is 3; and the third criterion is 2. In some implementations, the set of index sequences comprise sequences listed hereinafter under Example 2. In some implementations, each index sequence of the set of index sequences has 10 bases; the first criterion value is 4; and the third criterion is 3. In some implementations, the set of index sequences comprise sequences listed hereinafter under Example 3.

From a bioinformatics perspective, longer oligonucleotides can provide more candidates that satisfy various constraints of interest, such as edit distance or Hamming distance. However, longer oligonucleotides are more difficult to manufacture, and would lead to undesirable reactions such as by way of self-hybridization, cross hybridization, folding, and the other side effects. On the contrary, shorter oligonucleotides, while being able to avoid in some of these side effects, may not be able to meet bioinformatics constraints such as providing a sufficiently large Hamming distance or edit distance to allow error correction. A balance between bioinformatics robustness and biochemical functions has to be considered. In some implementations, each index sequence of the set of oligonucleotides has 32 or fewer bases. In some implementations, each index sequence of the set of oligonucleotides has 16 or fewer bases. In some implementations, each index sequence of the set of oligonucleotides has 10 or fewer bases. In some implementations, each index sequence of the set of oligonucleotides has 8 or fewer bases. In some implementations, each index sequence of the set of oligonucleotides has 8 bases. In some implementations, each index sequence of the set of oligonucleotides has 7 or fewer bases. In some implementations, each index sequence of the set of oligonucleotides has 6 or fewer bases. In some implementations, each index sequence of the set of oligonucleotides has 5 or fewer bases. In some implementations, each index sequence of the set of oligonucleotides has 4 or fewer bases.

In some implementations, the set of index sequences incorporated into the index oligonucleotides excludes index sequences that were empirically determined to have poor performance of indexing sources of nucleic acid samples in multiplex massively parallel sequencing. In some implementations, the index sequences include sequences in Table 4. Other sequences not listed in Table 4 can also be excluded.

TABLE 4

Excluded Index Sequences

| Index Label | Index Sequence |
| --- | --- |
| >N501 | TAGATCGC |
| >N504 | AGAGTAGA |
| >N513 | TCGACTAG |

TABLE 4-continued

Excluded Index Sequences

| Index Label | Index Sequence |
| --- | --- |
| >N515 | TTCTAGCT |
| >N516 | CCTAGAGT |
| >N501-rc | GCGATCTA |
| >N513-rc | CTAGTCGA |
| >N515-rc | AGCTAGAA |
| >N516-rc | ACTCTAGG |
| >N504-rc | TCTACTCT |
| >N704 | TCCTGAGC |
| >N715 | ATCTCAGG |
| >N710 | CGAGGCTG |
| >N705 | GGACTCCT |
| >N709 | GCTACGCT |
| >N709-rc | AGCGTAGC |
| >N715-rc | CCTGAGAT |
| >N705-rc | AGGAGTCC |
| >N704-rc | GCTCAGGA |
| >N710-rc | CAGCCTCG |

In some implementations, the set of index sequences includes at least 12 different index sequences. In some implementations, the set of index sequences includes at least 20 different index sequences. In some implementations, the set of index sequences includes at least 24 different index sequences. In some implementations, the set of index sequences includes at least 28 different index sequences. In some implementations, the set of index sequences includes at least 48 different index sequences. In some implementations, the set of index sequences includes at least 80 or at least 96 different index sequences. In some implementations, the set of index sequences includes at least 112 or at least 384 different index sequences. In some implementations, the set of index sequences includes at least 734, at least 1,026, or at least 1,536 different index sequences.

In some implementations, the set of index sequences includes 4 subsets of 8 unique index sequences allocated as i5 sequences and 4 subsets of 12 unique index sequences allocated as i8 sequences. In some implementations, the index sequences in a subset are pairs of color-balanced sequences. In some implementations, each subset includes two more pairs of index sequences for redundancy, so that when any index needs to be replaced, pairs of color-balanced indexes can be replaced together by redundant pairs in the subset. In some implementations, the set of index sequences includes 4 subsets of 12 unique index sequences allocated as i5 sequences and 4 subsets of 16 unique index sequences allocated as i8 sequences, totaling 112 sequences.

In some implementations, the set of index sequences includes 4 subsets of index sequences, each sequence of the subset can be applied as both an i5 index sequence and an i8 index sequence.

In some implementations, the set of index sequences excludes any homopolymers having four or more consecutive identical bases. In some implementations, the set of index sequences excludes index sequences matching or reverse complementing one or more sequencing primer sequences. In some implementations, the sequencing primer sequences are comprised in the sequences of the oligonucleotides such as shown in the dual index adapter of FIG. 2A (SP1 or SP2 sequences). In some implementations, the set of index sequences excludes index sequences matching or reverse complementing one or more flow cell amplification primer sequences, such as the P5 sequence or the P7 sequence (amplification primer sequence). In some implementations, the flow cell amplification primer sequences are comprised in the sequences of the oligonucleotides, such as the P5 sequence and the P7' sequence at the 5' and 3' ends of the forked region of a Y-shaped adapter.

In some implementations, the set of index sequences excludes any subsequence of sequences of adapters or primers in an Illumina sequencing platform, or a reverse complement of the subsequence. In some implementations, the sequences of adapters or primers in the Illumina sequencing platform comprise SEQ ID NO: 1 (AGATGTGTATAAGAGACAG), SEQ ID NO: 3 (TCGTCGGCAGCGTC), SEQ ID NO: 5 (CCGAGCCCACGAGAC), SEQ ID NO: 7 (CAAGCAGAAGACGGCATACGAGAT), and SEQ ID NO: 8 (AATGATACGGCGACCACCGAGATCTACAC).

In some implementations, the set of index sequences includes index sequences having the same number of bases.

In some implementations, each index sequence of the set of index sequences has a combined number of G and C bases between 2 and 6. In some implementations, each index sequence has a guanine/cytosine (GC) content between 25% and 75%. In some implementations, the set of oligonucleotides includes DNA oligonucleotides or RNA oligonucleotides.

FIG. 2B shows a different index oligonucleotide design in which the only one strand of a Y-shaped adapter includes an index sequence. The sequencing adapter shown in FIG. 2B is similar to that in FIG. 2A, except the adapter only includes an i7 index sequence on the P7' arm of the Y-shaped adapter. The i7 index sequence is a member of the set of index sequences. The adapter does not include an index sequence on its P5 arm.

Figure 2C:
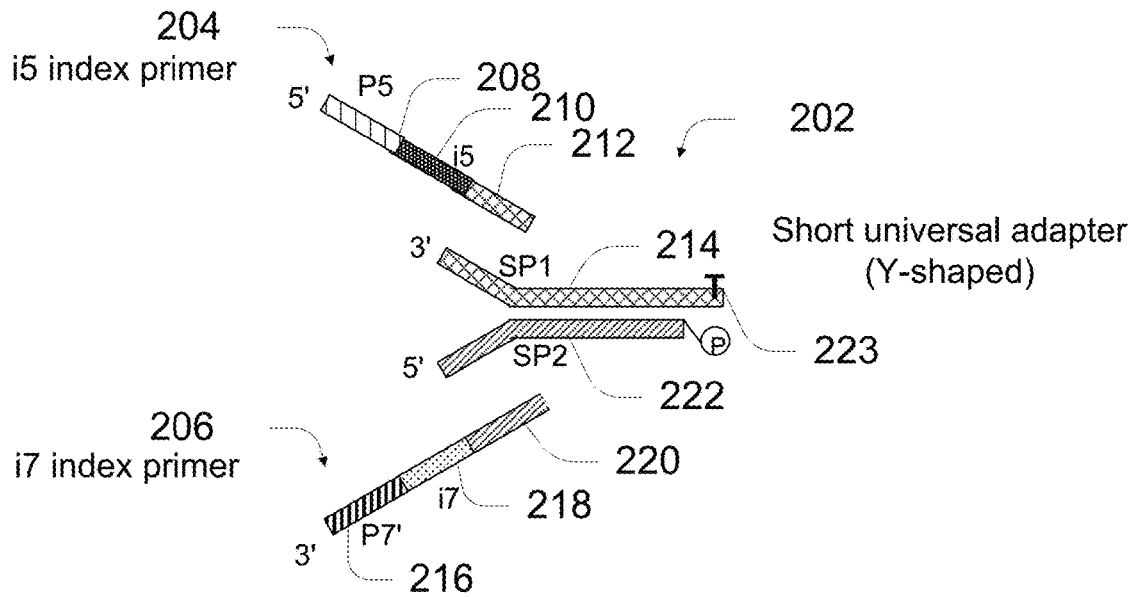

FIG. 2C shows another implementation of index oligonucleotides, in which the index sequences are incorporated into two different index primers, an i5 index primer (204) and an i7 index primer (206). The i5 index primer (204) includes an i5 index sequence that is upstream from the P5 flow cell amplification primer binding site.

The i5 index primer includes an i5 index sequence (210). The i7 index primer 206 includes an i7 index sequence. The i5 index primer 204 and the i7 index primer 206 can be hybridized to a short universal adapter 214 having a Y-shape that is similar to the Y-shaped adapters in FIGS. 2A and 2B, except that the unmatched floppy ends of the adapter 202 is shorter and do not include the index sequences or the flow cell amplification primer binding sites. Instead, the index sequences and the flow cell amplification primer binding sites are added to the adapters through the i5 index primer 204 and the i7 index primer 206 through, e.g., a nested PCR process as described in U.S. Pat. No. 8,822,150, which is incorporated herein by reference in its entirety for all purposes.

The short universal adapter 202 is universal and common for different samples, while the dual index adapter of FIG. 2A and the single index adapter of FIG. 2B are sample specific. After a short universal adapter is attached or ligated to the target nucleic acid fragment, primers including indexes can be applied to the adapter-target fragments in a sample specific manner to allow to identification of the sources of the samples. The i5 index primer 204 includes a P5 flow cell amplification primer binding site 208 at the 5' end, an i5 index sequence 210 downstream of the P5 binding set, and a primer sequence 212 downstream of the i5 index sequence. The i7 index primer 206 includes a P7' flow cell amplification primer binding site 216 at the 3' end of the primer, an i7 index sequence upstream of the P7' region, and the primer sequence 220 upstream of the i7 index sequence. When the i5 index primer 204 and i7 index primer 206 are added to a reaction mixture including the short universal adapters 202 attached to target fragments, the index sequences and the amplification primer binding sites can be incorporated into the adapter-target fragment through a PCR process (e.g., a nested PCR process) to provide sequencing libraries that include sample specific index sequences.

Figure 2D:
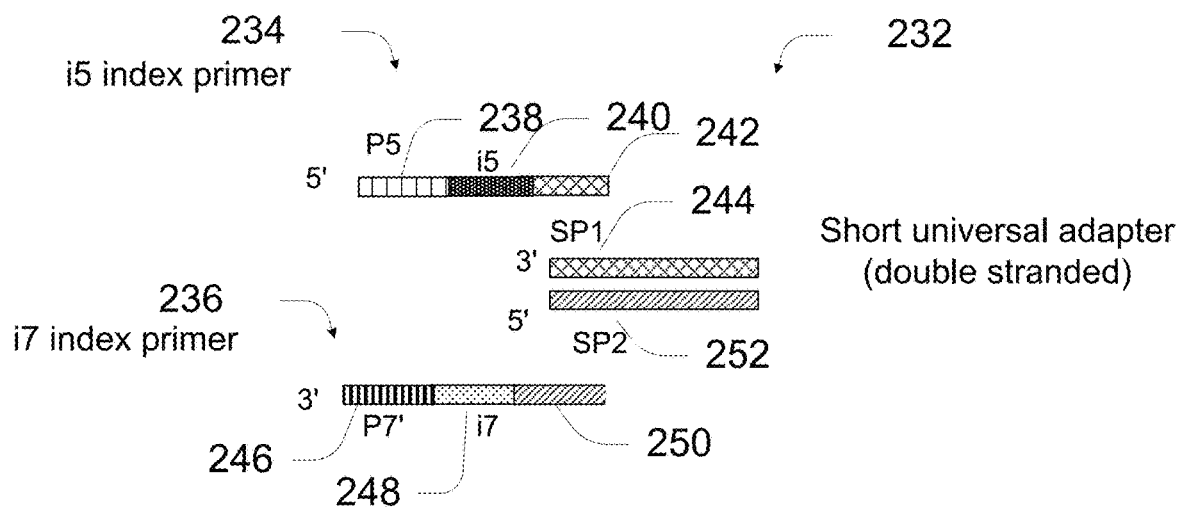

FIG. 2D shows another index oligonucleotide design involving index primers that can be used to in conjunction with double-stranded short universal adapters. The design is similar to that shown in FIG. 2C, but the short universal adapter 212 in FIG. 2D is double-stranded instead of Y-shaped as shown at the adapter 202 in FIG. 2C. Moreover, adapter 252 is blunt end without a T over-hang as adapter 202 has at 223. The i5 index primer 234 and the i7 index primer 236 can hybridize to short universal adapter 232, thereby adding relevant index sequences and amplification primer binding sites to the target sequence. The i5 index primer 234 includes a P5 flow cell litigation primer binding site 238 at the 5' end of the primer, an i5 index sequence 240 downstream of the P5 binding site, and a primer sequence 242 downstream of the i5 index sequence. The i5 index primer can attached to the SP1 sequence primer binding site 244 of the double-stranded, short universal adapter 232. The i7 index primer 236 includes a P7' flow cell amplification primer binding site 246 at the 3' end of the primer, and i7 index sequence 248 upstream of the P7' amplification primer binding site, and the primer sequence 250 upstream of the i7 index sequence. Through nested PCR reactions, i5 index primer 234 and the i7 index primer 236 can be used to incorporate the index primers and the amplification primer binding sites to the target sequence to provide a sequence library including sample specific index sequences.

Figure 4A:
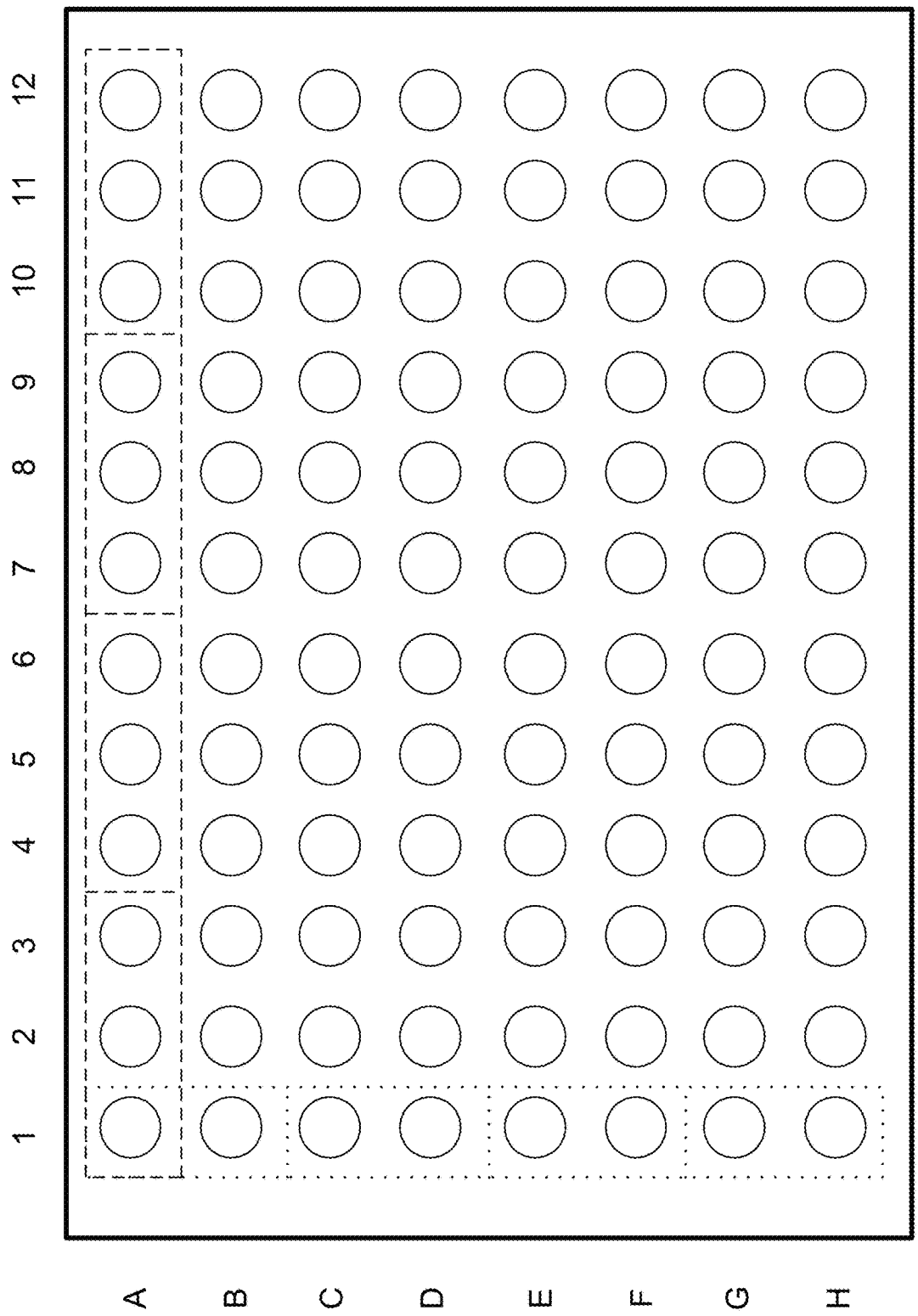

In some implementations, the set of index oligonucleotides are provided in a container including multiple separate compartments. In some implementations, the container comprises a multi-well plate. FIGS. 4A-4C schematically illustrates the multi-well plate in which index oligonucleotides can be provided. In some implementations, each compartment contains a plurality of oligonucleotides including one index sequence of the set of index sequences. The one index sequence in the compartment is different from index sequences contained in other compartments. The oligonucleotides in each compartment can be applied to nucleic acid fragments from different sources of samples to provide a mechanism to identify the sources of the samples.

In some implementations, each compartment contains a first plurality of oligonucleotides comprising the first index sequence of the set of index sequences. The compartment also contains a second plurality of oligonucleotides including a second index sequence of the set of index sequences. The ordered combination of the first plurality of oligonucleotides and the second plurality of oligonucleotides is different from ordered combinations in any other compartments. The set of polynucleotides includes the first plurality of oligonucleotides and the second plurality of oligonucleotides.

The multi-well plate shown in FIG. 4A includes an array of wells in 8 rows and 12 columns, for a total of 96 compartments. In some implementations, the array may have 16 rows and 24 columns, for a total of 384 compartments. In some implementations, the set of oligonucleotides are provided in the multi-well plate as shown in FIG. 4A, wherein each ¼ row of the compartments contain oligonucleotides including at least one pair of color balanced index sequences and each ¼ column of compartments contain oligonucleotides including at least one pair of color balanced indexes. In such a configuration, each one quarter of a row and each one quarter of a column can be used in a multiplex sequencing workflow. Therefore, the configuration enables two, three, four, six, eight, nine, and 12 plexy sequencing with full utilization of the wells.

FIG. 4B shows a layout of i5 index sequences in an 8×12 multi-well plates. Sequences are labeled such that 2n−1 and 2n (n being a positive integer) are a color-balanced pair. The i501-i508 sequences can be selected from any subset in Table 1 or Table 3.

FIG. 4C shows a layout of i7 index sequences. The i7 sequences are also organized in color balanced pairs as described above. The i701-712 sequences can be selected from any subset in Table 2 or Table 3. For both the i5 sequences and i7 sequences, when one sequence needs to be replaced for various reasons such as poor performance or experimental considerations, its color-balanced pair should also be placed. The removed color-balance pair can be replaced with another color-balanced pair from the same subset in Tables 1-3. Such replacement will maintain the color balance of the plate. The index sequence layout shown in FIGS. 4B and 4C are for the combinatorial dual index application. In other words, each well includes a first plurality of oligonucleotides including a first index sequence of the set of index sequences and a second plurality of oligonucleotides including the second index sequence of the set of index sequences. The ordered combination of the first and second oligonucleotides in each component is different from the ordered combinations of any other compartments.

In some implementations, such as the index sequence layouts illustrated in FIGS. 4B and 4C, the first plurality of oligonucleotides includes a P5 flow cell amplification primer binding site. The second plurality of oligonucleotides includes a P7' flow cell amplification primer binding site. In some implementations, such as the ones shown in FIGS. 4B and 4C, the first plurality of oligonucleotides includes an i5 index sequence and the second plurality of oligonucleotides includes an i7 index sequence.

In some implementations, the set of oligonucleotides (including the first and second plurality of oligonucleotides) are implemented as Y-shaped adapters including the index sequences, such as those in FIGS. 2A and 2B. In some implementations, the set of oligonucleotides provided in the plate includes double-stranded adapters including index sequences. In some implementations, the set of oligonucleotides includes primers including the index sequences such as the primers shown in FIGS. 2C and 2D.

In some implementations, each index sequence in the first plurality of oligonucleotides is selected from a first subset of the set of index sequences and each index sequence in the second plurality of oligonucleotides is selected from a second subset of the set of index sequences, the first subset not overlapping the second subset. In some implementations Hamming distance between any two index sequences in the first subset or between any two index sequences in the second subset is not less than a second criterion value. In some implementations, the second criterion value is larger than the first criterion value. In some implementations, the first criterion value is 4 and the second criterion value is 5. In other words, the Hamming distance between sequences in a subset is larger than the Hamming distance between sequences across subsets. In some applications, the larger Hamming distance within a subset can increase probability to identify an index sequence read including errors, such as substitution, insertion, or deletion. In some implementations, the first subset is a subset selected from Table 1 and the second subset is a subset selected from Table 2. In some implementations, the first subset includes i5 index sequences and the second subset includes i7 index sequences.

In some implementations, the index sequences are incorporated into sequencing adapters. In some implementations, the sequencing adapters include Y-shaped sequencing adapters, wherein each sequencing adapter includes a first strand including an index sequence selected from a first subset of the set of index sequences and a second strand including an index sequence selected from a second subset of the set of index sequences, the first subset not overlapping the second subset.

In some implementations, index sequences comprised in the first plurality of oligonucleotides and the second plurality of oligonucleotides are selected from a same subset of the set of index sequences. In some implementations, the Hamming distance between any two index sequences in the same subset is not less than a second criterion value. In some implementations, the second criterion value is larger than the first criterion value. In some implementations, the first criterion value is 4 and the second criterion value is 5. In some implementations, the subset is selected from a subset set forth in Table 3. In some implementations, the multiple separate compartments of the multi-well plate are arranged in an array of one or more rows of compartments and one or more columns of compartments. In some implementations, each 1/n row and/or each 1/m column of compartments contain oligonucleotides including at least one pair of color-balanced index sequences, where n and m each is selected from integers in a range of 1 to 24. In some implementations, the multiple separate compartments are arranged in an 8×12 array as shown in FIG. 4A.

Some implementations provide that the oligonucleotides consisting essentially of a plurality of subsets of oligonucleotides. The set of oligonucleotides are configured to identify sources of nucleic acid samples in multiplex massively parallel sequencing, each of the nucleic acid samples comprising a plurality of nucleic acid molecules. Each subset of the plurality of subsets of oligonucleotides includes a unique index sequence, index sequences of the plurality of subsets consisting of a set of index sequences. A Hamming distance between any two index sequences of the set of index sequences is not less than a first criterion value, wherein the first criterion value is at least 2. The set of index sequences includes a plurality of pairs of color-balanced index sequences, where any two bases at corresponding sequence positions of each pair of color-balanced index sequences include both (i) an adenine (A) base or a cytosine (C) base, and (ii) a guanine (G) base, a thymine (G) base, or a uracil (U) base.

Construction of Index Oligonucleotides

Some implementations provide methods for making a plurality of oligonucleotides for multiplex massively parallel sequencing. The method includes selecting a set of index sequences from a pool of different index sequences. The set of index sequences includes at least six different sequences. The Hamming distance between any two index sequences in the set of index sequences is not less than a first criterion value, wherein the first criterion value is at least two. The set of index sequences includes the plurality of pairs of color-balanced index sequences. Any two bases at corresponding sequence positions of each pair of color-balanced index sequences include both (i) an A base or a C base, and (i) a G base, a T base, or a U base.

Figure 5:
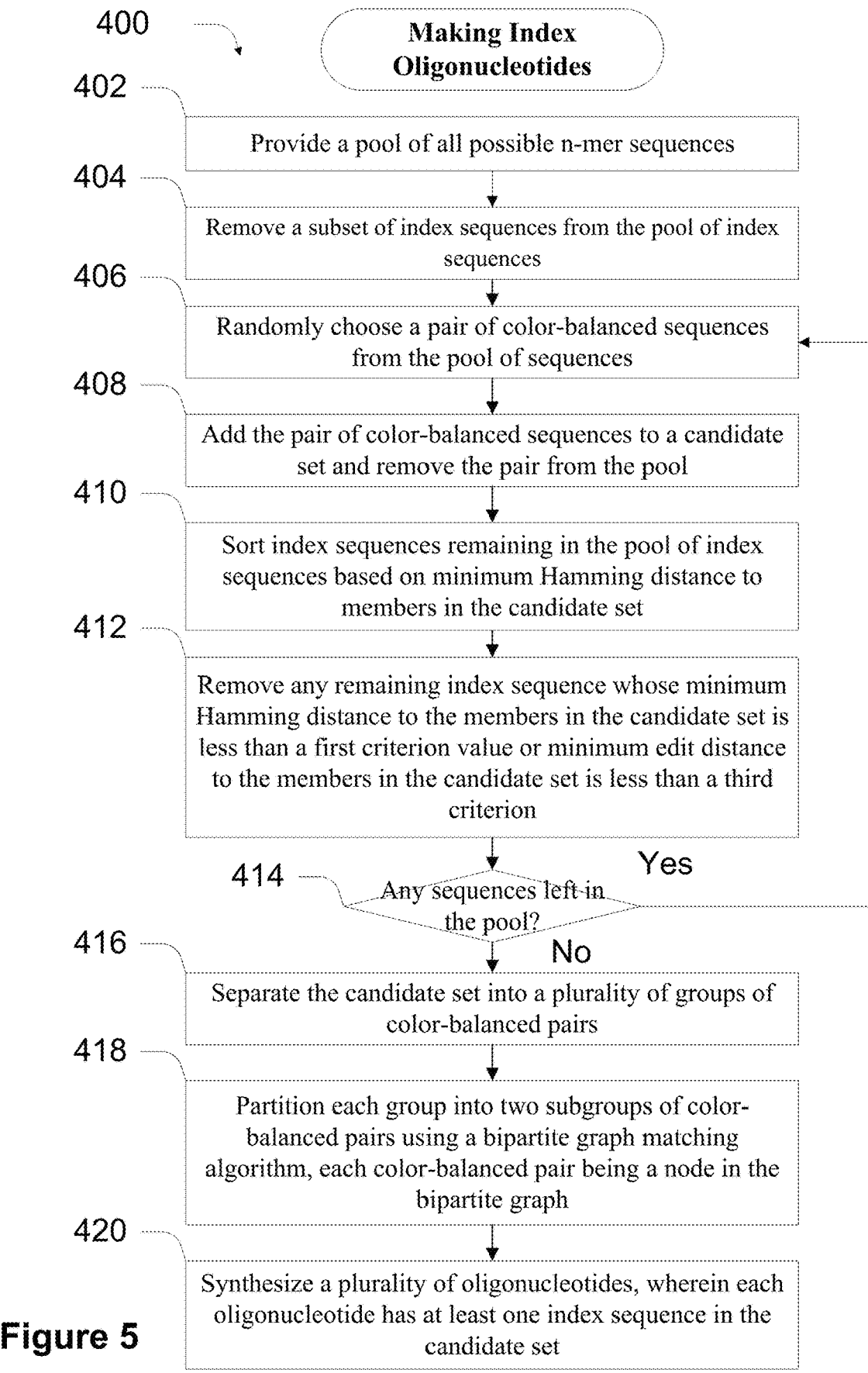
FIG. 5 shows a process for making index oligonucleotides such as indexed adapters.

In some implementations, the process for selecting a set of index sequences from the pool of different index sequences is in accordance with steps 402-416 of process 400 in FIG. 5. In some implementations, selecting the set of index sequences from the pool of different index sequences includes selecting a candidate set of index sequences from the pool of index sequences, separating the selected candidate set into a plurality of groups of color-balanced pairs of index sequences, and petitioning each group into two subgroups of color balanced pairs using a bipartite graph matching algorithm. Each color balanced pair is a node in the bipartite graph.

FIG. 5 shows a process 400 for making index oligonucleotides such as indexed adapters. Process 400 involves providing a pool of all possible n-mer sequences. In some implementations, the n-mers are 8-mers. In some implementations, the n-mers are 9-mers. In some implementations, the n-mers are 10-mers. Oligonucleotides of other sizes described herein may be similarly generated. See block 402. Process 400 further involves removing a subset of index sequences from the pool of index sequences. See block 404. In some implementations, the removed subset of index sequences includes index sequences having four or more consecutive identical bases. In some implementations, the removed subset of index sequences includes index sequences having the combined number of G and C bases smaller than two and oligonucleotide sequences having a combined number of G and C bases larger than six. In some implementations, the removed subset of index sequences includes index sequences having a sequence matching or reverse complementing one or more sequencing primer sequences. In some implementations, the sequencing primer sequences are included in the sequences of the index oligonucleotides, such as the adapters and primers shown in FIGS. 2A-2D. In some implementations, the removed subset of index sequences includes index sequences having a sequence matching or reverse complementing one or more flow cell amplification primer sequences. In some implementations, the flow cell amplification primer sequences are included in the sequences of the index oligonucleotides, such as the P5 and P7' sequences in the adapters and primers shown in FIGS. 2A-2D. In some implementations, the removed subset of index sequences includes index sequences that were empirically determined to have poor performance in indexing sources of nucleic acid samples in multiplex massively parallel sequencing. In some implementations, the removed subset of index sequences includes sequences in Table 4.

Process 400 proceeds by randomly choosing a pair of color-balanced sequences from the pool of sequences. See block 406. Process 400 further involves adding the pair of color-balanced sequences to a candidate set, and removing the pair from the pool. See block 408. Process 410 involves sorting index sequences remaining in the pool of index sequences based on minimum Hamming distance to members in the candidates set. See block 410. Process 400 further involves removing any remaining index sequence whose minimum Hamming distance to the members in the candidates set is less than a first criterion value or minimum edit distance to the members in the candidates set is less than a third criterion. In some implementations, the first criterion value is 4 and the third criterion value is 3. See block 412.

Process 410 further involves deciding whether any sequences are left it in the pool. See block 44. If so, the process loops back to block 406 to randomly choose a pair of color-balanced sequences from the pool of sequences. See the "Yes" branch of decision block 414. If no more sequences are left in the pool, process 400 proceeds to separate the candidate set into a plurality of groups of color-balanced pairs. See block 416. In some implementations, the separation is performed by randomly selecting a seed for each of the plurality of groups, and greedily expanding each of the plurality of groups. The greedy approach involves having each group take turn in taking a most distant color-balanced pair remaining in the pool.

Process 400 further involves petitioning each group into two subgroups of color-balanced pairs using a bipartite graph matching algorithm, each color-balanced pair of index sequences being a nod in the bipartite graph. In the bipartite graph matching algorithm, two nodes are connected to if the Hamming distance between two nodes is less than a second criterion value, wherein the second criterion value is larger than the first criterion value. The matching algorithm results in two groups of index sequences. In some implementations, the first criterion value is 4 and the second criterion value is 5. One group can be used to as i5 index sequences and another group i7 index sequences in some implementations.

Process 400 then involves synthesizing the plurality of oligonucleotides, wherein each oligonucleotide has at least one index sequence in the candidates set. In some implementations, the plurality of oligonucleotides includes double-stranded sequencing adapters, wherein each strand of each double-stranded sequencing adapter includes an index sequence of the set of index sequences. In some implementations, a double-stranded sequencing adapter includes a first strand including an index sequence selected from the first subset of the set of index sequences and a second strand including an index sequence selected from a second subset of the set of index sequences, the first subset not overlapping the second subject. In some implementations, the first strand of each double-stranded sequencing adapter includes a P5 flow cell amplification primer binding site, and the second strand of each double-strict sequencing adapter includes a P7' flow cell amplification primer binding site. Other forms of oligonucleotides described herein can be synthesized.

Samples

Samples that are used for determining DNA fragment sequence can include samples taken from any cell, fluid, tissue, or organ including nucleic acids in which sequences of interest are to be determined. In some embodiments involving diagnosis of cancers, circulating tumor DNA may be obtained from a subject's bodily fluid, e.g. blood or plasma. In some embodiments involving diagnosis of fetus, it is advantageous to obtain cell-free nucleic acids, e.g., cell-free DNA (cfDNA), from maternal body fluid. Cell-free nucleic acids, including cell-free DNA, can be obtained by various methods known in the art from biological samples including but not limited to plasma, serum, and urine (see, e.g., Fan et al., *Proc Natl Acad Sci* 105:16266-16271 [2008]; Koide et al., *Prenatal Diagnosis* 25:604-607 [2005]; Chen et al., *Nature Med.* 2: 1033-1035 [1996]; Lo et al., *Lancet* 350: 485-487 [1997]; Botezatu et al., *Clin Chem.* 46: 1078-1084, 2000; and Su et al., *J Mol. Diagn.* 6: 101-107 [2004]).

In various embodiments the nucleic acids (e.g., DNA or RNA) present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample is un-enriched for DNA.

The samples including the nucleic acids to which the methods described herein are applied typically include a biological sample ("test sample") as described above. In some embodiments, the nucleic acids to be sequenced are purified or isolated by any of a number of well-known methods.

Accordingly, in certain embodiments the sample includes or consists essentially of a purified or isolated polynucleotide, or it can include samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, stool, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can include two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent, and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acids from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

Sequencing Library Preparation

In various embodiments, sequencing may be performed on various sequencing platforms that require preparation of a sequencing library. The preparation typically involves fragmenting the DNA (sonication, nebulization or shearing), followed by DNA repair and end polishing (blunt end or A overhang), and platform-specific adapter ligation. In one embodiment, the methods described herein can utilize next generation sequencing technologies (NGS), that allow multiple samples to be sequenced individually as genomic molecules (i.e., single-plex sequencing) or as pooled samples comprising indexed genomic molecules (e.g., multiplex sequencing) on a single sequencing run. These methods can generate up to several billion reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as noncoding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Paired end reads may be used for the sequencing methods and systems disclosed herein. The fragment or insert length is longer than the read length, and sometimes longer than the sum of the lengths of the two reads.

In some illustrative embodiments, the sample nucleic acid(s) are obtained as genomic DNA, which is subjected to fragmentation into fragments of longer than approximately 50, 100, 200, 300, 400, 500, 600, 700, 800, 900, 1000, 2000, or 5000 base pairs, to which NGS methods can be readily applied. In some embodiments, the paired end reads are obtained from inserts of about 100-5000 bp. In some embodiments, the inserts are about 100-1000 bp long. These are sometimes implemented as regular short-insert paired end reads. In some embodiments, the inserts are about 1000-5000 bp long. These are sometimes implemented as long-insert mate paired reads as described above.

In some implementations, long inserts are designed for evaluating very long sequences. In some implementations, mate pair reads may be applied to obtain reads that are spaced apart by thousands of base pairs. In these implementations, inserts or fragments range from hundreds to thousands of base pairs, with two biotin junction adapters on the two ends of an insert. Then the biotin junction adapters join the two ends of the insert to form a circularized molecule, which is then further fragmented. A sub-fragment including the biotin junction adapters and the two ends of the original insert is selected for sequencing on a platform that is designed to sequence shorter fragments.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, *J Biol. Chem* 265:17323-17333 [1990]; Richards and Boyer, *J Mol Biol* 11:327-240 [1965]) which may need to be repaired as they may lack the requisite 5'-phosphate for the subsequent enzymatic reactions, e.g., ligation of sequencing adapters, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described in the example workflow above with reference to FIGS. 1A and 1B, instruct users to end-repair sample DNA, to purify the end-repaired products prior to adenylating or dA-tailing the 3' ends, and to purify the dA-tailing products prior to the adapter-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in U.S. Patent Pub. No. 2013/0029852 A1, which is incorporated herein by reference by its entirety.

Sequencing Methods

The methods and apparatus described herein may employ next generation sequencing technology (NGS), which allows massively parallel sequencing. In certain embodiments, clonally amplified DNA templates or single DNA molecules are sequenced in a massively parallel fashion within a flow cell (e.g., as described in Volkerding et al. *Clin Chem* 55:641-658 [2009]; Metzker M *Nature Rev* 11:31-46 [2010]). The sequencing technologies of NGS include but are not limited to pyrosequencing, sequencing-by-synthesis with reversible dye terminators, sequencing by oligonucleotide probe ligation, and ion semiconductor sequencing. DNA from individual samples can be sequenced individually (i.e., single-plex sequencing) or DNA from multiple samples can be pooled and sequenced as indexed genomic molecules (i.e., multiplex sequencing) on a single sequencing run, to generate up to several hundred million reads of DNA sequences. Examples of sequencing technologies that can be used to obtain the sequence information according to the present method are further described here.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In some embodiments, the disclosed methods involve obtaining sequence information for the nucleic acids in the test sample by massively parallel sequencing of millions of DNA fragments using Illumina's sequencing-by-synthesis and reversible terminator-based sequencing chemistry (e.g. as described in Bentley et al., *Nature* 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA or circulating tumor DNA (ctDNA) is used as the template, and fragmentation is not required as cfDNA or ctDNA exists as short fragments. For example fetal cfDNA circulates in the bloodstream as fragments approximately 170 base pairs (bp) in length (Fan et al., *Clin Chem* 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos. Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free genomic library preparation is used, and the randomly fragmented genomic DNA is enriched using the cluster amplification alone (Kozarewa et al., *Nature Methods* 6:291-295 [2009]). In some applications, the templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adapters attached to the two ends of the fragment, the adapters allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced from both ends is also referred to as an insert.

In some implementation, a flow cell for clustering in the Illumina platform is a glass slide with lanes. Each lane is a glass channel coated with a lawn of two types of oligos (e.g., P5 and P7' oligos). Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification and other sequencing methods involving clustering, a strand folds over, and a second adapter region on a second end of the strand hybridizes with the second type of oligos on the flow cell surface. A polymerase generates a complementary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves 2 reads from the two ends of a fragment. Paired end reads are used to resolve ambiguous alignments. Paired-end sequencing allows users to choose the length of the insert (or the fragment to be sequenced) and sequence either end of the insert, generating high-quality, alignable sequence data. Because the distance between each paired read is known, alignment algorithms can use this information to map reads over repetitive regions more precisely. This results in better alignment of the reads, especially across difficult-to-sequence, repetitive regions of the genome.

Paired-end sequencing can detect rearrangements, including insertions and deletions (indels) and inversions.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is specifically referred to as mate pair reads. In some embodiments involving mate pair reads, two biotin junction adapters first are attached to two ends of a relatively long insert (e.g., several kb). The biotin junction adapters then link the two ends of the insert to form a circularized molecule. A sub-fragment encompassing the biotin junction adapters can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following address, which is incorporated by reference in its entirety: www dot illumina dot com/documents/products/technotes/technote_nextera_matepair_data_processing.pdf.

After sequencing of DNA fragments, sequence reads of predetermined length, e.g., 100 bp, are localized by mapping (alignment) to a known reference genome. The mapped reads and their corresponding locations on the reference sequence are also referred to as tags. In another embodiment of the procedure, localization is realized by k-mer sharing and read-read alignment. The analyses of many embodiments disclosed herein make use of reads that are either poorly aligned or cannot be aligned, as well as aligned reads (tags). In one embodiment, the reference genome sequence is the NCBI36/hg18 sequence, which is available on the World Wide Web at genome dot ucsc dot edu/cgi-bin/hgGateway?org=Human&db=hg18&hgsid=166260105). Alternatively, the reference genome sequence is the GRCh37/hg19 or GRCh38, which is available on the World Wide Web at genome dot ucsc dot edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., *Genome Biology* 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

Other sequencing methods may also be used to obtain sequence reads and alignments thereof. Additional suitable methods are described in U.S. Patent Pub. No. 2016/0319345 A1, which is incorporated herein by reference in its entirety.

In some embodiments of the methods described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In some embodiments, paired end reads are used to determine sequences of interest, which comprise sequence reads that are about 20 bp to 1000 bp, about 50 bp to 500 bp, or 80 bp to 150 bp. In various embodiments, the paired end reads are used to evaluate a sequence of interest. The sequence of interest is longer than the reads. In some embodiments, the sequence of interest is longer than about 100 bp, 500 bp, 1000 bp, or 4000 bp. Mapping of the sequence reads is achieved by comparing the sequence of the reads with the sequence of the reference to determine the chromosomal origin of the sequenced nucleic acid molecule, and specific genetic sequence information is not needed. A small degree of mismatch (0-2 mismatches per read) may be allowed to account for minor polymorphisms that may exist between the reference genome and the genomes in the mixed sample. In some embodiments, reads that are aligned to the reference sequence are used as anchor reads, and reads paired to anchor reads but cannot align or poorly align to the reference are used as anchored reads. In some embodiments, poorly aligned reads may have a relatively large number of percentage of mismatches per read, e.g., at least about 5%, at least about 10%, at least about 15%, or at least about 20% mismatches per read.

A plurality of sequence tags (i.e., reads aligned to a reference sequence) are typically obtained per sample. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags of, e.g., 100 bp, are obtained from mapping the reads to the reference genome per sample. In some embodiments, all the sequence reads are mapped to all regions of the reference genome, providing genome-wide reads. In other embodiments, reads mapped to a sequence of interest.

Apparatus and Systems for Making Index Oligonucleotides

As should be apparent, certain embodiments of the invention employ processes acting under control of instructions and/or data stored in or transferred through one or more computer systems. Certain embodiments also relate to an apparatus for performing these operations. This apparatus may be specially designed and/or constructed for the required purposes, or it may be a general-purpose computer selectively configured by one or more computer programs and/or data structures stored in or otherwise made available to the computer. In particular, various general-purpose machines may be used with programs written in accordance with the teachings herein, or it may be more convenient to construct a more specialized apparatus to perform the required method steps. A particular structure for a variety of these machines is shown and described below.

Certain embodiments also provide functionality (e.g., code and processes) for storing any of the results (e.g., query results) or data structures generated as described herein. Such results or data structures are typically stored, at least temporarily, on a computer readable medium. The results or data structures may also be output in any of various manners such as displaying, printing, and the like.

Examples of tangible computer-readable media suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves).

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine. The code may specify input, output, calculations, conditionals, branches, iterative loops, etc.

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

One implementation provides a system for use in determining a sequence in multiple test samples including nucleic acids, the system including a sequencer for receiving nucleic acid samples and providing nucleic acid sequence information from the samples; a processor; and a machine readable storage medium having stored thereon instructions for execution on said processor to determine a sequence of interest in the test sample by the method described above.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

Another implementation provides a system including nucleic acid synthesizer, a processor, and a machine readable storage medium having stored thereon instructions for execution on said processor to prepare sequencing adapters. The instructions includes: (a) code for adding to a candidate set of index sequences a randomly chosen pair of color-balanced index sequences from a pool of different index sequences, wherein any two bases at corresponding sequence positions of each pair of color-balanced index sequences include both (i) an adenine base or a cytosine base, and (ii) a guanine base, a thymine base, or a uracil base; (b) code for sorting index sequences remaining in the pool of index sequences based on minimum Hamming distance to members in the candidate set; (c) code for removing any remaining index sequence whose minimum Hamming distance to the members in the candidate set is less than a first criterion value or minimum edit distance to the members in the candidate set is less than a second criterion value; (d) code for repeating (a)-(c) to maximize a size of the candidate set; and (e) code for selecting from the candidate set the set of index sequences to be incorporated into the set of oligonucleotides configured to be used in multiplex massively parallel sequencing.

In some implementations, the instructions includes: (a) code for receiving a plurality of index reads and a plurality of target reads of target sequences obtained from target nucleic acids derived from the plurality of samples, wherein each target read comprises a target sequence obtained from a target nucleic acid derived from a sample of the plurality of samples, each index read comprises an index sequence obtained from a target nucleic acid derived from a sample of the plurality of samples, the index sequence being selected from a set of index sequences, each target read is associated with at least one index read, each sample of the plurality of samples is uniquely associated with one or more index sequences of the set of index sequences, and a Hamming distance between any two index sequences of the set of index sequences is not less than a first criterion value, wherein the first criterion value is at least 2; (b) code for identifying, among the plurality of target reads, a subset of target reads associated with index reads aligned to at least one index sequence uniquely associated with a particular sample of the plurality of samples; and (c) code for determining a target sequence for the particular sample based on the identified subset of target reads.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, reference sequences (including reference sequences providing solely or primarily polymorphisms), calls such as cancer diagnosis calls, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the sequence of a DNA fragment of interest in test samples. The computer product may contain instructions for performing any one or more of the above-described methods for determining a sequence of interest. As explained, the computer product may include a non-transitory and/or tangible computer readable medium having a computer executable or compilable logic (e.g., instructions) recorded thereon for enabling a processor to determine a sequence of interest. In one example, the computer product comprises a computer readable medium having a computer executable or compilable logic (e.g., instructions) recorded thereon for enabling a processor to diagnose a condition or determine a nucleic acid sequence of interest.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable calls of low allele frequency mutations generally require mapping thousands (e.g., at least about 10,000) or even millions of reads to one or more chromosomes.

The methods disclosed herein can be performed using a system for determining a sequence of interest in multiple test samples. The system may include: (a) a sequencer for receiving nucleic acids from the test sample providing nucleic acid sequence information from the sample; (b) a processor; and (c) one or more computer-readable storage media having stored thereon instructions for execution on said processor to determining a sequence of interest in the test sample. In some embodiments, the methods are instructed by a computer-readable medium having stored thereon computer-readable instructions for carrying out a method for determining the sequence of interest. Thus one embodiment provides a computer program product including a non-transitory machine readable medium storing program code that, when executed by one or more processors of a computer system, causes the computer system to implement a method for determining the sequences of nucleic acid fragments in multiple test samples.

In some embodiments, the program codes or the instructions may further include automatically recording information pertinent to the method. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the test sample was taken. This may involve performing one or more additional tests or analyses on additional samples taken from the subject.

Disclosed methods can also be performed using a computer processing system which is adapted or configured to perform a method for determining a sequence of interest. One embodiment provides a computer processing system which is adapted or configured to perform a method as described herein. In one embodiment, the apparatus includes a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

a) Reads obtained by sequencing nucleic acids in a test sample
b) Tags obtained by aligning reads to a reference genome or other reference sequence or sequences
c) The reference genome or sequence
d) Thresholds for calling a test sample as either affected, non-affected, or no call
e) The actual calls of medical conditions related to the sequence of interest
f) Diagnoses (clinical condition associated with the calls)
g) Recommendations for further tests derived from the calls and/or diagnoses
h) Treatment and/or monitoring plans derived from the calls and/or diagnoses These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to determine a sequence of interest. At this remote location, as an example, the reads are aligned to a reference sequence to produce anchor and anchored reads. Among the processing operations that may be employed at distinct locations are the following:

a) Sample collection
b) Sample processing preliminary to sequencing
c) Sequencing
d) Analyzing sequence data and deriving medical calls
e) Diagnosis
f) Reporting a diagnosis and/or a call to patient or health care provider
g) Developing a plan for further treatment, testing, and/or monitoring
h) Executing the plan
i) Counseling Any one or more of these operations may be automated as described elsewhere herein. Typically, the sequencing and the analyzing of sequence data and deriving medical calls will be performed computationally. The other operations may be performed manually or automatically.

Figure 6:
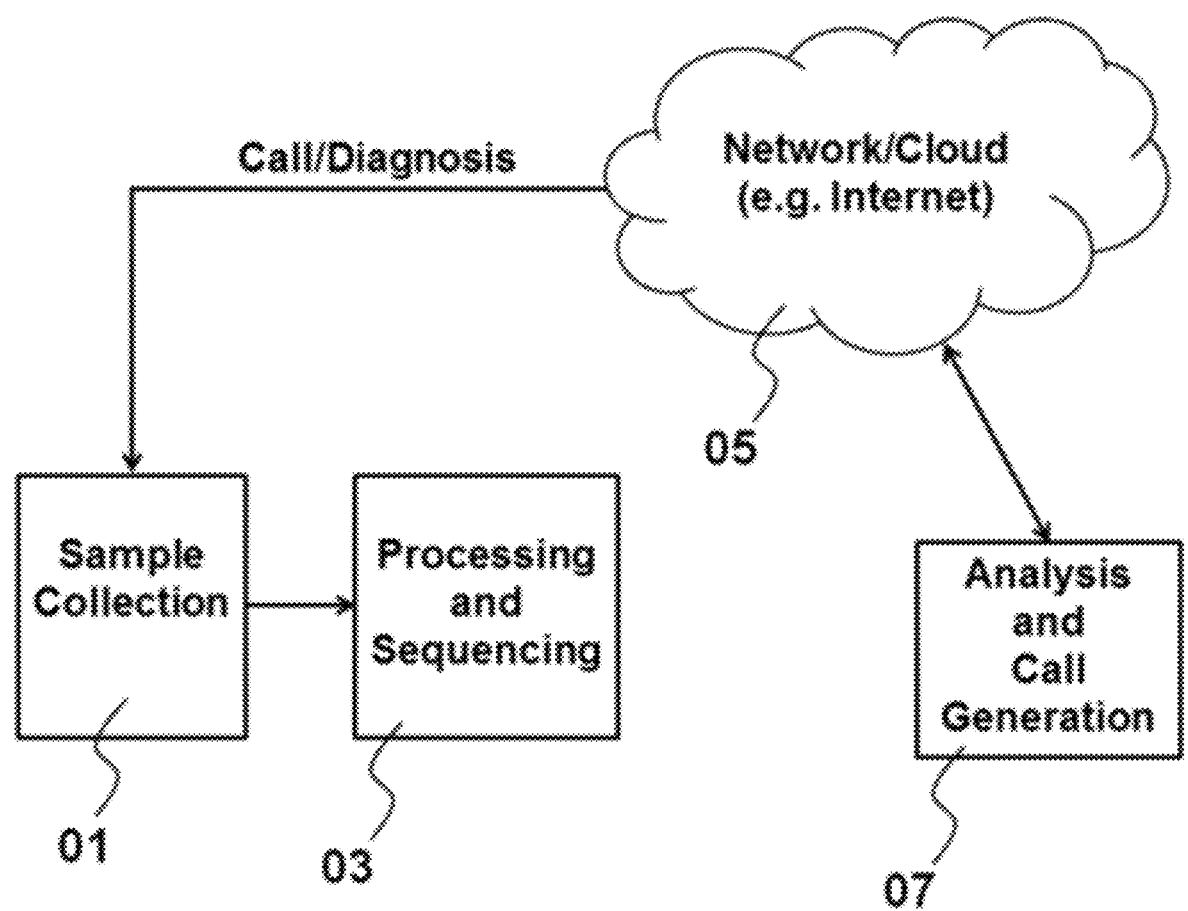
FIG. 6 shows one implementation of a dispersed system for producing a call or diagnosis from test samples.

FIG. 6 shows one implementation of a dispersed system for producing a call or diagnosis from multiple test samples. A sample collection location 01 is used for obtaining test samples. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 6.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 6. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 7:
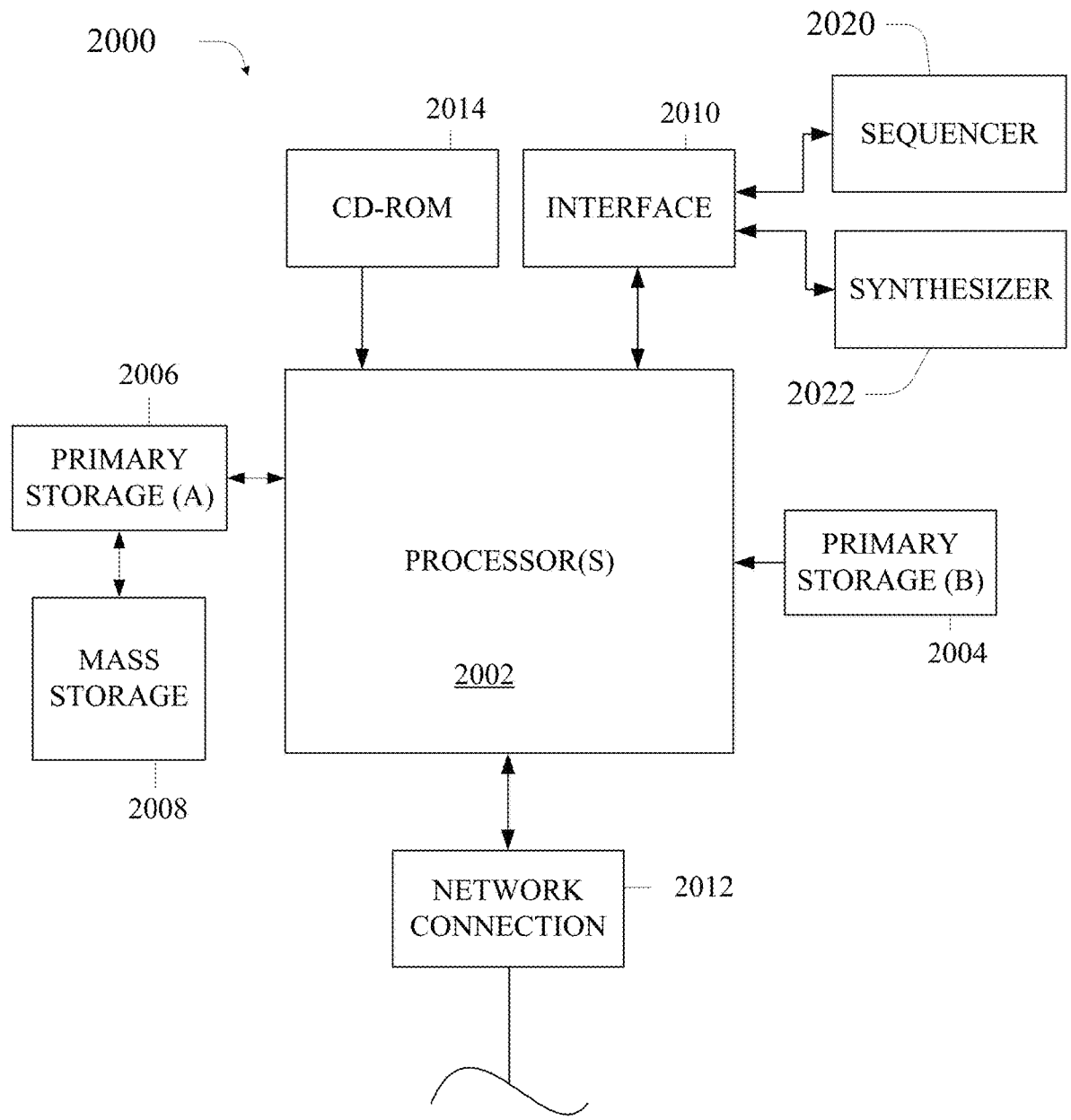
FIG. 7 illustrates a computer system that can serve as a computational apparatus according to certain embodiments.

FIG. 7 illustrates, in simple block format, a typical computer system that, when appropriately configured or designed, can serve as a computational apparatus according to certain embodiments. The computer system 2000 includes any number of processors 2002 (also referred to as central processing units, or CPUs) that are coupled to storage devices including primary storage 2006 (typically a random access memory, or RAM), primary storage 2004 (typically a read only memory, or ROM). CPU 2002 may be of various types including microcontrollers and microprocessors such as programmable devices (e.g., CPLDs and FPGAs) and non-programmable devices such as gate array ASICs or general-purpose microprocessors. In the depicted embodiment, primary storage 2004 acts to transfer data and instructions unidirectionally to the CPU and primary storage 2006 is used typically to transfer data and instructions in a bi-directional manner. Both of these primary storage devices may include any suitable computer-readable media such as those described above. A mass storage device 2008 is also coupled bi-directionally to primary storage 2006 and provides additional data storage capacity and may include any of the computer-readable media described above. Mass storage device 2008 may be used to store programs, data and the like and is typically a secondary storage medium such as a hard disk. Frequently, such programs, data and the like are temporarily copied to primary memory 2006 for execution on CPU 2002. It will be appreciated that the information retained within the mass storage device 2008, may, in appropriate cases, be incorporated in standard fashion as part of primary storage 2004. A specific mass storage device such as a CD-ROM 2014 may also pass data unidirectionally to the CPU or primary storage.

CPU 2002 is also coupled to an interface 2010 that connects to one or more input/output devices such as such as a nucleic acid sequencer (2020), a nucleic acid synthesizer (2022), video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 2002 optionally may be coupled to an external device such as a database or a computer or telecommunications network using an external connection as shown generally at 2012. With such a connection, it is contemplated that the CPU might receive information from the network, or might output information to the network in the course of performing the method steps described herein. In some implementations, a nucleic acid sequencer or a nucleic acid synthesizer, may be communicatively linked to the CPU 2002 via the network connection 2012 instead of or in addition to via the interface 2010.

In one embodiment, a system such as computer system 2000 is used as a data import, data correlation, and querying system capable of performing some or all of the tasks described herein. Information and programs, including data files can be provided via a network connection 2012 for access or downloading by a researcher. Alternatively, such information, programs and files can be provided to the researcher on a storage device.

In a specific embodiment, the computer system 2000 is directly coupled to a data acquisition system such as a microarray, high-throughput screening system, or a nucleic acid sequencer (2020) that captures data from samples. Data from such systems are provided via interface 2010 for analysis by system 2000. Alternatively, the data processed by system 2000 are provided from a data storage source such as a database or other repository of relevant data. Once in apparatus 2000, a memory device such as primary storage 2006 or mass storage 2008 buffers or stores, at least temporarily, relevant data. The memory may also store various routines and/or programs for importing, analyzing and presenting the data, including selecting and or verifying index sequences, codes for determining sequence reads, and correcting errors in reads, etc.

In certain embodiments, the computers used herein may include a user terminal, which may be any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms.

In certain embodiments, the computers used herein may also include a server system in communication with a user terminal, which server system may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

EXPERIMENTAL

Example 1

Index Sequences Verification

In silico experiments were carried out to verify the validity and effectiveness of the index sequences according to some implementations. The index sequences satisfy the following conditions.

No direct match of index sequence with 8-mer subsequence (or reverse complement) of a sequencing platform sequencing adapters or primers
    SBS491
    P7
    P5
    SBS3
No occurrence of four nucleotide homopolymer
G/C count is 2 to 6
No sequence listed in Table 4 is used (known poor performer)
Design 1: index sequences are selected from those in Tables 1 and 2
    No two sequences have a Hamming distance <4
Designed 2: index sequences are selected from those in Table 3
    Hamming distance
        Within the 15 or 17 sequences for a given plate, the Hamming distance between any pair is >=5
        Within all sequences across the entire design (15 and 17), the Hamming distance between any pair is >=4
    Edit distance
        Within all sequences across the entire design (15 and 17), the "edit" distance between any pair is >=3

The in silico experiment generated 1 million random variations of index sequences with 3 edit operations and found no direct matches in the resulting sequences. The experiment generated 1 million random variations of index sequences having 1 deletion and 1 substitution operation and found no direct matches in the resulting sequences.

The resulting sequences were assigned to a multi-well plate layout as shown in FIG. 4. It was found that no i5/i7 pair occurred more than once. Designed pairs were color-balanced. Triples (quarter rows) were color-balanced. Quadruples (half columns) were color-balanced. Hextuples (half rows) were color-balanced. Octuples (full columns) were color-balanced. No designed pools (doubles, triples, quadruples, hextuples, octuples) had repeated pairs (i.e. they mitigate index hopping).

The experimental result demonstrate that the index sequences and index oligonucleotides provided according to some implementations can detect and correct errors in index sequence reads, thereby providing more accurate sample indexing in multiplex massively parallel sequencing.

Example 2

8-mer Index Set

This example describes the design considerations for a set of 8-mer index sequences according to some implementations and lists the sequences in the index set.

The index set supports a larger number of indices and keeps the index length at 8 bp. Compared to the index design of Example 1, the edit distance threshold was lowered to zero, and the Hamming distance threshold was lowered to 3.

The summary of the design strategy is given below.

No direct match of index sequence with 8-mer subsequence (or reverse complement) of a sequencing platform adapter or primer sequences, e.g.,
    SBS491
    P7
    P5
    SBS3
No occurrence of four nucleotide homopolymer
GC content between 25% and 75% (inclusive)
No sequence listed in Table 4 is used (known poor performer)
Minimum Hamming distance of 3
Minimum modified edit distance of 2

Indices provided as color-balanced pairs. Each pair is labeled with numbers 2n−1 and 2n, where n is a positive integer.

A total of 734 sequences are obtained as listed below. They include all the sequences tested in Example 1 and shown in Table 3.

```
scytale-001: GAACCGCG;  scytale-002: AGGTTATA;  scytale-003: TCATCCTT;
scytale-004: CTGCTTCC;  scytale-005: GGTCACGA;  scytale-006: AACTGTAG;
scytale-007: GTGAATAT;  scytale-008: ACAGGCGC;  scytale-009: CATAGAGT;
scytale-010: TGCGAGAC;  scytale-011: GACGTCTT;  scytale-012: AGTACTCC;
scytale-013: TGGCCGGT;  scytale-014: CAATTAAC;  scytale-015: ATAATGTG;
scytale-016: GCGGCACA;  scytale-017: CTAGCGCT;  scytale-018: TCGATATC;
scytale-019: CGTCTGCG;  scytale-020: TACTCATA;  scytale-021: ACGCACCT;
scytale-022: GTATGTTC;  scytale-023: CGCTATGT;  scytale-024: TATCGCAC;
scytale-025: TCTGTTGG;  scytale-026: CTCACCAA;  scytale-027: TATTAGCT;
scytale-028: CGCCGATC;  scytale-029: TCTCTACT;  scytale-030: CTCTCGTC;
scytale-031: CCAAGTCT;  scytale-032: TTGGACTC;  scytale-033: GGCTTAAG;
scytale-034: AATCCGGA;  scytale-035: TAATACAG;  scytale-036: CGGCGTGA;
scytale-037: ATGTAAGT;  scytale-038: GCACGGAC;  scytale-039: GGTACCTT;
scytale-040: AACGTTCC;  scytale-041: GCAGAATT;  scytale-042: ATGAGGCC;
scytale-043: ACTAAGAT;  scytale-044: GTCGGAGC;  scytale-045: CCGCGGTT;
scytale-046: TTATAACC;  scytale-047: GGACTTGG;  scytale-048: AAGTCCAA;
scytale-049: ATCCACTG;  scytale-050: GCTTGTCA;  scytale-051: CAAGCTAG;
scytale-052: TGGATCGA;  scytale-053: AGTTCAGG;  scytale-054: GACCTGAA;
scytale-055: TGACGAAT;  scytale-056: CAGTAGGC;  scytale-057: AGCCTCAT;
scytale-058: GATTCTGC;  scytale-059: TCGTAGTG;  scytale-060: CTACGACA;
scytale-061: TAAGTGGT;  scytale-062: CGGACAAC;  scytale-063: ATATGGAT;
scytale-064: GCGCAAGC;  scytale-065: AAGATACT;  scytale-066: GGAGCGTC;
scytale-067: ATGGCATG;  scytale-068: GCAATGCA;  scytale-069: GTTCCAAT;
scytale-070: ACCTTGGC;  scytale-071: CTTATCGG;  scytale-072: TCCGCTAA;
scytale-073: GCTCATTG;  scytale-074: ATCTGCCA;  scytale-075: CTTGGTAT;
scytale-076: TCCAACGC;  scytale-077: CCGTGAAG;  scytale-078: TTACAGGA;
scytale-079: GGCATTCT;  scytale-080: AATGCCTC;  scytale-081: TACCGAGG;
scytale-082: CGTTAGAA;  scytale-083: CACGAGCG;  scytale-084: TGTAGATA;
scytale-085: GATCTATC;  scytale-086: AGCTCGCT;  scytale-087: CGGAACTG;
scytale-088: TAAGGTCA;  scytale-089: TTGCCTAG;  scytale-090: CCATTCGA;
scytale-091: ACACTAAG;  scytale-092: GTGTCGGA;  scytale-093: TTCCTGTT;
scytale-094: CCTTCACC;  scytale-095: GCCACAGG;  scytale-096: ATTGTGAA;
scytale-097: ACTCGTGT;  scytale-098: GTCTACAC;  scytale-099: GTTCGCCG;
scytale-100: ACCTATTA;  scytale-101: ATATCTCG;  scytale-102: GCGCTCTA;
scytale-103: AACAGGTT;  scytale-104: GGTGAACC;  scytale-105: CAACAATG;
scytale-106: TGGTGGCA;  scytale-107: AGGCAGAG;  scytale-108: GAATGAGA;
scytale-109: TGCGGCGT;  scytale-110: CATAATAC;  scytale-111: GAGGATGG;
scytale-112: AGAAGCAA;  scytale-113: TAGAGCCG;  scytale-114: CGAGATTA;
```

-continued scytale-115: CCGGTCAT; scytale-116: TTAACTGC; scytale-117: TTCAGTTG;

scytale-118: CCTGACCA; scytale-119: TGAGTACG; scytale-120: CAGACGTA;

scytale-121: AACCAACA; scytale-122: GGTTGGTG; scytale-123: TCTACCAG;

scytale-124: CTCGTTGA; scytale-125: AGAGCTGT; scytale-126: GAGATCAC;

scytale-127: TAGGCAAT; scytale-128: CGAATGGC; scytale-129: ACGGTGCG;

scytale-130: GTAACATA; scytale-131: TTGTTCCT; scytale-132: CCACCTTC;

scytale-133: ACTAGACG; scytale-134: GTCGAGTA; scytale-135: TGCCATCG;

scytale-136: CATTGCTA; scytale-137: GAGCGCGT; scytale-138: AGATATAC;

scytale-139: TTCGTCAG; scytale-140: CCTACTGA; scytale-141: CGTGTATT;

scytale-142: TACACGCC; scytale-143: GTAGCCGG; scytale-144: ACGATTAA;

scytale-145: ACCGGAAT; scytale-146: GTTAAGGC; scytale-147: CACTCCGG;

scytale-148: TGTCTTAA; scytale-149: CCTGCGTG; scytale-150: TTCATACA;

scytale-151: AAGCATTC; scytale-152: GGATGCCT; scytale-153: CGCAGGAG;

scytale-154: TATGAAGA; scytale-155: CAACTCCT; scytale-156: TGGTCTTC;

scytale-157: GATGGAAG; scytale-158: AGCAAGGA; scytale-159: CAGTCTCT;

scytale-160: TGACTCTC; scytale-161: GCCTATAT; scytale-162: ATTCGCGC;

scytale-163: GTGTGTAG; scytale-164: ACACACGA; scytale-165: GCCACGCT;

scytale-166: ATTGTATC; scytale-167: CTGATTGT; scytale-168: TCAGCCAC;

scytale-169: CTACACCG; scytale-170: TCGTGTTA; scytale-171: AATGTGGC;

scytale-172: GGCACAAT; scytale-173: AGCGGAGG; scytale-174: GATAAGAA;

scytale-175: TGAAGGTT; scytale-176: CAGGAACC; scytale-177: GTATTCCG;

scytale-178: ACGCCTTA; scytale-179: CCTTACTT; scytale-180: TTCCGTCC;

scytale-181: ATTGTTGT; scytale-182: GCCACCAC; scytale-183: CAGTGGTG;

scytale-184: TGACAACA; scytale-185: TGTGCCTG; scytale-186: CACATTCA;

scytale-187: AAGCCAGT; scytale-188: GGATTGAC; scytale-189: TTGGAGAT;

scytale-190: CCAAGAGC; scytale-191: TCCTATGG; scytale-192: CTTCGCAA;

scytale-193: TACATCTG; scytale-194: CGTGCTCA; scytale-195: AGGTGCCG;

scytale-196: GAACATTA; scytale-197: CTGACATT; scytale-198: TCAGTGCC;

scytale-199: ATTAATGG; scytale-200: GCCGGCAA; scytale-201: GTGGTGGT;

scytale-202: ACAACAAC; scytale-203: ATATACCT; scytale-204: GCGCGTTC;

scytale-205: GACGCAGT; scytale-206: AGTATGAC; scytale-207: TGGACGCG;

scytale-208: CAAGTATA; scytale-209: GATTATAG; scytale-210: AGCCGCGA;

scytale-211: CCTTGCGG; scytale-212: TTCCATAA; scytale-213: ACACCGTT;

scytale-214: GTGTTACC; scytale-215: CGTCACAT; scytale-216: TACTGTGC;

scytale-217: AACGTGTG; scytale-218: GGTACACA; scytale-219: CAACGGAT;

scytale-220: TGGTAAGC; scytale-221: TCGGCGCT; scytale-222: CTAATATC;

scytale-223: GACAACCG; scytale-224: AGTGGTTA; scytale-225: TATATCGT;

scytale-226: CGCGCTAC; scytale-227: TTATCAGT; scytale-228: CCGCTGAC;

scytale-229: TCACGTCG; scytale-230: CTGTACTA; scytale-231: GTTACTTG;

scytale-232: ACCGTCCA; scytale-233: ACCAAGTG; scytale-234: GTTGGACA;

scytale-235: CGGTTAGG; scytale-236: TAACCGAA; scytale-237: AATTATCC;

-continued scytale-238: GGCCGCTT; scytale-239: GCATTGTT; scytale-240: ATGCCACC;

scytale-241: TAGAGATT; scytale-242: CGAGAGCC; scytale-243: TCACAAGG;

scytale-244: CTGTGGAA; scytale-245: GCTATTAT; scytale-246: ATCGCCGC;

scytale-247: TCTGGCCG; scytale-248: CTCAATTA; scytale-249: AATTACGA;

scytale-250: GGCCGTAG; scytale-251: AGATCAAT; scytale-252: GAGCTGGC;

scytale-253: CACACACT; scytale-254: TGTGTGTC; scytale-255: TATGCGAG;

scytale-256: CGCATAGA; scytale-257: ACAACTGG; scytale-258: GTGGTCAA;

scytale-259: GAATACGT; scytale-260: AGGCGTAC; scytale-261: AAGGAATA;

scytale-262: GGAAGGCG; scytale-263: CTCCATCT; scytale-264: TCTTGCTC;

scytale-265: GCGCCTGT; scytale-266: ATATTCAC; scytale-267: CCTGTACG;

scytale-268: TTCACGTA; scytale-269: ATTCGGTT; scytale-270: GCCTAACC;

scytale-271: TGGATAAT; scytale-272: CAAGCGGC; scytale-273: GTTAACAG;

scytale-274: ACCGGTGA; scytale-275: CAATTCTG; scytale-276: TGGCCTCA;

scytale-277: CGGCTCGT; scytale-278: TAATCTAC; scytale-279: TGGTGATG;

scytale-280: CAACAGCA; scytale-281: GTAGATGT; scytale-282: ACGAGCAC;

scytale-283: ATCCTTAG; scytale-284: GCTTCCGA; scytale-285: AACAGACC;

scytale-286: GGTGAGTT; scytale-287: ACGGCCAG; scytale-288: GTAATTGA;

scytale-289: TGCTAACT; scytale-290: CATCGGTC; scytale-291: AGATAGTT;

scytale-292: GAGCGACC; scytale-293: CTAGTAAG; scytale-294: TCGACGGA;

scytale-295: CACTGGCT; scytale-296: TGTCAATC; scytale-297: GCCTGTTG;

scytale-298: ATTCACCA; scytale-299: GTGGCTCT; scytale-300: ACAATCTC;

scytale-301: AATGTTAG; scytale-302: GGCACCGA; scytale-303: TACCAATT;

scytale-304: CGTTGGCC; scytale-305: CTAACAGG; scytale-306: TCGGTGAA;

scytale-307: TCTAATCG; scytale-308: CTCGGCTA; scytale-309: GTGATGCG;

scytale-310: ACAGCATA; scytale-311: GAATGTAT; scytale-312: AGGCACGC;

scytale-313: CGCGACAG; scytale-314: TATAGTGA; scytale-315: CCGCTTGG;

scytale-316: TTATCCAA; scytale-317: CCTACAAT; scytale-318: TTCGTGGC;

scytale-319: AGCAATAT; scytale-320: GATGGCGC; scytale-321: GAGCCATG;

scytale-322: AGATTGCA; scytale-323: TTGTGGTT; scytale-324: CCACAACC;

scytale-325: TCAGGAGT; scytale-326: CTGAAGAC; scytale-327: AAGTCGCG;

scytale-328: GGACTATA; scytale-329: ATTACACT; scytale-330: GCCGTGTC;

scytale-331: AACATTGG; scytale-332: GGTGCCAA; scytale-333: CGGCCTTG;

scytale-334: TAATTCCA; scytale-335: CCGTACCG; scytale-336: TTACGTTA;

scytale-337: AATCGAAT; scytale-338: GGCTAGGC; scytale-339: TCTCAGGT;

scytale-340: CTCTGAAC; scytale-341: TTAGGTGG; scytale-342: CCGAACAA;

scytale-343: CACGTTAT; scytale-344: TGTACCGC; scytale-345: CTACCGTG;

scytale-346: TCGTTACA; scytale-347: GTTCAGCT; scytale-348: ACCTGATC;

scytale-349: AATTAGTG; scytale-350: GGCCGACA; scytale-351: ATGAGCGT;

scytale-352: GCAGATAC; scytale-353: GCTGTCGT; scytale-354: ATCACTAC;

scytale-355: AATGTACA; scytale-356: GGCACGTG; scytale-357: TTCGAAGG;

-continued scytale-358: CCTAGGAA; scytale-359: TGATTCAT; scytale-360: CAGCCTGC;

scytale-361: AACCGCCT; scytale-362: GGTTATTC; scytale-363: AGAATTCG;

scytale-364: GAGGCCTA; scytale-365: GAGATAGG; scytale-366: AGAGCGAA;

scytale-367: CCATGATT; scytale-368: TTGCAGCC; scytale-369: AGGTGTGT;

scytale-370: GAACACAC; scytale-371: CTCGCACG; scytale-372: TCTATGTA;

scytale-373: TATTGTCG; scytale-374: CGCCACTA; scytale-375: TACACCAT;

scytale-376: CGTGTTGC; scytale-377: ACCGATAG; scytale-378: GTTAGCGA;

scytale-379: CCTCCGCT; scytale-380: TTCTTATC; scytale-381: AAGAATGA;

scytale-382: GGAGGCAG; scytale-383: GAGTTGAT; scytale-384: AGACCAGC;

scytale-385: CCAACCTG; scytale-386: TTGGTTCA; scytale-387: AGGTACAT;

scytale-388: GAACGTGC; scytale-389: CACCTGGT; scytale-390: TGTTCAAC;

scytale-391: TTGCGCTG; scytale-392: CCATATCA; scytale-393: CATATAAG;

scytale-394: TGCGCGGA; scytale-395: ATTGACTT; scytale-396: GCCAGTCC;

scytale-397: ACCAGCGG; scytale-398: GTTGATAA; scytale-399: TGTCCACG;

scytale-400: CACTTGTA; scytale-401: AAGCTAAC; scytale-402: GGATCGGT;

scytale-403: TCAATTGT; scytale-404: CTGGCCAC; scytale-405: GCGGTATG;

scytale-406: ATAACGCA; scytale-407: AATCAAGC; scytale-408: GGCTGGAT;

scytale-409: AGGTATTG; scytale-410: GAACGCCA; scytale-411: TCACATAT;

scytale-412: CTGTGCGC; scytale-413: CGAATCAG; scytale-414: TAGGCTGA;

scytale-415: ACTCGGAG; scytale-416: GTCTAAGA; scytale-417: AGGCGATT;

scytale-418: GAATAGCC; scytale-419: CTTAAGTT; scytale-420: TCCGGACC;

scytale-421: TCCGACAT; scytale-422: CTTAGTGC; scytale-423: CAAGGACT;

scytale-424: TGGAAGTC; scytale-425: GCTTCATG; scytale-426: ATCCTGCA;

scytale-427: TTCGCCTT; scytale-428: CCTATTCC; scytale-429: TGACTGAG;

scytale-430: CAGTCAGA; scytale-431: ATATTAGG; scytale-432: GCGCCGAA;

scytale-433: AATTGGAC; scytale-434: GGCCAAGT; scytale-435: CACACTTG;

scytale-436: TGTGTCCA; scytale-437: GTGATCTT; scytale-438: ACAGCTCC;

scytale-439: CTGGATAG; scytale-440: TCAAGCGA; scytale-441: TGTCGTTG;

scytale-442: CACTACCA; scytale-443: TACCTGCG; scytale-444: CGTTCATA;

scytale-445: CGACAGGT; scytale-446: TAGTGAAC; scytale-447: GTTAGTCT;

scytale-448: ACCGACTC; scytale-449: AGTAACCG; scytale-450: GACGGTTA;

scytale-451: ACGGTAGT; scytale-452: GTAACGAC; scytale-453: TTAGCTAT;

scytale-454: CCGATCGC; scytale-455: GTGCAACG; scytale-456: ACATGGTA;

scytale-457: CGACCATT; scytale-458: TAGTTGCC; scytale-459: AGCTACGG;

scytale-460: GATCGTAA; scytale-461: AATAGCTG; scytale-462: GGCGATCA;

scytale-463: CCGTCGAT; scytale-464: TTACTAGC; scytale-465: GTTGAATG;

scytale-466: ACCAGGCA; scytale-467: TACAATAG; scytale-468: CGTGGCGA;

scytale-469: TCTTCTGT; scytale-470: CTCCTCAC; scytale-471: CGATGACG;

scytale-472: TAGCAGTA; scytale-473: GTCTTGTG; scytale-474: ACTCCACA;

scytale-475: GCGAGCTG; scytale-476: ATAGATCA; scytale-477: TGTATGCT;

scytale-478: CACGCATC; scytale-479: GAACTAAT; scytale-480: AGGTCGGC;

-continued scytale-481: GCCGAGGT; scytale-482: ATTAGAAC; scytale-483: CTGAACCT;

scytale-484: TCAGGTTC; scytale-485: GATACCGG; scytale-486: AGCGTTAA;

scytale-487: CTATGTGT; scytale-488: TCGCACAC; scytale-489: TACGCTCG;

scytale-490: CGTATCTA; scytale-491: TAACGCTT; scytale-492: CGGTATCC;

scytale-493: GCCTTAGT; scytale-494: ATTCCGAC; scytale-495: ACATAATG;

scytale-496: GTGCGGCA; scytale-497: ATTGGCAG; scytale-498: GCCAATGA;

scytale-499: AACCTCGC; scytale-500: GGTTCTAT; scytale-501: CATCAACT;

scytale-502: TGCTGGTC; scytale-503: GCAGACCG; scytale-504: ATGAGTTA;

scytale-505: TAGTCCGT; scytale-506: CGACTTAC; scytale-507: TCAATCCG;

scytale-508: CTGGCTTA; scytale-509: AGCGTGGT; scytale-510: GATACAAC;

scytale-511: GAAGAGTG; scytale-512: AGGAGACA; scytale-513: CTGTTCAG;

scytale-514: TCACCTGA; scytale-515: TTCTGACG; scytale-516: CCTCAGTA;

scytale-517: CGAACGAT; scytale-518: TAGGTAGC; scytale-519: AGTGGACT;

scytale-520: GACAAGTC; scytale-521: TTCACCGG; scytale-522: CCTGTTAA;

scytale-523: GCTAGTGG; scytale-524: ATCGACAA; scytale-525: TACCGTAT;

scytale-526: CGTTACGC; scytale-527: CAATCGTT; scytale-528: TGGCTACC;

scytale-529: AAGATGTC; scytale-530: GGAGCACT; scytale-531: TCCTCAAG;

scytale-532: CTTCTGGA; scytale-533: ATACGATG; scytale-534: GCGTAGCA;

scytale-535: CTCATAAT; scytale-536: TCTGCGGC; scytale-537: TGGCACTT;

scytale-538: CAATGTCC; scytale-539: AATATGCG; scytale-540: GGCGCATA;

scytale-541: CCGGATCT; scytale-542: TTAAGCTC; scytale-543: GCTGTGAG;

scytale-544: ATCACAGA; scytale-545: AACTACTT; scytale-546: GGTCGTCC;

scytale-547: TTAGGCCT; scytale-548: CCGAATTC; scytale-549: ACTTCTAG;

scytale-550: GTCCTCGA; scytale-551: AAGCGGAA; scytale-552: GGATAAGG;

scytale-553: TATCCTGG; scytale-554: CGCTTCAA; scytale-555: GTGCCGTT;

scytale-556: ACATTACC; scytale-557: CGGAGTCG; scytale-558: TAAGACTA;

scytale-559: CCAGCCGT; scytale-560: TTGATTAC; scytale-561: ATAGAGAG;

scytale-562: GCGAGAGA; scytale-563: CACCGCTG; scytale-564: TGTTATCA;

scytale-565: GAGTAACT; scytale-566: AGACGGTC; scytale-567: CTTGGAGG;

scytale-568: TCCAAGAA; scytale-569: TTACTTCT; scytale-570: CCGTCCTC;

scytale-571: AATCTCTA; scytale-572: GGCTCTCG; scytale-573: TCGTGCAT;

scytale-574: CTACATGC; scytale-575: AAGACAAG; scytale-576: GGAGTGGA;

scytale-577: ACTTAACT; scytale-578: GTCCGGTC; scytale-579: AAGGAGGT;

scytale-580: GGAAGAAC; scytale-581: CGTCAAGG; scytale-582: TACTGGAA;

scytale-583: AGAGGCTT; scytale-584: GAGAATCC; scytale-585: CAGCTATT;

scytale-586: TGATCGCC; scytale-587: CTATATTG; scytale-588: TCGCGCCA;

scytale-589: TGCACTGT; scytale-590: CATGTCAC; scytale-591: GTCCAGAG;

scytale-592: ACTTGAGA; scytale-593: TAACCACT; scytale-594: CGGTTGTC;

scytale-595: AACATCAA; scytale-596: GGTGCTGG; scytale-597: ATGTCTAT;

scytale-598: GCACTCGC; scytale-599: TCGACTTG; scytale-600: CTAGTCCA;

-continued scytale-601: AACGCGAC; scytale-602: GGTATAGT; scytale-603: TATCTGAT;

scytale-604: CGCTCAGC; scytale-605: TCCGTTCT; scytale-606: CTTACCTC;

scytale-607: TCAAGATG; scytale-608: CTGGAGCA; scytale-609: GTATCAAG;

scytale-610: ACGCTGGA; scytale-611: GATCACTT; scytale-612: AGCTGTCC;

scytale-613: GAGCTTAG; scytale-614: AGATCCGA; scytale-615: CTCCGAGT;

scytale-616: TCTTAGAC; scytale-617: GCCAACTT; scytale-618: ATTGGTCC;

scytale-619: CGAGTGTG; scytale-620: TAGACACA; scytale-621: TCGGCAGG;

scytale-622: CTAATGAA; scytale-623: TGCCGGCT; scytale-624: CATTAATC;

scytale-625: ATGCTCCG; scytale-626: GCATCTTA; scytale-627: GATAGCAT;

scytale-628: AGCGATGC; scytale-629: AGGACGTT; scytale-630: GAAGTACC;

scytale-631: ACCTTCAG; scytale-632: GTTCCTGA; scytale-633: TGTCTCGG;

scytale-634: CACTCTAA; scytale-635: CGGTGCTT; scytale-636: TAACATCC;

scytale-637: CTAAGTAG; scytale-638: TCGGACGA; scytale-639: GCAGCGAT;

scytale-640: ATGATAGC; scytale-641: GTCGTACT; scytale-642: ACTACGTC;

scytale-643: CCACTAGT; scytale-644: TTGTCGAC; scytale-645: CATGAGAT;

scytale-646: TGCAGAGC; scytale-647: TAAGCATG; scytale-648: CGGATGCA;

scytale-649: AACCAGAT; scytale-650: GGTTGAGC; scytale-651: AGTATATG;

scytale-652: GACGCGCA; scytale-653: CCAGATGG; scytale-654: TTGAGCAA;

scytale-655: TCGTTCGG; scytale-656: CTACCTAA; scytale-657: AAGCGTCG;

scytale-658: GGATACTA; scytale-659: CGTAGCCT; scytale-660: TACGATTC;

scytale-661: GTCTGATT; scytale-662: ACTCAGCC; scytale-663: CATGCTGT;

scytale-664: TGCATCAC; scytale-665: TGAACTAG; scytale-666: CAGGTCGA;

scytale-667: CAGCCGAG; scytale-668: TGATTAGA; scytale-669: ACTGTCTG;

scytale-670: GTCACTCA; scytale-671: ACAGAGCT; scytale-672: GTGAGATC;

scytale-673: CGTTCCAG; scytale-674: TACCTTGA; scytale-675: CGAGTTCT;

scytale-676: TAGACCTC; scytale-677: CTCTAGAT; scytale-678: TCTCGAGC;

scytale-679: GCTAGGTT; scytale-680: ATCGAACC; scytale-681: CCACGCAG;

scytale-682: TTGTATGA; scytale-683: CCGACACG; scytale-684: TTAGTGTA;

scytale-685: CACAACGT; scytale-686: TGTGGTAC; scytale-687: AGCGCTTG;

scytale-688: GATATCCA; scytale-689: ATACTGGT; scytale-690: GCGTCAAC;

scytale-691: TCTTCGCG; scytale-692: CTCCTATA; scytale-693: GTCTCCGT;

scytale-694: ACTCTTAC; scytale-695: TGTAAGAG; scytale-696: CACGGAGA;

scytale-697: AAGGACCG; scytale-698: GGAAGTTA; scytale-699: AAGAGTAT;

scytale-700: GGAGACGC; scytale-701: CATGGTTG; scytale-702: TGCAACCA;

scytale-703: GCTCTAGG; scytale-704: ATCTCGAA; scytale-705: AGGCTGCT;

scytale-706: GAATCATC; scytale-707: TGGAATGG; scytale-708: CAAGGCAA;

scytale-709: AGACATCT; scytale-710: GAGTGCTC; scytale-711: ATCTAGCG;

scytale-712: GCTCGATA; scytale-713: GTCAGAAG; scytale-714: ACTGAGGA;

scytale-715: ACTATCCT; scytale-716: GTCGCTTC; scytale-717: GTACGCAT;

scytale-718: ACGTATGC; scytale-719: GATCCTCT; scytale-720: AGCTTCTC;

scytale-721: TGTGCAGT; scytale-722: CACATGAC; scytale-723: CTTACGAG;

-continued scytale-724: TCCGTAGA; scytale-725: GCACCTAG; scytale-726: ATGTTCGA;

scytale-727: CTTCTCTT; scytale-728: TCCTCTCC; scytale-729: GAGAGGAG;

scytale-730: AGAGAAGA; scytale-731: CGATCTGG; scytale-732: TAGCTCAA;

scytale-733: AGTAGTAG; scytale-734: GACGACGA

Example 3

10-mer Index Set

This example describes the design considerations for a set of 10-mer index sequences according to some implementations and lists the sequences in the index set. The index set supports a larger number of indices and keeps the index length at 10 bp. The summary of the design strategy is given below.

No direct match of index sequence with 10-mer subsequence (or reverse complement) of a sequencing platform adapter or primer sequences, e.g.,
SBS491
P7
P5
SBS3
No occurrence of four nucleotide homopolymer
GC content between 25% and 75% (inclusive)
No sequence listed in Table 4 is used (known poor performer)
Minimum Hamming distance of 4
Minimum modified edit distance of 3
Indices provided as color-balanced pairs A total of 1026 10-mer sequences are obtained, and they are combined and shown in a combined sequence of SEQ ID NO: 9. The $n^{th}$ 10-mer sequence includes nucleotides $10(n-1)+1, 10(n-1)+2, 10(n-1)+3, \ldots, 10(n-1)+10$ in SEQ ID NO: 9. The $(2m-1)^{th}$ and $2 m^{th}$ 10-mers in SEQ ID NO: 9 are color balanced, wherein m is an integer between 1 and 513. In some implementations, a set of index sequences are obtained. The set of index sequences includes the 1026 10-mer sequences of SEQ ID NO: 9. In some implementation, oligonucleotides are generated using index sequences. The oligonucleotides include double-stranded or Y-shaped sequencing adapters. Each strand of each double-stranded or Y-shaped sequencing adapter includes an index sequence corresponding to a 10-mer in SEQ ID NO: 9. In other implementations, the set of oligonucleotides includes pairs of single-stranded oligonucleotides, e.g., pairs of primers. Each pair of single-stranded oligonucleotides is provided together in a reagent. Each oligonucleotide of a pair includes an index sequence corresponding to a 10-mer in SEQ ID NO: 9.

Ten subsets are selected from the 1026 10-mers in SEQ ID NO: 9 as subsets of index sequences. To select subsets of 10-mers, double-stranded sequencing adapters are used to perform sequencing. Each strand of the double-stranded sequencing adapters includes an index sequence from the 1026 sequences in SEQ ID NO: 9. Different pairs of index sequences are used to generate different sequencing adapters. The sequencing performance of the adapters is measured. Based on the measured sequencing performance, index sequences are ranked. Using ranks of the index sequences as a criterion, one or more subsets of 10-mer sequences can be selected from the 1026 sequences.

In some implementations, a subset of 96 different pairs of the index sequences having the highest sequencing performance are selected. In one implementation, each pair of the 96 pairs of the index sequences includes an $n^{th}$ 10-mer in SEQ ID NO: 10, and an $n^{th}$ 10-mer in SEQ ID NO: 11.

The 10-mers in each of the ten subsets are combined and shown in a combined sequence. The ten subsets respectively correspond to ten combined sequences: SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19. The $n^{th}$ 10-mer sequence in a combined sequence includes nucleotides $10(n-1)+1, 10(n-1)+2, 10(n-1)+3, \ldots, 10(n-1)+10$ in. The $(2m-1)^{th}$ and $2 m^{th}$ 10-mers in SEQ ID NO: 10 to SEQ ID NO: 19 are color balanced, wherein m is a positive integer. Each 10-mer is different from any other 10-mer in a subset. Each 10-mer in any of five subsets (corresponding to SEQ ID NO: 10, SEQ ID NO: 12, SEQ ID NO: 14, SEQ ID NO: 16, and SEQ ID NO: 18) is different from every other 10-mer in any of the five subsets. Each 10-mer in any of additional five subsets (corresponding to SEQ ID NO: 11, SEQ ID NO: 13, SEQ ID NO: 15, SEQ ID NO: 17, and SEQ ID NO: 19) is different from every other 10-mer in any of the additional five subsets.

In some implementations, each Y-shaped or double-stranded sequencing adapter includes a first strand including a first index sequence selected from a first subset of the set of index sequences, and a second strand including a second index sequence selected from a second subset of the set of index sequences (or reverse complements of the second subset). In some implementations, each pair of oligonucleotides (e.g., primers) includes a first oligonucleotide including a first index sequence selected from a first subset of the set of index sequences and a second oligonucleotide including a second index sequence selected from a second subset of the set of index sequences (or reverse complements of the second subset).

In some implementations, the first and the second index sequences respectively are: the $n^{th}$ 10-mer in SEQ ID NO: 10 and $n^{th}$ 10-mer in SEQ ID NO: 11 (or a reverse complement of SEQ ID NO: 11); the $n^{th}$ 10-mer in SEQ ID NO: 12 and $n^{th}$ 10-mer in SEQ ID NO: 13 (or a reverse complement thereof); the $n^{th}$ 10-mer in SEQ ID NO: 14 and $n^{th}$ 10-mer in SEQ ID NO: 15 (or a reverse complement thereof); the $n^{th}$ 10-mer in SEQ ID NO: 16 and $n^{th}$ 10-mer in SEQ ID NO: 17 (or a reverse complement thereof); the $n^{th}$ 10-mer in SEQ ID NO: 18 and $n^{th}$ 10-mer in SEQ ID NO: 19 (or a reverse complement thereof).

In some implementations, the first and second index sequences are comprised in oligos provided in one reaction compartment of a container comprising multiple separate compartments. Each compartment contains (a) a first plurality of oligonucleotides including a first index sequence and (b) a second plurality of oligonucleotides including a second index sequence, an ordered combination of (a) and (b) in the compartment being different from ordered combinations of (a) and (b) in any other compartments.

In some implementations, the container comprises a multi-well plate. In some implementations, the container includes 8×12 compartments. With the compartments labeled as A-H rows and 1-12 columns, they can be listed as A1, A2, A3, ..., A12, B1, B2, ..., B12, ..., H1, H2, ..., H12. In some implementations, in the $n^{th}$ compartment on the list, the first and the second index sequences respectively are: the $n^{th}$ 10-mer in SEQ ID NO: 10 and the $n^{th}$ 10-mer in SEQ ID NO: 11 (or a reverse complement of the $n^{th}$ 10-mer in SEQ ID NO: 11); the $n^{th}$ 10-mer in SEQ ID NO: 12 and the $n^{th}$ 10-mer in SEQ ID NO: 13 (or a reverse complement of the $n^{th}$ 10-mer in SEQ ID NO: 13); the $n^{th}$ 10-mer in SEQ ID NO: 14 and the $n^{th}$ 10-mer in SEQ ID NO: 15 (or a reverse complement thereof); or the $n^{th}$ 10-mer in SEQ ID NO: 16 and the $n^{th}$ 10-mer in SEQ ID NO: 17 (or a reverse complement thereof).

What is claimed is:

1. A method for processing target nucleic acids derived from a plurality of samples, comprising:
   (a) contacting a plurality of index polynucleotides with target nucleic acids derived from the plurality of samples to generate a plurality of index-target polynucleotides, wherein:
   index polynucleotides contacted with target nucleic acids derived from each sample comprise an index sequence or a combination of index sequences that is uniquely associated with that sample,
   the index sequence or the combination of index sequences is selected from a set of index sequences, and
   the set of index sequences comprises a plurality of pairs of color-balanced index sequences, wherein any two bases at corresponding sequence positions of each pair of color-balanced index sequences include both (i) an adenine (A) base or a cytosine (C) base, and (ii) a guanine (G) base, a thymine (T) base, or a uracil (U) base.

2. The method of claim 1, further comprising: pooling the plurality of index-target polynucleotides.

3. The method of claim 2, further comprising: sequencing the pooled index-target polynucleotides to obtain a plurality of index reads of index sequences and a plurality of target reads of target sequences, each target read being associated with at least one index read.

4. The method of claim 3, further comprising: using the index reads to determine the target reads' sources of samples.

5. The method of claim 4, wherein using the index reads to determine the target reads' sources of samples comprises:
   obtaining, for each index read, alignment scores with respect to the set of index sequences, each alignment score indicating similarity between a sequence of the index read and an index sequence of the set of index sequences;
   determining that a particular index read is aligned to a particular index sequence based on the alignment scores; and
   determining that a target read associated with the particular index read is derived from a sample uniquely associated with the particular index sequence.

6. The method of claim 1, wherein the set of index sequences comprises at least 6 different index sequences.

7. The method of claim 1, wherein the plurality of index polynucleotides comprises a plurality of index primers comprising index sequences of the set of index sequences.

8. The method of claim 7, wherein each index primer further comprises a flow cell amplification primer binding sequence.

9. The method of claim 7, wherein the target nucleic acids derived from the plurality of samples comprise nucleic acids with universal adapters covalently attached to one or both ends.

10. The method of claim 9, wherein the universal adapters comprise double-stranded adapters.

11. The method of claim 9, wherein the universal adapters comprise Y-shaped adapters.

12. The method of claim 9, wherein the universal adapters comprise single-stranded adapters.

13. The method of claim 9, wherein the universal adapters comprise hairpin adapters.

14. A method of processing a plurality of nucleic acid samples, comprising:
   applying a different oligonucleotide of a set of oligonucleotides to target nucleic acids of each nucleic acid sample of the plurality of nucleic acid samples, thereby generating a plurality of index-target polynucleotides, wherein
   the set of oligonucleotides is configured to identify sources of nucleic acid samples in multiplex massively parallel sequencing;
   each oligonucleotide of the set of oligonucleotides comprises an index sequence;
   the set of oligonucleotides comprises a set of index sequences comprising at least 6 different index sequences; and
   the set of index sequences comprises a plurality of pairs of color-balanced index sequences, wherein any two bases at corresponding sequence positions of each pair of color-balanced index sequences include both (i) an adenine (A) base or a cytosine (C) base, and (ii) a guanine (G) base, a thymine (T) base, or a uracil (U) base;

pooling the plurality of index-target polynucleotides;
sequencing the plurality of index-target polynucleotides; and
determining, using the set of index sequences, sources of nucleic acid samples from which the plurality of index-target polynucleotides is derived.

15. The method of claim 14, wherein a Hamming distance between any two index sequences of the set of index sequences is not less than a first criterion value, wherein the first criterion value is at least 2.

16. A method for processing target nucleic acids derived from a plurality of samples, comprising:
   (a) providing a plurality of double-stranded nucleic acid molecules derived from the plurality of samples;
   (b) providing a plurality of transposome complexes, wherein each transposome complex comprises a transposase and two transposon end compositions;
   (c) incubating the double-stranded nucleic acid molecules with the transposome complexes to obtain double-stranded nucleic acid fragments, wherein the double-stranded nucleic acid fragments comprise, at one or both ends, sequences transposed from the transposon end compositions;
   (d) contacting a plurality of index primers with the double-stranded nucleic acid fragments to generate a plurality of index-fragment polynucleotides, wherein:
      index primers contacted with double-stranded nucleic acid fragments derived from each sample comprise an index sequence or a combination of index sequences that is uniquely associated with that sample,
      the index sequence or the combination of index sequences is selected from a set of index sequences; and
      the set of index sequences comprises a plurality of pairs of color-balanced index sequences, wherein any two bases at corresponding sequence positions of each pair of color-balanced index sequences include both (i) an adenine base or a cytosine base, and (ii) a guanine base, a thymine base, or a uracil base.

17. The method of claim 16, further comprising: (e) pooling the plurality of index-fragment polynucleotides.

18. The method of claim 17, further comprising: (f) sequencing the pooled index-fragment polynucleotides, thereby obtaining index reads of index sequences and a plurality of target reads of target sequences, each target read being associated with at least one index read.

19. The method of claim 18, further comprising: (g) using the index reads to determine the target reads' sources of samples.

20. The method of claim 16, wherein a Hamming distance between any two index sequences of the set of index sequences is not less than a first criterion value, wherein the first criterion value is at least 2.

* * * * *